United States Patent
Ghosh et al.

(10) Patent No.: US 10,106,605 B2
(45) Date of Patent: Oct. 23, 2018

(54) COMPOSITIONS AND METHODS FOR ANTIBODIES TARGETING EPO

(71) Applicant: Novartis AG, Basel (CH)

(72) Inventors: Joy Ghosh, Brookline, MA (US); Mark Anthony Rutz, Munich (DE); Kathrin Ulrike Tissot-Daguette, Neuried (DE); Igor Splawski, Cambridge, MA (US); Michael Roguska, Cambridge, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/180,879

(22) Filed: Jun. 13, 2016

(65) Prior Publication Data

US 2016/0280783 A1   Sep. 29, 2016

Related U.S. Application Data

(62) Division of application No. 14/095,910, filed on Dec. 3, 2013, now Pat. No. 9,365,646.

(60) Provisional application No. 61/733,566, filed on Dec. 5, 2012.

(51) Int. Cl.
| | |
|---|---|
| *A61K 39/00* | (2006.01) |
| *C07K 16/22* | (2006.01) |
| *C07K 16/26* | (2006.01) |
| *C07K 16/28* | (2006.01) |
| *A61K 39/395* | (2006.01) |
| *A61K 45/06* | (2006.01) |

(52) U.S. Cl.
CPC .......... *C07K 16/26* (2013.01); *A61K 39/3955* (2013.01); *A61K 45/06* (2013.01); *C07K 16/22* (2013.01); *A61K 2039/505* (2013.01); *A61K 2039/507* (2013.01); *C07K 2317/21* (2013.01); *C07K 2317/34* (2013.01); *C07K 2317/55* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,703,008 | A | 10/1987 | Lin |
| 5,712,370 | A | 1/1998 | Fibi et al. |
| 7,396,913 | B2 | 7/2008 | Devries et al. |
| 2002/0045582 | A1 | 4/2002 | Margolin et al. |
| 2003/0049683 | A1 | 3/2003 | Bowdish et al. |
| 2003/0050269 | A1 | 3/2003 | Escary |
| 2004/0091961 | A1 | 5/2004 | Evans et al. |
| 2005/0255112 | A1 | 11/2005 | Lee et al. |
| 2007/0224201 | A1 | 9/2007 | Wu et al. |
| 2009/0004202 | A1 | 1/2009 | Brines et al. |
| 2009/0238789 | A1 | 9/2009 | Guyon et al. |
| 2009/0252746 | A1 | 10/2009 | Devries et al. |
| 2011/0053787 | A1 | 3/2011 | Brulliard et al. |
| 2011/0091463 | A1 | 4/2011 | Ghayur et al. |
| 2011/0091474 | A1 | 4/2011 | Zhang |
| 2011/0143372 | A1 | 6/2011 | Jarsch et al. |
| 2012/0082681 | A1 | 4/2012 | Carballido Herrera et al. |
| 2012/0195900 | A1 | 8/2012 | Ghayur et al. |
| 2012/0201746 | A1 | 8/2012 | Liu et al. |
| 2012/0207743 | A1 | 8/2012 | Jacky et al. |
| 2013/0064836 | A1 | 3/2013 | Diefenbach-Streiber et al. |
| 2014/0199306 | A1 | 7/2014 | Ghosh et al. |

FOREIGN PATENT DOCUMENTS

| | | |
|---|---|---|
| EP | 1611879 A1 | 1/2006 |
| EP | 1736481 A1 | 12/2006 |
| EP | 1699826 B1 | 3/2009 |
| EP | 2062917 A2 | 5/2009 |
| EP | 1732950 B1 | 5/2011 |
| EP | 2120998 B1 | 8/2013 |
| WO | 9008822 A1 | 8/1990 |
| WO | 2004060270 A2 | 7/2004 |
| WO | 2004089282 A2 | 10/2004 |
| WO | 2007060213 A2 | 5/2007 |
| WO | 2007120766 A2 | 10/2007 |
| WO | 2008079877 A2 | 7/2008 |
| WO | 2009015345 A1 | 1/2009 |
| WO | 2009080816 A1 | 7/2009 |
| WO | 2009094551 A1 | 7/2009 |
| WO | 2010054007 A1 | 5/2010 |
| WO | 2010056893 A1 | 5/2010 |
| WO | 2010081679 A1 | 7/2010 |
| WO | 2012171996 A1 | 12/2012 |
| WO | 2013106489 A1 | 7/2013 |
| WO | 2013169734 A1 | 11/2013 |

(Continued)

OTHER PUBLICATIONS

Ascaso et al. The role of inflammation in the pathogenesis of macular edema secondary to retinal vascular diseases. Mediators of Inflammation, vol. 2014, pp. 1-6 (2014).*
Kent et al. Macular oedema: the role of soluble mediators. British Journal of Ophthalmology vol. 84/No. 5:542-545 (2000).*
Bainbridge et al. Inhibition of retinal neovascularization by gene transfer of soluble VEGF receptor sFitl-1. Gene therapy, vol. 9:320-326 (2002).*
Yoshida et al. Suppression of retinal neovascularization by the NF-kB inhibitor pyrrolidine dithiocarbamate in mice. IOVS, vol. 40/No. 7, pp. 1624-1629 (1999).*

(Continued)

*Primary Examiner* — Elizabeth C. Kemmerer
*Assistant Examiner* — Regina M DeBerry
(74) *Attorney, Agent, or Firm* — Sherwin Y. Chan

(57) ABSTRACT

The present invention relates to compositions and methods for the inhibition of EPO. The invention provides antibodies and antigen binding fragments thereof that bind to EPO and are able to inhibit EPO-dependent cell proliferation and/or EPO-dependent cell signaling.

14 Claims, 3 Drawing Sheets
Specification includes a Sequence Listing.

(56) References Cited

FOREIGN PATENT DOCUMENTS

WO     2014035693 A2     3/2014

OTHER PUBLICATIONS

Garcia-Ramirez et al. Erythropoietin protects retinal pigment epithelial cells against the increase of permeability induced by diabetic conditions: Essential role of JAK2/PI3K signaling. Cellular Signaling vol. 23:1506-1602 (2011). (Year: 2011).*
Li et al. Effects of Intravitreal Erythropoietin Therapy for Patients with Chronic and Progressive Diabetic Macular Edema. Ophthalmic Surgery, Lasers and Imaging Retina. Abstract. 41(1):18-26 (2010). (Year: 2010).*
Zhang et al. Intravitreal Injection of Erythropoietin Protects both Retinal Vascular and Neuronal Cells in Early Diabetes. Investigative Ophthalmology & Visual Science, vol. 49, No. 2 (Feb. 2008). (Year: 2008).*
Elliott et al., Fine-structure epitope mapping of antierythropoietin monoclonal antibodies reveals a model of recombinant human erythropoietin structure. Blood. Apr. 1, 1996;87(7):2702-13.
Elliott et al., Isolation and characterization of conformation sensitive antierythropoietin monoclonal antibodies: effect ofdisulfide bonds and carbohydrate on recombinant human erythropoietin structure. Blood. Apr. 1, 1996;87(7):2714-22.
Javey et al., Emerging pharmacotherapies for diabetic macular edema. Exp Diabetes Res. 2012;2012:548732. 12 pages. Epub Feb. 26, 2012.
Watanabe et al., Erythropoietin as a retinal angiogenic factor in proliferative diabetic retinopathy. N Engl J Med. Aug. 25, 2005;353(8):782-92.
Yanagihara et al., Production of novel anti-recombinant human erythropoietin monoclonal antibodies and development of a sensitive enzyme-linked immunosorbent assay for detection of bioactive human erythropoietin. J Immunoassay Immunochem. 2008;29(2):181-96.
Paul, "Fv Structure and Diversity in Three Dimensions". Fundamental Immunology, 3rd Edition, pp. 292-295 (1993).
Rudikoff et al., "Single amino acid substitution altering antigen-binding specificity," Proc Natl Acad Sci U S A. Mar. 1982;79(6):1979-83.
Arnadeo et al., "A single monoclonal antibody as probe to detect the entire set of native and partially unfolded rhEPO glycoforms," J Immunol Methods. Oct. 2004;293(1-2):191-205.
D'Andrea et al., "Inhibition of receptor binding and neutralization of bioactivity by anti-erythropoietin monoclonal antibodies," Blood. Feb. 15, 1990;75(4):874-80.
Goto et al., "Characterization and use of monoclonal antibodies directed against human erythropoietin that recognize different antigenic determinants," Blood. Sep. 1989;74(4):1415-23.
Sue et al., "Site-specific antibodies to human erythropoietin directed toward the NH2-terminal region," Proc Natl Acad Sci U S A. Jun. 1983;80(12):3651-5.
Sytkowski et al., "Isolation and characterization of an anti-peptide monoclonal antibody to human erythropoietin," J Biol Chem. Nov. 25, 1985;260(27):14727-31.
Yanagihara et al., "Production of novel anti-recombinant human erythropoietin monoclonal antibodies and development of a sensitive enzyme-linked immunosorbent assay for detection of bioactive human erythropoietin," J Immunoassay Immunochem. 2008;29(2)181-96.
Fibi et al., "Human erythropoietin-specific sites of monoclonal antibody-mediated neutralization," Blood. Feb. 1, 1993;81 (3):670-5.
Elliott et al., "Mapping of the active site of recombinant human erythropoietin," Blood. Jan. 15, 1997;89(2):493-502.
Du et al. "Molecular Basis of Recognition of Human Osteopontin by 23C3, a Potential Therapeutic Antibody for Treatment of Rheumatoid Arthritis" J. Mol. Biol. (2008), vol. 382, pp. 835-842.
Caldas et al. "Humanization of the anti-CD18 antibody 6.7: an unexpected effect of a framework residue in binding to antigen" Molecular Immunology (2003), vol. 39, pp. 941-952.

* cited by examiner

COMPOSITIONS AND METHODS FOR ANTIBODIES TARGETING EPO

CROSS REFERENCE TO RELATED APPLICATIONS

This application is a division of U.S. application Ser. No. 14/095,910, filed on Dec. 3, 2013, now U.S. Pat. No. 9,365,646, which claims the benefit of U.S. Application No. 61/733,566, filed on Dec. 5, 2012, the entire contents of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Mar. 11, 2014, is named PAT054963-US-NP_SL.txt and is 61,177 bytes in size.

BACKGROUND OF THE INVENTION

Diabetic retinopathy (DR) is the most common complication in patients with diabetes. Diabetic macular edema (DME) can occur in any stage of DR and is the main cause of vision loss in patients with DR. The incidence of DME after 10 years of follow-up has been reported to be 20.1% in Type 1 diabetes, 25.4% in Type 2 insulin-dependent diabetes, and 13.9% in Type 2 non-insulin-dependent diabetes (Klein et al. (1995) Ophthalmology 102, 7-16). The ETDRS trial ((1985) Photocoagulation for Diabetic Macular Edema—Early Treatment Diabetic-Retinopathy Study Report. 1. Archives of Ophthalmology 103, 1796-1806), a pioneering study in DR, demonstrated that although laser photocoagulation therapy reduces the risk of moderate visual loss in DME eyes by ~50% at 3 years, only a few eyes gain vision, and some eyes continue to experience vision loss even after intensive treatment. In recent years, advances in pharmacotherapy and ocular drug delivery have shown promise in the treatment of DME. The RESTORE study, one of two pivotal Phase III trials in DME (Mitchell et al. (2011) Ophthalmology 118, 615-625) demonstrated that Lucentis® was superior to laser monotherapy. The mean change in best-corrected visual acuity (BCVA), which was the primary clinical endpoint, was significantly improved in the Lucentis® group (+6.1 letters for the Lucentis® group vs. +0.8 letters for the laser group; p<0.0001). Similar beneficial effects have been demonstrated with VEGF Trap-Eye (Regeneron Inc. NY, USA) and Ozurdex® (dexamethasone intravitreal implant; Allergan Inc., CA, USA)(Do et al. (2011) Ophthalmology 118, 1819-1826; Haller et al. (2010) Archives of Ophthalmology 128, 289-296). However, 16% of Ozurdex treated eyes developed increased intra-ocular pressure, a risk for glaucoma.

Despite these new treatment options for DME, there remains a substantial unmet medical need. ~25% of eyes in the Lucentis® pivotal trials did not gain any visual acuity after 12 months of treatment and ~50% of eyes are left with visual acuity of 20/40 or worse. Genome-wide association studies indicated that diabetics who are homozygous for an erythropoietin (Epo) promoter polymorphism (T) have a 2.17-fold higher risk of developing proliferative DR (Tong et al. (2008) Proc. Natl. Acad. Sci. U.S.A 105, 6998-7003). Interestingly, people with the T promoter allele for Epo have approximately 7.5-fold higher vitreal concentration of Epo compared to people with the G allele (Tong et al. (2008) Proc. Natl. Acad. Sci. U.S.A 105, 6998-7003).

There remains a need to develop an effective treatment for diabetic retinopathy, particularly DME to replace or supplement current treatments.

SUMMARY OF THE INVENTION

The invention relates to antibodies, or antigen binding fragments, as described herein which bind Epo and/or Darbepoietin.

The isolated antibodies, or antigen binding fragments, described herein bind Epo and/or Darbepoietin, with a $K_D$ of less than or equal to 100 pM. For example, the isolated antibodies or antigen binding fragments described herein may bind to human Epo and/or Darbepoietin with a $K_D$ of less than or equal to 50 pM, less than or equal to 40 pM, less than or equal to 35 pM, less than or equal to 30 pM, less than or equal to 25 pM, less than or equal to 20 pM, less than or equal to 15 pM, less than or equal to 14 pM, less than or equal to 13 pM, less than or equal to 12 pM, less than or equal to 11 pM, less than or equal to 10 pM. More specifically, the isolated antibodies or antigen binding fragments described herein may also bind human Epo with a $K_D$ of less than or equal to 35 pM, as measured by Biacore, or less than or equal to 6 pM, as measured by Solution Equilibrium Titration (SET). More specifically, the isolated antibodies or antigen binding fragments described herein may also bind Darbepoietin with a $K_D$ of less than or equal to 24 pM, as measured by Biacore, or less than or equal to 4 pM, as measured by SET.

The present invention relates to an isolated antibody, or antigen binding fragment thereof, that binds to human, cynomolgus, mouse and/or rat Epo. The invention also relates to an isolated antibody, or antigen binding fragment thereof, that binds a conformational epitope comprising amino acids selected from human Epo Helix D and Loop A-B. The invention further relates to an isolated antibody, or antigen binding fragment thereof, that binds a conformational epitope comprising amino acids selected from human Epo Helix D, Loop A-B and Helix A. In particular aspects of the invention, the isolated antibodies, or antigen binding fragments thereof, may bind to the D Helix domain of Epo (amino acids 138-162 of Human Epo; SEQ ID NO: 88). In other aspects, the isolated antibodies, or antigen binding fragments described herein may bind the Loop A-B domain (amino acids 27-55 of Human Epo; SEQ ID NO: 89). In other aspects the isolated antibodies, or antigen binding fragments described herein may bind the Loop A-B domain (amino acids 27-55 of Human Epo; SEQ ID NO: 89) and Helix A (amino acids 4-26 of Human Epo; SEQ ID NO: 86). In further aspects of the invention, the isolated antibodies, or antigen binding fragments described herein may bind the D Helix domain of Epo (amino acids 138-162 of Human Epo; SEQ ID NO: 88), and the Loop A-B domain (amino acids 27-55 of Human Epo; SEQ ID NO: 89). In still further aspects of the invention, the isolated antibodies, or antigen binding fragments described herein may bind the D Helix domain of Epo (amino acids 138-162 of Human Epo; SEQ ID NO: 88), and Helix A (amino acids 4-26 of Human Epo; SEQ ID NO: 86). In still further aspects of the invention, the isolated antibodies, or antigen binding fragments described herein may bind the D Helix domain of Epo (amino acids 138-162 of Human Epo; SEQ ID NO: 88), the Loop A-B domain (amino acids 27-55 of Human Epo; SEQ ID NO: 89) and Helix A (amino acids 4-26 of Human Epo; SEQ ID NO: 86).

The present invention also relates to an isolated antibody, or antigen binding fragment thereof, that binds a confirmational epitope on Epo comprising amino acid residues Thr44, Lys45, Val46, Asn47, Phe48, Tyr49, Ala50, Lys52, Arg53, Asn147, Arg150, Gly151, Lys154, Leu155, Glu159, and Arg162 of Human Epo (SEQ ID NO. 81). The present invention further relates to an isolated antibody, or antigen binding fragment thereof, that binds a confirmational epitope on Epo comprising amino acids residues Ser9, Gln13, Thr44, Lys45, Val46, Asn47, Phe48, Tyr49, Ala50, Lys52, Arg53, Asn147, Arg150, Gly151, Lys154, Leu155, Gly158, Glu159, and Arg162, of Human Epo (SEQ ID NO. 81). The present invention still further relates to relates to an isolated antibody, or antigen binding fragment thereof, that binds a confirmational epitope on Epo comprising amino acid residues Glu23, Asp43, Thr44, Lys45, Val46, Asn47, Phe48, Tyr49, Ala50, Lys52, Arg53, Arg131, Arg143, Asn147, Arg150, Gly151, Lys154, Leu155, Glu159, and Arg162 of Human Epo (SEQ ID NO. 81).

The present invention also relates to an isolated antibody, or antigen binding fragment thereof, that binds Epo and further competes for binding with an antibody as described in Table 1. The present invention also further relates to an isolated antibody, or antigen binding fragment thereof, that binds the same epitope as an antibody as described in Table 1.

The present invention also relates to an isolated antibody, or antigen binding fragment thereof, that binds Epo and has an isoelectric point (pI) greater than 8.2, greater than 8.3, greater than 8.4, greater than 8.5 or greater than 9.0.

The isolated antibodies or antigen binding fragments described herein may also bind cynomolgus Epo, mouse Epo and/or rat Epo with a $K_D$ of less than or equal to 100 pM, less than or equal to 80 pM, less than or equal to 70 pM, less than or equal to 60 pM, less than or equal to 50 pM, less than or equal to 40 pM, less than or equal to 35 pM, less than or equal to 30 pM, less than or equal to 25 pM, less than or equal to 20 pM, less than or equal to 15 pM, less than or equal to 10 pM, less than or equal to 5 pM, less than or equal to 4 pM, less than or equal to 3 pM, less than or equal to 2 pM, less than or equal to 1 pM. More specifically, the isolated antibodies or antigen binding fragments described herein may also bind cynomolgus Epo, mouse Epo and/or rat Epo with a $K_D$ of less than or equal to 80 pM, as measured by Biacore, or less than or equal to 40 pM, as measured by SET. More specifically, the isolated antibodies or antigen binding fragments described herein may also bind Cynomolgus Epo with a $K_D$ of less than or equal to 80 pM, as measured by Biacore, or less than or equal to 8 pM, as measured by SET. More specifically, the isolated antibodies or antigen binding fragments described herein may also bind mouse Epo with a $K_D$ of less than or equal to 45 pM, as measured by Biacore, or less than or equal to 37 pM, as measured by SET. More specifically, the isolated antibodies or antigen binding fragments described herein may also bind rat Epo with a $K_D$ of less than or equal to 57 pM, as measured by Biacore, or less than or equal to 13 pM, as measured by SET.

The binding affinity of isolated antibodies and antigen binding fragments described herein can be determined by SET. Methods for SET are known in the art and are described in further detail below. Alternatively, binding affinity of the isolated antibodies, or fragments, described herein can be determined by Biacore assay. Methods for Biacore kinetic assays are known in the art and are described in further detail below.

The isolated antibodies and antigen binding fragments described herein can be used to inhibit Epo-dependent cell proliferation with an $IC_{50}$ of less than or equal to 350 pM, less than or equal to 300 pM, less than or equal to 250 pM, less than or equal to 200 pM, less than or equal to 190 pM, less than or equal to 180 pM, less than or equal to 175 pM, less than or equal to 170 pM, less than or equal to 160 pM, less than or equal to 150 pM, less than or equal to 125 pM, less than or equal to 115 pM, less than or equal to 110 pM, less than or equal to 100 pM, less than or equal to 90 pM, or less than or equal to 80 pM. More specifically, an isolated antibody or antigen binding fragment thereof as described herein can inhibit Epo-dependent cell proliferation as measured by an in vitro Ba/F3-EpoR cell proliferation assay with an $IC_{50}$ of less than or equal to 338 pM, less than or equal to 183 pM, less than or equal to 175 pM, less than or equal to 174 pM, less than or equal to 145 pM, less than or equal to 112 pM, less than or equal to 89 pM, or less than or equal to 74 pM.

The isolated antibodies and antigen binding fragments described herein can be used to inhibit Epo-dependent cell proliferation in B-cells. More specifically, the isolated antibodies and antigen binding fragments described herein can be used to inhibit Epo-dependent cell proliferation in mouse B-cells. For example, an isolated antibody or antigen binding fragment thereof can inhibit Epo-dependent cell proliferation as measured by an in vitro Ba/F3-EpoR cell proliferation assay with an $IC_{50}$ of less than or equal to 350 pM, less than or equal to 300 pM, less than or equal to 250 pM, less than or equal to 200 pM, less than or equal to 175 pM, less than or equal to 150 pM, less than or equal to 125 pM, less than or equal to 115 pM, less than or equal to 110 pM, less than or equal to 100 pM, less than or equal to 90 pM, or less than or equal to 80 pM. More specifically, an isolated antibody or antigen binding fragment thereof as described herein can inhibit Epo-dependent cell proliferation as measured by an in vitro Ba/F3-EpoR cell proliferation assay with an $IC_{50}$ of less than or equal to 338 pM, less than or equal to 174 pM, less than or equal to 112 pM, or less than or equal to 74 pM.

The isolated antibodies and antigen binding fragments described herein can be used to inhibit Epo-dependent cell proliferation of human B-cells. For example, an isolated antibody or antigen binding fragment thereof can inhibit Epo-dependent cell proliferation, as measured by an in vitro F36E cell proliferation assay, with an $IC_{50}$ of less than or equal to 200 pM, less than or equal to 190 pM, less than or equal to 180 pM, less than or equal to 170 pM, less than or equal to 160 pM, less than or equal to 150 pM, less than or equal to 125 pM, less than or equal to 100 pM, or less than or equal to 90 pM. More specifically, an isolated antibody or antigen binding fragment thereof as described herein can inhibit Epo-dependent cell proliferation as measured by an in vitro F36E cell proliferation assay with an $IC_{50}$ of less than or equal to 183 pM, less than or equal to 175 pM, less than or equal to 145 pM, or less than or equal to 89 pM.

The isolated antibodies, or antigen binding fragments thereof, may also block Epo binding to the Epo receptor and/or prevent Epo binding to a cell surface.

Another aspect of the invention includes an isolated antibody, or antigen binding fragment thereof, that specifically binds to human, cynomolgus, mouse and/or rat Epo. In a further aspect, the isolated antibody, or antigen binding fragment, competes for binding with an antibody, or antigen binding fragment, described in Table 1.

The isolated antibodies, or antigen binding fragments thereof, as described herein can be monoclonal antibodies, human or humanized antibodies, chimeric antibodies, single chain antibodies, Fab fragments, Fv fragments, F(ab')2 fragments, or ScFv fragments, and/or IgG isotypes.

The isolated antibodies, or antigen binding fragments thereof, as described herein can also include a framework in which an amino acid has been substituted into the antibody framework from the respective human VH or VL germline sequences.

Another aspect of the invention includes an isolated antibody or antigen binding fragment thereof having the full heavy and light chain sequences of Fabs described in Table 1. More specifically, the isolated antibody or antigen binding fragment thereof can have the heavy and light chain sequences of Fab NVS1, NVS2, NVS3, or NVS4.

A further aspect of the invention includes an isolated antibody or antigen binding fragment thereof having the heavy and light chain variable domain sequences of Fabs described in Table 1. More specifically, the isolated antibody or antigen binding fragment thereof can have the heavy and light chain variable domain sequence of Fab NVS1 (SEQ ID NOs 13 and 14, respectively), NVS2 (SEQ ID NOs 33 and 34, respectively), NVS3 (SEQ ID NOs 53 and 54, respectively), or NVS4 (SEQ ID NOs 73 and 74, respectively).

The invention also relates to an isolated antibody or antigen binding fragment thereof that includes a heavy chain CDR1 selected from the group consisting of SEQ ID NOs 1, 21, 41, and 61; a heavy chain CDR2 selected from the group consisting of SEQ ID NOs: 2, 22, 42, and 62; and a heavy chain CDR3 selected from the group consisting of SEQ ID NOs: 3, 23, 43, and 63, wherein the isolated antibody or antigen binding fragment thereof binds to human Epo. In another aspect, such isolated antibody or antigen binding fragment thereof further includes a light chain CDR1 selected from the group consisting of SEQ ID NOs: 4, 24, 44, and 64; a light chain CDR2 selected from the group consisting of SEQ ID NOs 5, 25, 45, and 65; and a light chain CDR3 selected from the group consisting of SEQ ID NOs 6, 26, 46, and 66.

The invention also relates to an isolated antibody or antigen binding fragment thereof that includes a light chain CDR1 selected from the group consisting of SEQ ID NOs: 4, 24, 44, and 64; a light chain CDR2 selected from the group consisting of SEQ ID NOs 5, 25, 45, and 65; and a light chain CDR3 selected from the group consisting of SEQ ID NOs 6, 26, 46, and 66, wherein the isolated antibody or antigen binding fragment thereof binds to human Epo.

The invention also relates to an isolated antibody or antigen binding fragment thereof that binds Epo having HCDR1, HCDR2, HCDR3 and LCDR1, LCDR2, LCDR3, wherein HCDR1, HCDR2, HCDR3 comprises SEQ ID NOs: 1, 2, 3, and LCDR1, LCDR2, LCDR3 comprises SEQ ID NOs: 4, 5, 6; or HCDR1, HCDR2, HCDR3 comprises SEQ ID NOs: 21, 22, 23, and LCDR1, LCDR2, LCDR3 comprises SEQ ID NOs: 24, 25, 26; or HCDR1, HCDR2, HCDR3 comprises SEQ ID NOs: 41, 42, 43, and LCDR1, LCDR2, LCDR3 comprises SEQ ID NOs: 44, 45, 46; or HCDR1, HCDR2, HCDR3 comprises SEQ ID NOs: 61, 62, 63, and LCDR1, LCDR2, LCDR3 comprises SEQ ID NOs: 64, 65, 66.

The invention also relates to an antibody or antigen binding fragment having HCDR1, HCDR2, and HCDR3 of the variable heavy chain of SEQ ID NO: 13, 33, 53 or 73, and the LCDR1, LCDR2 and LCDR3 of the variable light chain of SEQ ID NO: 14, 34, 54 or 74, as defined by Chothia. In another aspect of the invention the antibody or antigen binding fragment may have the HCDR1, HCDR2, and HCDR3 of the heavy chain variable domain sequence of SEQ ID NO: 13, 33, 53 or 73, and the LCDR1, LCDR2 and LCDR3 of the light chain variable domain sequence of SEQ ID NO: 14, 34, 54 or 74, as defined by Kabat.

In one aspect of the invention the isolated antibody or antigen binding fragment thereof includes a heavy chain variable domain (VH) sequence selected from the group consisting of SEQ ID NOs: 13, 33, 53 and 73. The isolated antibody or antigen binding fragment further can comprise a light chain variable domain (VL) sequence wherein the heavy chain variable domain and light chain variable domain combine to form an antigen binding site for Epo. In particular the light chain variable domain sequence can be selected from SEQ ID NOs: 14, 34, 54 and 74 wherein said isolated antibody or antigen binding fragment thereof binds Epo.

The invention also relates to an isolated antibody or antigen binding fragment thereof that includes a light chain variable domain sequence selected from the group consisting of SEQ ID NOs: 14, 34, 54 and 74, wherein said isolated antibody or antigen binding fragment thereof binds to human Epo. The isolated antibody or antigen binding fragment may further comprise a heavy chain variable domain sequence wherein the light chain variable domain and heavy chain variable domain combine to form and antigen binding site for Epo.

In particular, the isolated antibody or antigen binding fragment thereof that binds Epo, may have heavy and light chain variable domains comprising the sequences of SEQ ID NOs: 13 and 14; 33 and 34; 53 and 54; or 73 and 74, respectively.

The invention further relates to an isolated antibody or antigen binding fragment thereof, that includes a heavy chain variable domain having at least 80%, 85%, 90%, 95%, 96%, 97%, 98% or 99% sequence identity to a sequence selected from the group consisting of SEQ ID NOs:13, 33, 53, and 73, wherein said antibody binds to Epo. In one aspect, the isolated antibody or antigen binding fragment thereof also includes a light chain variable domain having at least 80%, 85%, 90%, 95%, 96%, 97%, 98% or 99% sequence identity to a sequence selected from the group consisting of SEQ ID NOs: 14, 34, 54, and 74. In a further aspect of the invention, the isolated antibody or antigen binding fragment has an HCDR1, HCDR2, HCDR3, LCDR1, LCDR2 and LCDR3 as defined by Kabat and as described in Table 1. It is also contemplated that the HCDR1, HCDR2, HCDR3, LCDR1, LCDR2 and LCDR3 may be defined by Chothia and as described in Table 1.

The invention also relates to an isolated antibody or antigen binding fragment thereof, having a light chain variable domain having at least 80%, 85%, 90%, 95%, 96%, 97%, 98% or 99% sequence identity to a sequence selected from the group consisting of SEQ ID NOs: 14, 34, 54, and 74, wherein said antibody binds Epo.

In another aspect of the invention, the isolated antibody, or antigen binding fragment thereof, that binds to Epo may have a heavy chain comprising the sequence of SEQ ID NO: 15, 35, 55, or 75. The isolated antibody can also include a light chain that can combine with the heavy chain to form an antigen binding site to human Epo. In particular, the light chain may have a sequence comprising SEQ ID NO: 16, 36, 56, or 76. In particular, the isolated antibody or antigen binding fragment thereof that binds Epo, may have a heavy chain and a light chain comprising the sequences of SEQ ID NOs: 15 and 16; 35 and 36; 55 and 56; or 75 and 76, respectively.

The invention still further relates to an isolated antibody or antigen binding fragment thereof that includes a heavy chain having at least 80%, 85%, 90%, 95%, 96%, 97%, 98% or 99% sequence identity to a sequence selected from the group consisting of SEQ ID NOs: 15, 35, 55, and 75, wherein said antibody binds to Epo. In one aspect, the isolated antibody or antigen binding fragment thereof also includes a light chain having at least 80%, 85%, 90%, 95%, 96%, 97%, 98% or 99% sequence identity to a sequence selected from the group consisting of SEQ ID NOs 16, 36, 56, and 76.

The invention still further relates to an isolated antibody or antigen binding fragment thereof that includes a light chain having at least 80%, 85%, 90%, 95%, 96%, 97%, 98% or 99% sequence identity to a sequence selected from the group consisting of SEQ ID NOs 16, 36, 56, and 76, wherein said antibody binds Epo.

The invention also relates to compositions comprising the isolated antibody, or antigen binding fragment thereof, as described herein. As well as, antibody compositions in combination with a pharmaceutically acceptable carrier. Specifically, the invention further includes pharmaceutical compositions comprising an antibody or antigen binding fragment thereof of Table 1, such as, for example antibody NVS1, NVS2, NVS3 or NVS4. The invention also relates to pharmaceutical compositions comprising a combination of two or more of the isolated antibodies or antigen binding fragments thereof of Table 1.

The invention also relates to an isolated nucleic acid sequence encoding the variable heavy chain having a sequence selected from SEQ ID NO: 13, 33, 53 and 73. In particular the nucleic acid has a sequence at least 80%, 85%, 90%, 95%, 96%, 97%, 98% or 99% sequence identity to a sequence selected from the group consisting of SEQ ID NOs: 17, 37, 57, and 77. In a further aspect of the invention the sequence is SEQ ID NOs: 17, 37, 57, or 77.

The invention also relates to an isolated nucleic acid sequence encoding the variable light chain having a sequence selected from SEQ ID NO: 14, 34, 54 and 74. In particular the nucleic acid has a sequence at least 80%, 85%, 90%, 95%, 96%, 97%, 98% or 99% sequence identity to a sequence selected from the group consisting of SEQ ID NOs: 18, 38, 58, and 78. In a further aspect of the invention the sequence is SEQ ID NOs: 18, 38, 58, or 78.

The invention also relates to an isolated nucleic acid comprising a sequence encoding a polypeptide that includes a light chain variable domain having at least 80%, 85%, 90%, 95%, 96%, 97%, 98% or 99% sequence identity to a sequence selected from the group consisting of SEQ ID NOs: 18, 38, 58, and 78.

The invention also relates to a vector that includes one or more of the nucleic acid molecules described herein.

The invention also relates to an isolated host cell that includes one or more of the nucleic acid molecules or vectors described herein. The invention also relates to an isolated host cell that includes a recombinant DNA sequence encoding a heavy chain of the antibody described above, and a second recombinant DNA sequence encoding a light chain of the antibody described above, wherein said DNA sequences are operably linked to a promoter and are capable of being expressed in the host cell. It is contemplated that the antibody can be a human monoclonal antibody. It is also contemplated that the host cell is a non-human mammalian cell, for example a CHO cell.

The invention also relates to a method of inhibiting Epo-dependent cell proliferation wherein the method includes the step of contacting Epo (e.g., contacting Epo in a subject) with an effective amount of a composition comprising the isolated antibody or antigen binding fragments thereof described herein; in particular, the composition can comprise the antibody NVS1, NVS2, NVS3, or NVS4. In one aspect, the method comprises contacting a cell (e.g., a cell comprising Epo) with a composition comprising the isolated antibody or antigen binding fragment thereof as described herein. The invention also relates to a composition comprising an isolated antibody or antigen binding fragment thereof as described herein for use to inhibit Epo-dependent cell proliferation in a subject. It is contemplated that the cell is a human cell. It is further contemplated that the cell is in a subject. It is also contemplated that the cell is in the eye of the subject. It is still further contemplated that the subject is human.

The invention also relates to a method of inhibiting Epo-dependent cell signalling wherein the method includes the step of contacting Epo with an effective amount of a composition comprising the isolated antibody or antigen binding fragments thereof described herein to prevent Epo from interacting with a receptor on a cell surface. In one aspect, the method comprises contacting a cell comprising Epo with a composition comprising the isolated antibody or antigen binding fragment thereof as described herein. The invention also relates to a composition comprising an isolated antibody or antigen binding fragment thereof as described herein for use to inhibit Epo-dependent cell signalling in a subject. It is contemplated that the cell is a human cell. It is further contemplated that the cell is in a subject. It is also contemplated that the cell is in the eye of the subject. It is still further contemplated that the subject is human.

The invention also relates to a method of inhibiting Epo-dependent cell proliferation or signalling wherein the method includes the step of contacting Epo with an effective amount of a composition comprising the isolated antibody or antigen binding fragments thereof described herein to prevent Epo from interacting with a receptor on a cell surface. It is contemplated that the cell is a B cell. It is contemplated that the cell is a human cell.

The invention also relates to a method of inhibiting Epo binding to the Epo receptor wherein the method includes the step of contacting Epo (e.g., contacting Epo in a subject) with an effective amount of a composition comprising the isolated antibody or antigen binding fragments thereof described herein; in particular, the composition can comprise the antibody NVS1, NVS2, NVS3, or NVS4. The invention also relates to a composition comprising an isolated antibody or antigen binding fragment thereof as described herein for use to inhibit Epo binding to the Epo receptor on a cell of a subject; in particular, the composition can comprise the antibody NVS1, NVS2, NVS3, or NVS4. It is contemplated that the cell is a human cell. It is further contemplated that the cell is in a subject. It is also contemplated that the cell is in the eye of the subject. It is still further contemplated that the subject is human.

The invention still further relates to a method of inhibiting Epo binding to a cell wherein the method includes the step of contacting Epo (e.g., in a subject) with an effective amount of a composition comprising the isolated antibody or antigen binding fragments thereof described herein; in particular, the composition can comprise the antibody NVS1, NVS2, NVS3, or NVS4. In one aspect, the method comprises contacting a cell (e.g., a cell comprising Epo) with a composition comprising the isolated antibody or antigen binding fragment thereof as described herein. The invention still further relates to a composition comprising an isolated antibody or antigen binding fragment thereof as described herein for use to inhibit Epo binding to a cell in a subject.

In one aspect, it is contemplated that the cell is a human cell. It is further contemplated that the cell is in a subject. It is also contemplated that the cell is in the eye of the subject. It is still further contemplated that the subject is human.

The invention also relates to a method of treating macular edema in a subject, wherein the method includes the step of administering to the subject an effective amount of a composition comprising the antibody or antigen binding fragments thereof described herein; in particular, the composition can comprise the antibody NVS1, NVS2, NVS3, or NVS4. The invention also relates to a composition comprising an antibody or antigen binding fragment thereof as described herein to treat macular edema in a subject. In one aspect, macular edema is associated with retinal vascular disease. It is contemplated that the retinal vascular disease associated with the macular edema can include diabetic retinopathy, diabetic macular edema, proliferative diabetic retinopathy, non-proliferative diabetic retinopathy, age-related macular degeneration, retinal vein occlusion, multifocal choroiditis, myopic choroidal neovascularization, or retinopathy of prematurity. It is also contemplated that the subject is human.

The invention also relates to a method of treating a condition or disorder associated with retinal vascular disease in a subject, wherein the method includes the step of administering to the subject an effective amount of a composition comprising the antibody or antigen binding fragments thereof described herein; in particular, the composition can comprise the antibody NVS1, NVS2, NVS3, or NVS4. The invention also relates to a composition comprising an antibody or antigen binding fragment thereof as described herein to treat a condition or disorder associated with retinal vascular disease in a subject. In one aspect, it is contemplated that the condition or disorder associated with retinal vascular disease is diabetic retinopathy. In another aspect, it is contemplated that the condition or disorder is age-related macular degeneration. It is still further contemplated that the condition or disorder associated with retinal vascular disease can be retinal vein occlusion, multifocal choroiditis, myopic choroidal neovascularization, or retinopathy of prematurity. It is also contemplated that the subject is human.

The invention also relates to a method of treating a condition or disorder associated with diabetic retinopathy in a subject, wherein the method includes the step of administering to the subject an effective amount of a composition comprising the antibody or antigen binding fragments thereof as described herein; in particular, the composition can comprise the antibody NVS1, NVS2, NVS3, or NVS4. The invention also relates to a composition comprising an antibody or antigen binding fragment thereof as described herein to treat a condition or disorder associated with diabetic retinopathy in a subject. It is contemplated that the subject is human.

The invention also relates to a method of treating a condition or disorder associated with macular edema in a subject, wherein the method includes the step of administering to the subject an effective amount of a composition comprising the antibody or antigen binding fragments thereof as described herein; in particular, the composition can comprise the antibody NVS1, NVS2, NVS3, or NVS4. The invention also relates to a composition comprising an antibody or antigen binding fragment thereof as described herein to treat a condition or disorder associated with macular edema in a subject. It is further contemplated that the condition or disorder associated with macular edema is diabetic macular edema. It is further contemplated that the subject is human.

The invention also relates to a method of treating proliferative diabetic retinopathy in a subject, wherein the method includes the step of administering to the subject an effective amount of a composition comprising the antibody or antigen binding fragments thereof described herein; in particular, the composition can comprise the antibody NVS1, NVS2, NVS3, or NVS4. The invention also relates to a composition comprising an antibody or antigen binding fragment thereof as described herein to treat proliferative diabetic retinopathy in a subject. It is further contemplated that the composition is administered to the eye of the subject wherein the composition decreases retinal vein dilation, decreases vascular leakage and/or increases blood flow in the eye. It is further contemplated that the subject is human.

Any of the foregoing isolated antibodies or antigen binding fragments thereof may be a monoclonal antibody or antigen binding fragment thereof.

Definitions

Unless defined otherwise, all technical and scientific terms used herein have the same meaning as commonly understood by those of ordinary skill in the art to which this invention pertains.

The term "antibody" as used herein means a whole antibody and any antigen binding fragment (i.e., "antigen-binding portion") or single chain thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen binding portion" or "antigen binding fragment" of an antibody, as used herein, refers to one or more fragments of an intact antibody that retain the ability to specifically bind to a given antigen (e.g., Erythropoietin: Epo). Antigen binding functions of an antibody can be performed by fragments of an intact antibody. Examples of binding fragments encompassed within the term antigen binding portion or antigen binding fragment of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain or a VL domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen binding portions or fragments of an antibody. These antibody fragments are obtained using conventional techniques known to those of skill in the art, and the fragments are screened for utility in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen binding fragment thereof (e.g.: a Fab fragment) generally refers to an antibody, or antigen binding fragment, having a KD of $10^{-9}$M or less.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

The phrase "specifically (or selectively) binds" to an antibody (e.g., an Epo-binding antibody) refers to a binding reaction that is determinative of the presence of a cognate antigen (e.g., a human Epo or cynomolgus Epo) in a heterogeneous population of proteins and other biologics. The phrases "an antibody recognizing an antigen" and "an antibody specific for an antigen" are used interchangeably herein with the term "an antibody which binds specifically to an antigen".

The term "condition or disorder associated with retinal vascular disease" refers to conditions, disorders or diseases in which the retina degenerates or becomes dysfunctional. This includes diabetic retinopathy (DR), diabetic macular edema (DME), proliferative diabetic retinopathy (PDR), non-proliferative diabetic retinopathy (NPDR), age-related macular degeneration (AMD), retinal vein occlusion (RVO), multifocal choroiditis, myopic choroidal neovascularization, or retinopathy of prematurity. Anatomic characteristics of retinal vascular disease that may be treated by Epo inhibition include macular edema, venous dilation, vessel tortuosity, vascular leakage as measured by fluorescein angiography, retinal hemorrhage, and microvascular anomalies (e.g. microaneurysm, cotton-wool spots, IRMA), capillary dropout, leukocyte adhesion, retinal ischemia, neovascularization of the optic disk, neovascularization of the posterior pole, iris neovascularization, intraretinal hemorrhage, vitreous hemorrhage, macular scar, subretinal fibrosis, and retinal fibrosis.

The term "condition or disorder associated with diabetic retinopathy" refers to conditions in which the retina degenerates or becomes dysfunctional, as a consequence of effects of diabetes mellitus (Type 1 or Type 2) on retinal vasculature, retinal metabolism, retinal pigment epithelium, the blood-retinal barrier, or ocular levels of advanced glycation end products (AGEs), aldose reductase activity, glycosylated hemoglobin, and protein kinase C. Visual loss in patients with diabetic retinopathy can be a result of retinal ischemia, macular edema, vascular leakage, vitreous hemorrhage, or direct effects of elevated glucose levels on retinal neurons. Anatomic characteristics of diabetic retinopathy that may be treated by Epo inhibition include microaneurysm, cotton wool spots, venous dilation, macular edema, intra-retinal microvascular abnormalities (IRMA), intra-retinal hemorrhage, vascular proliferation, neovascularization of the disk, rubeosis, and retinal ischemia. "Diabetic macular edema" occurs in a subject with diabetic retinopathy and can occur at any stage of the disease.

The term "condition or disorder associated with macular edema", refers to conditions or disorders in which swelling or thickening of the macula occurs as a result of retinal blood vessels leaking fluid, "macular edema". Macular edema occurs in, and is often a complication of, retinal vascular disease. Specific conditions or disorders associated with macular edema include, diabetic retinopathy, diabetic macular edema, proliferative diabetic retinopathy, non-proliferative diabetic retinopathy, age-related macular degeneration, retinal vein occlusion, multifocal choroiditis, myopic choroidal neovascularization, or retinopathy of prematurity. Treatment of macular edema by the inhibition of Epo can be determined by funduscopic examination, optical coherence tomography, and improved visual acuity.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The terms "Epo protein" or "Epo antigen" or "EPO" or "Epo" are used interchangeably, and refer to the erythropoietin protein in different species. For example, human Epo has the sequence as set out in Table 1: SEQ ID NO: 81. Examples of Epo proteins from other species are provided in Table 1, SEQ ID NOs: 82, 83, 84 or 85. The protein sequences for human, cynomolgus, mouse, rat, and rabbit Epo are publicly available and described in Table 1. Human Epo can also be hyperglycosylated. Hyperglycosylated Epo is also know in the art as "darbepoietin" and can be obtained from various sources including, LEK Pharmaceuticals.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are produced by hybridomas which include (i) a B cell obtained from a transgenic non-human animal, e.g., a transgenic mouse, having a genome comprising a human heavy chain transgene and a light chain transgene (ii) fused to an immortalized cell.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766,886.

The terms "identical" or 100% percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "inhibit (or inhibits) Epo-dependent cell proliferation" refers to the ability of an anti-Epo antibody to interfere with cell activation (e.g., cell signaling), replication and/or proliferation stimulated and/or induced by Epo. Specifically, "inhibit" refers to a statistically significant decrease (i.e., $p<0.05$) in Epo-dependent cell proliferation, or other parameter (e.g., Epo dependent cell signaling, angiogenesis), in a subject following contact with an anti-Epo antibody or fragment thereof as described herein relative to a control. As used herein, "inhibit (or inhibits) Epo-dependent cell proliferation" can also refer to a clinically relevant improvement in visual function or retinal anatomy following treatment with an anti-Epo antibody described herein in a patient diagnosed with a condition or disorder associated with retinal vascular disease as described below.

As used herein, "inhibit (or inhibits) Epo dependent cell signaling" refers to the ability of an anti-Epo antibody described herein to produce a statistically significant (i.e., $p<0.05$) decrease in the activation of the intracellular signaling pathways stimulated or induced by Epo.

The term "isolated antibody" refers to an antibody that is substantially free of other antibodies having different antigenic specificities (e.g., an isolated antibody that specifically binds Epo is substantially free of antibodies that specifically bind antigens other than Epo). An isolated antibody that specifically binds Epo may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors. Isotype also refers to the antibody class (e.g., kappa, lambda) that is provided by the light-chain constant regions.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of Kd to Ka (i.e. Kd/Ka) and is expressed as a molar concentration (M). $K_D$ values for antibodies can be determined using methods well established in the art. Methods for determining the $K_D$ of an antibody include measuring surface plasmon resonance using a biosensor system such as a Biacore® system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g.: mammals and non-mammals) such as, non-human primates (e.g.: cynomolgus monkey), sheep, dog, cow, chickens, amphibians, and reptiles. Except when noted, the terms "patient" or "subject" are used herein interchangeably. As used herein, the terms "cyno" or "cynomolgus" refer to the cynomolgus monkey (Macaca fascicularis).

As used herein, the term "treating" or "treatment" of any disease or disorder (e.g., retinal vascular disease, diabetic retinopathy, macular edema) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder. "Prevention" as it relates to indications described herein, including, conditions or disorders associated with retinal vascular disease, conditions or disorders associated with diabetic retinopathy, and/or conditions or disorders associated with macular edema, means any action that prevents or slows a worsening in visual function, retinal anatomy, retinal vascular disease parameter, diabetic retinopathy disease parameter, and/or macular edema disease parameter, as described below, in a patient at risk for said worsening. More specifically, "treatment" of conditions or disorders associated with retinal vascular disease, conditions or disorders associated with diabetic retinopathy, and/or conditions or disorders associated with macular edema means any action that results in, or is contemplated to result in, the improvement or preservation of visual function and/or retinal anatomy. Methods for assessing treatment and/or prevention of disease are known in the art and described herein below.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

DETAILED DESCRIPTION

Figure 1:
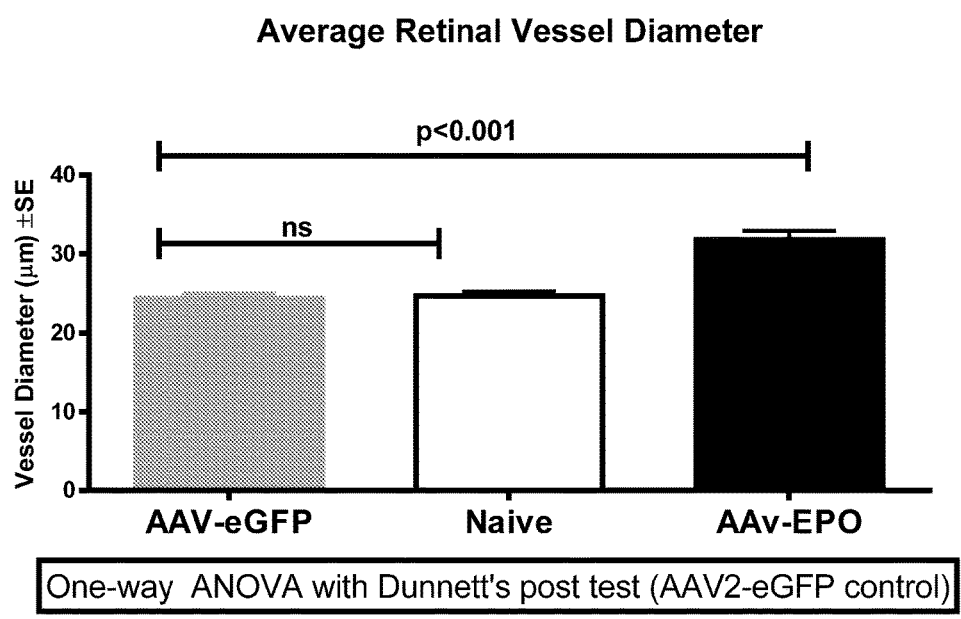
FIG. 1. Shows that EPO induces vessel dilation in the central retina.

The present invention is based, in part, on the discovery of antibody molecules that specifically bind to Epo. The invention relates to both full IgG format antibodies as well as antigen binding fragments thereof, such as Fab fragments (e.g., see antibodies NVS1, NVS2, NVS3 and NVS4).

Accordingly, the present invention provides antibodies that specifically bind to Epo (e.g., human Epo, cynomolgus Epo, rat Epo, and mouse Epo), pharmaceutical compositions, production methods, and methods of use of such antibodies and compositions.

Epo Antibodies & Antigen Binding Fragments

The present invention provides antibodies that specifically bind to Epo. In some embodiments, the present invention provides antibodies that specifically bind to human, cynomolgus, rat and/or mouse Epo, as well as human-hyperglycosylated Epo (darbepoietin). Antibodies of the invention include, but are not limited to, the human monoclonal antibodies and Fabs, isolated as described in the Examples.

The present invention provides antibodies that specifically bind an Epo protein (e.g., human, cynomolgus, rat and/or mouse Epo), wherein the antibodies comprise a VH domain having an amino acid sequence of SEQ ID NO: 13, 33, 53 or 73. The present invention also provides antibodies that specifically bind to an Epo protein, wherein the antibodies comprise a VH CDR having an amino acid sequence of any one of the VH CDRs listed in Table 1, infra. In particular, the invention provides antibodies that specifically bind to an Epo protein (e.g., human, cynomolgus, rat and/or mouse Epo), wherein the antibodies comprise (or alternatively, consist of) one, two, three, or more VH CDRs having an amino acid sequence of any of the VH CDRs listed in Table 1, infra.

The present invention provides antibodies that specifically bind to an Epo protein, said antibodies comprising a VL domain having an amino acid sequence of SEQ ID NO:14, 34, 54 or 74. The present invention also provides antibodies that specifically bind to an Epo protein (e.g., human, cynomolgus, rat and/or mouse Epo), said antibodies comprising a VL CDR having an amino acid sequence of any one of the VL CDRs listed in Table 1, infra. In particular, the invention provides antibodies that specifically bind to an Epo protein (e.g., human, cynomolgus, rat and/or mouse Epo), said antibodies comprising (or alternatively, consisting of) one, two, three or more VL CDRs having an amino acid sequence of any of the VL CDRs listed in Table 1, infra.

Other antibodies of the invention include amino acids that have been mutated, yet have at least 80, 85, 90, 95, 96, 97, 98, or 99 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode VH, VL, the full length heavy chain, and the full length light chain of the antibodies that specifically bind to an Epo protein (e.g., human, cynomolgus, rat and/or mouse Epo). Such nucleic acid sequences can be optimized for expression in mammalian cells (for example, Table 1 shows the optimized nucleic acid sequences for the heavy chain and light chain of antibodies of the invention).

TABLE 1

Examples of Epo Antibodies, Fabs and Epo Proteins

| Amino acid sequence or polynucleotide (PN) | Sequence Identifier (SEQ.I.D.NO:) and sequence |
|---|---|
| NVS1 | |
| CDRH1 Kabat | 1 SYAIS |
| CDRH2 Kabat | 2 GIDPISGFADYAQKFQG |
| CDRH3 Kabat | 3 ELYYPGTWMAVMAY |
| CDRL1 Kabat | 4 SGDNIPEYYVH |
| CDRL2 Kabat | 5 RDNERPS |
| CDRL3 Kabat | 6 QVFDESSWHWV |
| CDRH1 Chothia | 7 GGTFRSY |
| CDRH2 Chothia | 8 DPISGF |
| CDRH3 Chothia | 9 ELYYPGTWMAVMAY |
| CDRL1 Chothia | 10 DNIPEYY |
| CDRL2 Chothia | 11 RDN |
| CDRL3 Chothia | 12 FDESSWHW |
| VH | 13 QVQLVQSGAEVKKPGSSVKVSCKASGGTFRSYAISWVRQAPGQGLEWMGGID PISGFADYAQKFQGRVTITADESTSTAYMELSSLRSEDTAVYYCARELYYPG TWMAVMAYWGRGTLVTVSS |
| VL | 14 SYVLTQPPSVSVAPGKTARITCSGDNIPEYYVHWYQQKPGQAPVLVIYRDNE RPSGIPERFSGSNSGNTATLTISRVEAGDEADYYCQVFDESSWHWVFGGGTK LTVL |
| Heavy chain | 15 QVQLVQSGAEVKKPGSSVKVSCKASGGTFRSYAISWVRQAPGQGLEWMGGID PISGFADYAQKFQGRVTITADESTSTAYMELSSLRSEDTAVYYCARELYYPG TWMAVMAYWGRGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKRVEPKSC |
| Light chain | 16 SYVLTQPPSVSVAPGKTARITCSGDNIPEYYVHWYQQKPGQAPVLVIYRDNE RPSGIPERFSGSNSGNTATLTISRVEAGDEADYYCQVFDESSWHWVFGGGTK LTVLGQPKAAPSVTLFPPSSEELQANKATLVCLISDFYPGAVTVAWKADSSP VKAGVETTTPSKQSNNKYAASSYLSLTPEQWKSHRSYSCQVTHEGSTVEKTV APTECS |
| PN encoding SEQ.I.D.NO: 13 | 17 caggtgcagctggtgcagtcaggcgccgaagtgaagaaaccggctctagcg tgaaggtgtcctgtaaagctagtggcggcacctttagatcctacgctattag ctgggtgcgacaggctccaggccagggcctcgaatggatgggcggcatcgac cctattagcggcttcgccgactacgctcagaaatttcagggcagagtgacta tcaccgccgacgagtctactagcaccgcctacatggaactgtctagcctgag atcagaggacaccgccgtgtactactgcgctagagagctgtactaccccggc acctggatggccgtgatggcctattggggcagaggcaccctggtgacagtgt cttct |
| PN encoding SEQ.I.D.NO: 14 | 18 agctacgtgctgacccagccccctagcgtgtcagtggcccctggcaagaccg ctagaatcacctgtagcggcgataacatccccgagtactacgtgcactggta tcagcagaagcccggccaggccccgtgctggtgatctatagagataacgag cggcctagcggcatccccgagcggttttccggctctaatagcggcaacaccg ctaccctgactattttcaagagtggaagccggcgacgaggccgactactactg tcaggtgttcgacgagtcttcatggcactgggtgttcggcggaggcaccaag ctgaccgtgctg |
| PN encoding SEQ.I.D.NO: 15 | 19 caggtgcagctggtgcagtcaggcgccgaagtgaagaaaccggctctagcg tgaaggtgtcctgtaaagctagtggcggcacctttagatcctacgctattag ctgggtgcgacaggctccaggccagggcctcgaatggatgggcggcatcgac cctattagcggcttcgccgactacgctcagaaatttcagggcagagtgacta |

TABLE 1-continued

Examples of Epo Antibodies, Fabs and Epo Proteins

| Amino acid sequence or polynucleotide (PN) | Sequence Identifier (SEQ.I.D.NO:) and sequence |
|---|---|
| | tcaccgccgacgagtctactagcaccgcctacatggaactgtctagcctgag<br>atcagaggacaccgccgtgtactactgcgctagagagctgtactaccccggc<br>acctggatggccgtgatggcctattggggcagaggcaccctggtgacagtgt<br>cttctgctagcactaagggccctccgtgttccctggccccttccagcaa<br>gtctacctctggcggcaccgctgctctgggctgcctggtgaaggactacttc<br>cctgagcctgtgacagtgtcctggaactctggcgccctgacctccggcgtgc<br>acaccttccctgccgtgctgcagtcctccggcctgtactccctgtcctccgt<br>ggtgacagtgccttcctccagcctgggcacccagacctatatctgcaacgtg<br>aaccacaagccttccaacaccaaggtggacaagcgggtggagcctaagtcat<br>gc |
| PN encoding SEQ.I.D.NO: 16 | 20<br>agctacgtgctgacccagccccctagcgtgtcagtggcccctggcaagaccg<br>ctagaatcacctgtagcggcgataacatccccgagtactacgtgcactggta<br>tcagcagaagcccggccaggcccccgtgctggtgatctatagagataacgag<br>cggcctagcggcatccccgagcggttttccggctctaatagcggcaacaccg<br>ctaccctgactatttcaagagtggaagccggcgacgaggccgactactactg<br>tcaggtgttcgacgagtcttcatggcactgggtgttcggcggaggcaccaag<br>ctgaccgtgctgggccagcctaaggctgcccccagcgtgaccctgttccccc<br>ccagcagcgaggagctgcaggccaacaaggccaccctggtgcctgatcag<br>cgacttctacccaggcgccgtgaccgtggcctggaaggccgacagcagcccc<br>gtgaaggccggcgtggagaccaccacccccagcaagcagagcaacaacaagt<br>acgccgccagcagctacctgagcctgacccccgagcagtggaagagccacag<br>gtcctacagctgccaggtgacccacgagggcagcaccgtggaaaagaccgtg<br>gccccaaccgagtgcagc |
| NVS2<br>CDRH1_Kabat | 21 SYWIG |
| CDRH2_Kabat | 22 WIDPYRSEIRYSPSFQG |
| CDRH3_Kabat | 23 VSSEPFDS |
| CDRL1_Kabat | 24 SGDKLGDHYAY |
| CDRL2_Kabat | 25 DDSKRPS |
| CDRL3_Kabat | 26 ATWTFEGDYV |
| CDRH1 Chothia | 27 GYSFTSY |
| CDRH2 Chothia | 28 DPYRSE |
| CDRH3 Chothia | 29 VSSEPFDS |
| CDRL1 Chothia | 30 DKLGDHY |
| CDRL2 Chothia | 31 DDS |
| CDRL3 Chothia | 32 WTFEGDY |
| VH | 33<br>EVQLVQSGAEVKKPGESLKISCKGSGYSFTSYWIGWVRQMPGKGLEWMGWID<br>PYRSEIRYSPSFQGQVTISADKSISTAYLQWSSLKASDTAMYYCARVSSEPF<br>DSWGQGTLVTVSS |
| VL | 34<br>SYVLTQPPSVSVAPGKTARITCSGDKLGDHYAYWYQQKPGQAPVLVIYDDSK<br>RPSGIPERFSGSNSGNTATLTISRVEAGDEADYYCATWTFEGDYVFGGGTKL<br>TVL |
| Heavy chain | 35<br>EVQLVQSGAEVKKPGESLKISCKGSGYSFTSYWIGWVRQMPGKGLEWMGWID<br>PYRSEIRYSPSFQGQVTISADKSISTAYLQWSSLKASDTAMYYCARVSSEPF<br>DSWGQGTLVTVSSASTKGPSVFPLAPSSKSTSGGTAALGCLVKDYFPEPVTV<br>SWNSGALTSGVHTFPAVLQSSGLYSLSSVVTVPSSSLGTQTYICNVNHKPSN<br>TKVDKRVEPKSC |

TABLE 1-continued

Examples of Epo Antibodies, Fabs and Epo Proteins

| Amino acid sequence or polynucleotide (PN) | Sequence Identifier (SEQ.I.D.NO:) and sequence |
|---|---|
| Light chain | 36<br>SYVLTQPPSVSVAPGKTARITCSGDKLGDHYAYWYQQKPGQAPVLVIYDDSK<br>RPSGIPERFSGSNSGNTATLTISRVEAGDEADYYCATWTFEGDYVFGGGTKL<br>TVLGQPKAAPSVTLFPPSSEELQANKATLVCLISDFYPGAVTVAWKADSSPV<br>KAGVETTTPSKQSNNKYAASSYLSLTPEQWKSHRSYSCQVTHEGSTVEKTVA<br>PTECS |
| PN encoding SEQ.I.D.No: 33 | 37<br>Gaggtgcagctggtgcagtcaggcgccgaagtgaagaagcccggcgagtcac<br>tgaagattagctgtaaaggctcaggctatagcttcactagctactggatcgg<br>ctgggtgcgacagatgcccggcaagggcctggaatggatgggctggatcgac<br>ccctatagatcagagattaggtatagccctagctttcagggccaggtgacaa<br>ttagcgccgataagtctattagcaccgcctacctgcagtggtctagcctgaa<br>ggctagtgacaccgctatgtactactgcgctagagtgtctagcgagcccttc<br>gatagctggggccagggcaccctggtgacagtgtcttca |
| PN encoding SEQ.I.D.NO: 34 | 38<br>agctacgtgctgacccagccccctagcgtgtcagtggcccctggcaagaccg<br>ctagaatcacctgtagcggcgataagctgggcgatcactacgcctactggta<br>tcagcagaagcccggccaggcccccgtgctggtgatctacgacgactctaag<br>cggcctagcggcatccccgagcggtttagcggctctaatagcggcaacaccg<br>ctaccctgactatttcaagagtggaagccggcgacgaggccgactactactg<br>cgctacctggaccttcgagggcgactacgtgttcggcggaggcactaagctg<br>accgtgctg |
| PN encoding SEQ.I.D.NO: 35 | 39<br>gaggtgcagctggtgcagtcaggcgccgaagtgaagaagcccggcgagtcac<br>tgaagattagctgtaaaggctcaggctatagcttcactagctactggatcgg<br>ctgggtgcgacagatgcccggcaagggcctggaatggatgggctggatcgac<br>ccctatagatcagagattaggtatagccctagctttcagggccaggtgacaa<br>ttagcgccgataagtctattagcaccgcctacctgcagtggtctagcctgaa<br>ggctagtgacaccgctatgtactactgcgctagagtgtctagcgagcccttc<br>gatagctggggccagggcaccctggtgacagtgtcttcagctagcactaagg<br>gcccctccgtgttccctctggcccttccagcaagtctacctctggcggcac<br>cgctgctctgggctgcctggtgaaggactacttccctgagcctgtgacagtg<br>tcctggaactctggcgccctgacctccggcgtgcacaccttccctgccgtgc<br>tgcagtcctccggcctgtactcctgtcctccgtggtgacagtgccttcctc<br>cagcctgggcacccagacctatatctgcaacgtgaaccacaagccttccaac<br>accaaggtggacaagcgggtggagcctaagtcatgc |
| PN encoding SEQ.I.D.NO: 36 | 40<br>agctacgtgctgacccagccccctagcgtgtcagtggcccctggcaagaccg<br>ctagaatcacctgtagcggcgataagctgggcgatcactacgcctactggta<br>tcagcagaagcccggccaggcccccgtgctggtgatctacgacgactctaag<br>cggcctagcggcatccccgagcggtttagcggctctaatagcggcaacaccg<br>ctaccctgactatttcaagagtggaagccggcgacgaggccgactactactg<br>cgctacctggaccttcgagggcgactacgtgttcggcggaggcactaagctg<br>accgtgctgggccagcctaaggctgccccccagcgtgaccctgttcccccca<br>gcagcgaggagctgcaggccaacaaggccaccctggtgtgcctgatcagcga<br>cttctacccaggcgccgtgaccgtggcctggaaggccgacagcagccccgtg<br>aaggccggcgtggagaccaccacccccagcaagcagagcaacaacaagtacg<br>ccgccagcagctacctgagcctgacccccgagcagtggaagagccacaggtc<br>ctacagctgccaggtgacccacgagggcagcaccgtggaaaagaccgtggcc<br>ccaaccgagtgcagc |
| NVS3<br>CDRL1_Kabat | 41 SNTAAWN |
| CDRL2_Kabat | 42 VIYYRSKWYNDYAVSVKS |
| CDRL3_Kabat | 43 SVPGGDPGLEHAFAY |
| CDRL1_Kabat | 44 SGDNLGTYYVE |
| CDRL2_Kabat | 45 DDSDRPS |
| CDRL3_Kabat | 46 ASFASWSDSV |
| CDRH1 Chothia | 47 GDSVSSNTA |
| CDRH2 Chothia | 48 YYRSKWY |
| CDRH3 Chothia | 49 SVPGGDPGLEHAFAY |

TABLE 1-continued

Examples of Epo Antibodies, Fabs and Epo Proteins

| Amino acid sequence or polynucleotide (PN) | Sequence Identifier (SEQ.I.D.NO:) and sequence |
|---|---|
| CDRL1 Chothia | 50 DNLGTYY |
| CDRL2 Chothia | 51 DDS |
| CDRL3 Chothia | 52 FASWSDS |
| VH | 53 QVQLQQSGPGLVKPSQTLSLTCAISGDSVSSNTAAWNWIRQSPSRGLEWLGV IYYRSKWYNDYAVSVKSRITINPDTSKNQFSLQLNSVTPEDTAVYYCARSVP GGDPGLEHAFAYWGRGTLVTVSS |
| VL | 54 SYVLTQPPSVSVAPGKTARITCSGDNLGTYYVEWYQQKPGQAPVLVIYDDSD RPSGIPERFSGSNSGNTATLTISRVEAGDEADYYCASFASWSDSVFGGGTKL TVL |
| Heavy chain | 55 QVQLQQSGPGLVKPSQTLSLTCAISGDSVSSNTAAWNWIRQSPSRGLEWLGV IYYRSKWYNDYAVSVKSRITINPDTSKNQFSLQLNSVTPEDTAVYYCARSVP GGDPGLEHAFAYWGRGTLVTVSSASTKGPSVFPLAPSSKSTSGGTAALGCLV KDYFPEPVTVSWNSGALTSGVHTFPAVLQSSGLYSLSSVVTVPSSSLGTQTY ICNVNHKPSNTKVDKRVEPKSC |
| Light chain | 56 SYVLTQPPSVSVAPGKTARITCSGDNLGTYYVEWYQQKPGQAPVLVIYDDSD RPSGIPERFSGSNSGNTATLTISRVEAGDEADYYCASFASWSDSVFGGGTKL TVLGQPKAAPSVTLFPPSSEELQANKATLVCLISDFYPGAVTVAWKADSSPV KAGVETTTPSKQSNNKYAASSYLSLTPEQWKSHRSYSCQVTHEGSTVEKTVA PTECS |
| PN encoding SEQ.I.D.NO: 53 | 57 Caggtgcagctgcagcagtcaggccctggcctggtgaaacctagtcagaccc tgagcctgacctgcgctattagcggcgatagcgtgtcatctaacaccgccgc ctggaactggattagacagtcacctagtagaggcctggaatggctgggcgtg atctactataggtctaagtggtacaacgactacgccgtgtcagtgaagtcta ggatcactattaaccccgacacctctaagaatcagttcagcctgcagctgaa tagcgtgaccccgaggacaccgccgtgtactactgcgctagatcagtgcct ggcggcgaccccggcctggaacacgcctttgcctactggggcagaggcaccc tggtgacagtgtcttct |
| PN encoding SEQ.I.D.NO: 54 | 58 agctacgtgctgacccagcccctagcgtgtcagtggccctggcaagaccg ctagaatcacctgtagcggcgataacctgggcacctactacgtggaatggta tcagcagaagcccggccaggccccgtgctggtgatctacgacgatagcgat agacctagcggcatccccgagcggtttagcggctctaatagcggcaacaccg ctaccctgactattagtagagtggaagccggcgacgaggccgactactactg cgctagtttcgctagttggagcgattcagtgttcggcggaggcactaagctg accgtgctg |
| PN encoding SEQ.I.D.NO: 55 | 59 caggtgcagctgcagcagtcaggccctggcctggtgaaacctagtcagaccc tgagcctgacctgcgctattagcggcgatagcgtgtcatctaacaccgccgc ctggaactggattagacagtcacctagtagaggcctggaatggctgggcgtg atctactataggtctaagtggtacaacgactacgccgtgtcagtgaagtcta ggatcactattaaccccgacacctctaagaatcagttcagcctgcagctgaa tagcgtgaccccgaggacaccgccgtgtactactgcgctagatcagtgcct ggcggcgaccccggcctggaacacgcctttgcctactggggcagaggcaccc tggtgacagtgtcttctgctagcactaagggccctccgtgttccctctggc ccttccagcaagtctacctctggcggcaccgctgctctgggctgcctggtg aaggactacttccctgagcctgtgacagtgtcctggaactctggcgccctga cctccggcgtgcacaccttccctgccgtgctgcagtcctccggcctgtactc cctgtcctccgtggtgacagtgccttcctccagcctgggcacccagacctat atctgcaacgtgaaccacaagccttccaacaccaaggtggacaagcgggtgg agcctaagtcatgc |
| PN encoding SEQ.I.D.NO: 56 | 60 agctacgtgctgacccagcccctagcgtgtcagtggccctggcaagaccg ctagaatcacctgtagcggcgataacctgggcacctactacgtggaatggta tcagcagaagcccggccaggccccgtgctggtgatctacgacgatagcgat agacctagcggcatccccgagcggtttagcggctctaatagcggcaacaccg ctaccctgactattagtagagtggaagccggcgacgaggccgactactactg cgctagtttcgctagttggagcgattcagtgttcggcggaggcactaagctg |

TABLE 1-continued

Examples of Epo Antibodies, Fabs and Epo Proteins

| Amino acid sequence or polynucleotide (PN) | Sequence Identifier (SEQ.I.D.NO:) and sequence |
|---|---|
| | accgtgctgggccagcctaaggctgcccccagcgtgaccctgttcccccca<br>gcagcgaggagctgcaggccaacaaggccaccctggtgtgcctgatcagcga<br>cttctacccaggcgccgtgaccgtggcctggaaggccgacagcagccccgtg<br>aaggccggcgtggagaccaccacccccagcaagcagagcaacaacaagtacg<br>ccgccagcagctacctgagcctgacccccgagcagtggaagagccacaggtc<br>ctacagctgccaggtgacccacgagggcagcaccgtggaaaagaccgtggcc<br>ccaaccgagtgcagc |

NVS4

| CDRH1_Kabat | 61 SYYMS |
|---|---|
| CDRH2_Kabat | 62 WINPLKGNTNYAQKFQG |
| CDRH3_Kabat | 63 EGMYFDI |
| CDRL1_Kabat | 64 SGDSIGDKYVY |
| CDRL2_Kabat | 65 DTNKRPS |
| CDRL3_Kabat | 66 QSWDLDFNTYV |
| CDRH1 Chothia | 67 GYTFTSY |
| CDRH2 Chothia | 68 NPLKGN |
| CDRH3 Chothia | 69 EGMYFDI |
| CDRL1 Chothia | 70 DSIGDKY |
| CDRL2 Chothia | 71 DTN |
| CDRL3 Chothia | 72 WDLDFNTY |
| VH | 73<br>QVQLVQSGAEVKKPGASVKVSCKASGYTFTSYYMSWVRQAPGQGLEWMGWIN<br>PLKGNTNYAQKFQGRVTMTRDTSISTAYMELSRLRSEDTAVYYCAREGMYFD<br>IWGQGTLVTVSS |
| VL | 74<br>SYELTQPLSVSVALGQTARITCSGDSIGDKYVYWYQQKPGQAPVLVIYDTNK<br>RPSGIPERFSGSNSGNTATLTISRAQAGDEADYYCQSWDLDFNTYVFGGGTK<br>LTVL |
| Heavy chain | 75<br>qvqlvqsgaevkkpgasvkvsckasgytftsyymswvrqapgqglewmgwin<br>plkgntnyaqkfqgrvtmtrdtsisraymelsrlrsedtavyycaregmyfd<br>iwgqgtlvtvssasrkgpsvfplapsskstsggtaalgclvkdyfpepvtvs<br>wnsgaltsgvhtfpavlqssglyslssvvtvpssslgtqryicnvnhkpsnt<br>kvdkrvepksc |
| Light Chain | 76<br>SYELTQPLSVSVALGQTARITCSGDSIGDKYVYWYQQKPGQAPVLVIYDTNK<br>RPSGIPERFSGSNSGNTATLTISRAQAGDEADYYCQSWDLDFNTYVFGGGTK<br>LTVLGQPKAAPSVTLFPPSSEELQANKATLVCLISDFYPGAVTVAWKADSSP<br>VKAGVETTTPSKQSNNKYAASSYLSLTPEQWKSHRSYSCQVTHEGSTVEKTV<br>APTECS |
| PN encoding<br>SEQ.I.D.NO: 73 | 77<br>caggtgcagctggtgcagtcaggcgccgaagtgaagaaacccggcgctagtg<br>tgaaggtgtcctgtaaagctagtggctacaccttcactagctactacatgag<br>ctgggtgcgacaggcccctggacagggcctggaatggatgggctggattaac<br>cccctgaagggcaacactaactacgcccagaaattccagggccgagtgacta<br>tgactagggacactagcattagcaccgcctacatggaactgtctaggctgag<br>atcagaggacaccgccgtgtactactgcgctagagaaggcatgtacttcgac<br>atctggggccagggcaccctggtgacagtgtcttct |

TABLE 1-continued

Examples of Epo Antibodies, Fabs and Epo Proteins

| Amino acid sequence or polynucleotide (PN) | Sequence Identifier (SEQ.I.D.NO:) and sequence |
|---|---|
| PN encoding SEQ.I.D.NO: 74 | 78<br>agctacgagctgactcagcccctgagcgtgtcagtggccctgggacagaccg<br>ctagaatcacctgtagcggcgactctatcggcgacaaatacgtgtactggta<br>tcagcagaagcccggccaggccccgtgctggtgatctacgacactaacaag<br>cggcctagcggcatccccgagcggtttagcggctctaatagcggcaacaccg<br>ctaccctgactattagtagggctcaggccggcgacgaggccgactactactg<br>tcagtcatgggaccrggacttcaacacctacgtgrtcggcggaggcactaag<br>ctgaccgtgctg |
| PN encoding SEQ.I.D.NO: 75 | 79<br>caggtgcagctggtgcagtcaggcgccgaagtgaagaaacccggcgctagtg<br>tgaaggtgtcctgtaaagctagtggctacaccttcactagctactacatgag<br>ctgggtgcgacaggcccctggacagggcctggaatggatgggctggattaac<br>ccctgaagggcaacactaactacgcccagaaatcccagggccgagtgacta<br>tgactagggacactagcattagcaccgcctacatggaactgtctaggctgag<br>atcagaggacaccgccgtgtactactgcgctagagaaggcatgtacttcgac<br>atctggggccagggcacccctggtgacagtgtcttctgctagcactaagggcc<br>cctccgtgttccctctggcccttccagcaagtctacctctggcggcaccgc<br>tgctctgggctgcctggtgaaggactacttccctgagcctgtgacagtgtcc<br>tggaactctggcgcccctgacctccggcgtgcacaccttccctgccgtgctgc<br>agtcctccggcctgtactccctgtcctccgtggtgacagtgccttcctccag<br>cctgggcacccagacctatatctgcaacgtgaaccacaagccttccaacacc<br>aaggtggacaagcgggtggagcctaagtcatgc |
| PN encoding SEQ.I.D.NO: 76 | 80<br>agctacgagctgactcagcccctgagcgtgtcagtggccctgggacagaccg<br>ctagaatcacctgtagcggcgactctatcggcgacaaatacgtgtactggta<br>tcagcagaagcccggccaggccccgtgctggtgatctacgacactaacaag<br>cggcctagcggcatccccgagcggtttagcggctctaatagcggcaacaccg<br>ctaccctgactattagtagggctcaggccggcgacgaggccgactactactg<br>tcagtcatgggacctggacttcaacacctacgtgttcggcggaggcactaag<br>ctgaccgtgctgggccagcctaaggctgccccagcgtgaccctgttccccc<br>ccagcagcgaggagctgcaggccaacaaggccaccctggtgtgcctgatcag<br>cgacttctacccaggcgccgtgaccgtggcctggaaggccgacagcagcccc<br>gtgaaggccggcgtggagaccaccaccccccagcaagcagagcaacaacaagt<br>acgccgccagcagctacctgagcctgacccccgagcagtggaagagccacag<br>gtcctacagctgccaggtgacccacgagggcagcaccgtggaaaagaccgtg<br>gccccaaccgagtgcagc |
| Human Epo NP_000790.2 | 81<br>apprlicdsrvleryllleakeaenittgcaehcslneniitvpdtkvnfyawk<br>rmevgqqavevwqglallseavlrgqallvnssqpweplqlhvdkavsglrs<br>lttllralgaqkeaisppdaasaaplrtitadtfrklfrvysnflrgklkly<br>tgeacrtgdr |
| Cynomolgus Epo Uniprot: P07865 | 82<br>apprlicdsrvleryllleakeaenvtmgcsescslneniitvpdtkvnfyawk<br>rmevgqqavevwqglallseavlrgqavlanssqpfeplqlhmdkaisglrs<br>ittllralgaqeaislpdaasaaplrtitadtfcklfrvysnflrgklklyt<br>geacrrgdr |
| Mouse Epo NP_031968.1 | 83<br>apprlicdsrvleryileakeaenvtmgcaegprlsenitvpdtkvnfyawk<br>rmeveecialevwqglsllseallqaqallanssqppetlqlhidkaisglrs<br>ltsllrvlgaqkelmsppdttppaplrtltvdtfcklfrvyanflrgklkly<br>tgevcrrgdr |
| Rat Epo NP_058697.1 | 84<br>apprlicdsrvleryileakeaenvtmgcaegprlsenitvpdtkvnfyawk<br>rmkveeqavevwqglsllseailqaqalqanssqppeslqlhidkaisglrs<br>ltsllrvlgaqkelmsppdatqaaplrtltadtfcklfrvysnflrgklkly<br>tgeacrrgdr |
| Rabbit Epo NP_001075559.1 | 85<br>Klatmgvrgrlallplallcllvlalglpvlgaparlicdsrvleryileak<br>eaenvtmgcaegcslgenitvpdtkvnfhhwkkseagrhavevwqglallse<br>amlrsqallanssqlpetlqvhvdkaysglrsltsllralgvqkeaysppea<br>assaaplrtvaadticklfriysnflrgklklytgeacrrgdr |
| Epo Helix A, amino acids 4-26 of SEQ ID NO: 81 | 86<br>rlicdsrvleryllleakeaenit |

TABLE 1-continued

Examples of Epo Antibodies, Fabs and Epo Proteins

| Amino acid sequence or polynucleotide (PN) | Sequence Identifier (SEQ.I.D.NO:) and sequence |
|---|---|
| Epo Helix B, amino acids 56-83 of SEQ ID NO: 81 | 87<br>vgqqavevwqglallseavlrgqallvn |
| Epo Helix D, amino acids 138-162 of SEQ ID NO: 81 | 88<br>frklfrvysnflrgklklytgeacr |
| Epo Loop A-B, amino acids 27-55 of SEQ ID NO: 81 | 89<br>tgcaehcslnenitvpdtkvnfyawkrme |

Other antibodies of the invention include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen binding activity.

Since each of these antibodies can bind to Epo, the VH, VL, full length light chain, and full length heavy chain sequences (amino acid sequences and the nucleotide sequences encoding the amino acid sequences) can be "mixed and matched" to create other Epo-binding antibodies of the invention. Such "mixed and matched" Epo-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated antibody or antigen binding region thereof having: a heavy chain variable domain comprising an amino acid sequence selected from the group consisting of SEQ ID NOs: 13, 33, 53, and 73, and a light chain variable domain comprising an amino acid sequence selected from the group consisting of SEQ ID NOs: 14, 34, 54 and 74 wherein the antibody specifically binds to Epo (e.g., human, cynomolgus, rat and/or mouse Epo). More specifically, in certain aspects, the invention provides an isolated antibody or antigen binding region thereof having a heavy chain variable domain and a light chain variable domain comprising amino acid sequences selected from SEQ ID NOs: 13 and 14, respectively. In other specific aspects, the invention provides an isolated antibody or antigen binding region thereof having a heavy chain variable domain and a light chain variable domain comprising amino acid sequences selected from SEQ ID NOs: 33 and 34, respectively. In still other aspects, the invention provides an isolated antibody or antigen binding region thereof having a heavy chain variable domain and a light chain variable domain comprising amino acid sequences selected from SEQ ID NOs: 53 and 54, respectively. In still other aspects, the invention provides an isolated antibody or antigen binding region thereof having a heavy chain variable domain and a light chain variable domain comprising amino acid sequences selected from SEQ ID NOs: 73 and 74, respectively.

In another aspect, the invention provides (i) an isolated antibody having: a full length heavy chain comprising an amino acid sequence that has been optimized for expression in a mammalian cell selected from the group consisting of SEQ ID NOs: 15, 35, 55 and 75, and a full length light chain comprising an amino acid sequence that has been optimized for expression in a mammalian cell selected from the group consisting of SEQ ID NOs: 16, 36, 56, and 76; or (ii) a functional protein comprising an antigen binding portion thereof. More specifically, in certain aspects, the invention provides an isolated antibody or antigen binding region thereof having a heavy chain and a light chain comprising amino acid sequences selected from SEQ ID NOs: 15 and 16, respectively. In other specific aspects, the invention provides an isolated antibody or antigen binding region thereof having a heavy chain and a light chain comprising amino acid sequences selected from SEQ ID NOs: 35 and 36, respectively. In still other aspects, the invention provides an isolated antibody or antigen binding region thereof having a heavy chain and a light chain comprising amino acid sequences selected from SEQ ID NOs: 55 and 56, respectively. In still other aspects, the invention provides an isolated antibody or antigen binding region thereof having a heavy chain and a light chain comprising amino acid sequences selected from SEQ ID NOs: 75 and 76, respectively.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme).

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

In another aspect, the present invention provides Epo binding antibodies that comprise the heavy chain and light chain CDR1s, CDR2s, and CDR3s as described in Table 1, or combinations thereof. The amino acid sequences of the VH CDR1 s of the antibodies are shown in SEQ ID NOs: 1, 21, 41 or 61. The amino acid sequences of the VH CDR2s of the antibodies and are shown in SEQ ID NOs: 2, 22, 42 or 62. The amino acid sequences of the VH CDR3s of the antibodies are shown in SEQ ID NOs: 3, 23, 43, or 63. The amino acid sequences of the VL CDR1 s of the antibodies are shown in SEQ ID NOs: 4, 24, 44, or 64. The amino acid sequences of the VL CDR2s of the antibodies are shown in SEQ ID NOs: 5, 25, 45, or 65. The amino acid sequences of the VL CDR3s of the antibodies are shown in SEQ ID NOs: 6, 26, 46, or 66. These CDR regions are delineated using the Kabat system.

Alternatively, as defined using the Chothia system (Al-Lazikani et al., (1997) JMB 273, 927-948) the amino acid sequences of the VH CDR1s of the antibodies are shown in SEQ ID NOs: 7, 27, 47, or 67. The amino acid sequences of the VH CDR2s of the antibodies and are shown in SEQ ID NOs: 8, 28, 48, or 68. The amino acid sequences of the VH CDR3s of the antibodies are shown in SEQ ID NOs: 9, 29, 49, or 69. The amino acid sequences of the VL CDR1s of the antibodies are shown in SEQ ID NOs: 10, 30, 50, or 70. The amino acid sequences of the VL CDR2s of the antibodies are shown in SEQ ID NOs: 11, 31, 51, or 71. The amino acid sequences of the VL CDR3s of the antibodies are shown in SEQ ID NOs: 12, 32, 52, or 72.

Given that each of these antibodies can bind to Epo and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody preferably contains a VH CDR1, 2 and 3 and a VL CDR1, 2 and 3 to create other Epo binding molecules of the invention. Such "mixed and matched" Epo binding antibodies can be tested using the binding assays known in the art and those described in the Examples (e.g., ELISAs, SET, Biacore). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention. In addition to the foregoing, in one embodiment, the antigen binding fragments of the antibodies described herein can comprise a VH CDR1, 2, and 3, or a VL CDR 1, 2, and 3, wherein the fragment binds to Epo as a single variable domain.

In certain embodiments of the invention, the antibodies or antigen binding fragments thereof may have the heavy and light chain sequences of the Fabs described in Table 1. More specifically, the antibody or antigen binding fragment thereof may have the heavy and light sequence of Fab NVS1, NVS2, NVS3 or NVS4.

In other embodiments of the invention the antibody or antigen binding fragment that specifically binds Epo comprises a heavy chain variable region CDR1, a heavy chain variable region CDR2, a heavy chain variable region CDR3, a light chain variable region CDR1, a light chain variable region CDR2, and a light chain variable region CDR3 as defined by Kabat and described in Table 1. In still other embodiments of the invention the antibody or antigen binding fragment in that specifically binds Epo comprises a heavy chain variable region CDR1, a heavy chain variable region CDR2, a heavy chain variable region CDR3, a light chain variable region CDR1, a light chain variable region CDR2, and a light chain variable region CDR3 as defined by Chothia and described in Table 1.

In a specific embodiment, the invention includes an antibody that specifically binds to Epo comprising a heavy chain variable region CDR1 of SEQ ID NO:1; a heavy chain variable region CDR2 of SEQ ID NO: 2; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 6. In another specific embodiment, the invention includes an antibody that specifically binds to Epo comprising a heavy chain variable region CDR1 of SEQ ID NO: 21; a heavy chain variable region CDR2 of SEQ ID NO: 22; a heavy chain variable region CDR3 of SEQ ID NO: 23; a light chain variable region CDR1 of SEQ ID NO: 24; a light chain variable region CDR2 of SEQ ID NO: 25; and a light chain variable region CDR3 of SEQ ID NO: 26. In another specific embodiment, the invention includes an antibody that specifically binds to Epo comprising a heavy chain variable region CDR1 of SEQ ID NO: 41; a heavy chain variable region CDR2 of SEQ ID NO: 42; a heavy chain variable region CDR3 of SEQ ID NO: 43; a light chain variable region CDR1 of SEQ ID NO: 44; a light chain variable region CDR2 of SEQ ID NO: 45; and a light chain variable region CDR3 of SEQ ID NO: 46. In another specific embodiment, the invention includes an antibody that specifically binds to Epo comprising a heavy chain variable region CDR1 of SEQ ID NO: 61; a heavy chain variable region CDR2 of SEQ ID NO: 62; a heavy chain variable region CDR3 of SEQ ID NO: 63; a light chain variable region CDR1 of SEQ ID NO: 64; a light chain variable region CDR2 of SEQ ID NO: 65; and a light chain variable region CDR3 of SEQ ID NO: 66.

In another specific embodiment, the invention includes an antibody that specifically binds to Epo comprising a heavy chain variable region CDR1 of SEQ ID NO: 7; a heavy chain variable region CDR2 of SEQ ID NO: 8; a heavy chain variable region CDR3 of SEQ ID NO: 9; a light chain variable region CDR1 of SEQ ID NO: 10; a light chain variable region CDR2 of SEQ ID NO: 11; and a light chain variable region CDR3 of SEQ ID NO: 12. In another specific embodiment, the invention includes an antibody that specifically binds to Epo comprising a heavy chain variable region CDR1 of SEQ ID NO: 27; a heavy chain variable region CDR2 of SEQ ID NO: 28; a heavy chain variable region CDR3 of SEQ ID NO: 29; a light chain variable region CDR1 of SEQ ID NO: 30; a light chain variable region CDR2 of SEQ ID NO: 31; and a light chain variable region CDR3 of SEQ ID NO: 32. In another specific embodiment, the invention includes an antibody that specifically binds to Epo comprising a heavy chain variable region CDR1 of SEQ ID NO: 47; a heavy chain variable region CDR2 of SEQ ID NO: 48; a heavy chain variable region CDR3 of SEQ ID NO: 49; a light chain variable region CDR1 of SEQ ID NO: 50; a light chain variable region CDR2 of SEQ ID NO: 51; and a light chain variable region CDR3 of SEQ ID NO: 52. In another specific embodiment, the invention includes an antibody that specifically binds to Epo comprising a heavy chain variable region CDR1 of SEQ ID NO: 67; a heavy chain variable region CDR2 of SEQ ID NO: 68; a heavy chain variable region CDR3 of SEQ ID NO: 69; a light chain variable region CDR1 of SEQ ID NO: 70; a light chain variable region CDR2 of SEQ ID NO: 71; and a light chain variable region CDR3 of SEQ ID NO: 72.

In certain embodiments, the invention includes antibodies or antigen binding fragments that specifically bind to Epo as described in Table 1. In a preferred embodiment, the antibody, or antigen binding fragment, that binds Epo is Fab NVS1, NVS2, NVS3, or NVS4.

As used herein, a human antibody comprises heavy or light chain variable regions or full length heavy or light chains that are the product of or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is the product of or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described below, as well as DP47 and DPK9.

Homologous Antibodies

In yet another embodiment, the present invention provides an antibody, or an antigen binding fragment thereof, comprising amino acid sequences that are homologous to the sequences described in Table 1, and the antibody binds to an Epo protein (e.g., human, cynomolgus, rat and/or mouse Epo), and retains the desired functional properties of those antibodies described in Table 1.

For example, the invention provides an isolated antibody, or a functional antigen binding fragment thereof, comprising a heavy chain variable domain and a light chain variable domain, wherein the heavy chain variable domain comprises an amino acid sequence that is at least 80%, 85%, 90%, 95%, 96%, 97%, 98% or 99% identical to an amino acid sequence selected from the group consisting of SEQ ID NOs: 13, 33, 53, and 73; the light chain variable domain comprises an amino acid sequence that is at least 80%, 85%, 90%, 95%, 96%, 97%, 98% or 99% identical to an amino acid sequence selected from the group consisting of SEQ ID NOs: 14, 34, 54, and 74; and the antibody specifically binds to Epo (e.g., human, cynomolgus, rat and/or mouse Epo). In certain aspects of the invention the heavy and light chain sequences further comprise HCDR1, HCDR2, HCDR3, LCDR1, LCDR2, and LCDR3 sequences as defined by Kabat, for example SEQ ID NOs: 1, 2, 3, 4, 5, and 6, respectively; SEQ ID NOs: 21, 22, 23, 24, 25, and 26, respectively; SEQ ID NOs: 41, 42, 43, 44, 45, and 46, respectively; or SEQ ID NOs: 61, 62, 63, 64, 65, and 66, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 7, 8, 9, 10, 11, and 12, respectively; SEQ ID NOs: 27, 28, 29, 30, 31, and 32, respectively; SEQ ID NOs: 47, 48, 49, 50, 51, and 52, respectively; or SEQ ID NOs: 67, 68, 69, 70, 71, and 72, respectively.

In other embodiments, the VH and/or VL amino acid sequences may be 80%, 85%, 90%, 95%, 96%, 97%, 98% or 99% identical to the sequences set forth in Table 1. In other embodiments, the VH and/or VL amino acid sequences may be identical except for an amino acid substitution in no more than 1, 2, 3, 4 or 5 amino acid positions. An antibody having VH and VL regions having high (i.e., 80% or greater) identity to the VH and VL regions of those described in Table 1 can be obtained by mutagenesis (e.g., site-directed or PCR-mediated mutagenesis) of nucleic acid molecules encoding SEQ ID NOs: 13, 33, 53 or 73 and SEQ ID NOs: 14, 34, 54, or 74, respectively, followed by testing of the encoded altered antibody for retained function using the functional assays described herein.

In other embodiments, the full length heavy chain and/or full length light chain amino acid sequences may be 80%, 85%, 90%, 95%, 96%, 97%, 98% or 99% identical to the sequences set forth in Table 1. An antibody having a full length heavy chain and full length light chain having high (i.e., 80% or greater) identity to the full length heavy chains of any of SEQ ID NOs: 15, 35, 55, or 75, and full length light chains of any of SEQ ID NOs: 16, 36, 56, or 76, can be obtained by mutagenesis (e.g., site-directed or PCR-mediated mutagenesis) of nucleic acid molecules encoding such polypeptides, followed by testing of the encoded altered antibody for retained function using the functional assays described herein.

In other embodiments, the full length heavy chain and/or full length light chain nucleotide sequences may be 80%, 85%, 90%, 95%, 96%, 97%, 98% or 99% identical to the sequences set forth in Table 1.

In other embodiments, the variable regions of heavy chain and/or the variable regions of light chain nucleotide sequences may be 80%, 85%, 90%, 95%, 96%, 97%, 98% or 99% identical to the sequences set forth in Table 1.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the Epo-binding antibodies of the invention. Accordingly, the invention provides an isolated antibody, or an antigen binding fragment thereof, comprising of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 1, 21, 41, and 61, and conservative modifications thereof; the heavy chain variable region CDR2 amino acid sequences are selected from the group consisting of SEQ ID NOs: 2, 22, 42 and 62, and conservative modifications thereof; the heavy chain variable region CDR3 amino acid sequences are selected from the group consisting of SEQ ID NOs: 3, 23, 43, and 63, and conservative modifications thereof; the light chain variable regions CDR1 amino acid sequences are selected from the group consisting of SEQ ID NOs: 4, 24, 44 and 64, and conservative modifications thereof; the light chain variable regions CDR2 amino acid sequences are selected from the group consisting of SEQ ID NOs: 5, 25, 45 and 65, and conservative modifications thereof; the light chain variable regions of CDR3 amino acid sequences are selected from the group consisting of SEQ ID NOs: 6, 26, 46, and 66, and conservative modifications thereof; and the antibody or antigen binding fragment thereof specifically binds to Epo.

In other embodiments, the antibody of the invention is optimized for expression in a mammalian cell and has a full length heavy chain sequence and a full length light chain sequence, wherein one or more of these sequences have specified amino acid sequences based on the antibodies described herein or conservative modifications thereof, and wherein the antibodies retain the desired functional properties of the Epo binding antibodies of the invention. Accordingly, the invention provides an isolated antibody optimized for expression in a mammalian cell consisting of a full length heavy chain and a full length light chain wherein the full length heavy chain has amino acid sequences selected from the group of SEQ ID NOs: 15, 35, 55 and 75, and conservative modifications thereof; and the full length light chain has amino acid sequences selected from the group of SEQ ID NOs: 16, 36, 56, and 76, and conservative modifications thereof; and the antibody specifically binds to Epo (e.g., human, cynomolgus, rat and/or mouse Epo).

Antibodies that Bind to the Same Epitope

The present invention provides antibodies that bind to the same epitope as the Epo binding antibodies described in Table 1. Additional antibodies can therefore be identified based on their ability to compete (e.g., to competitively inhibit the binding of, in a statistically significant manner) with other antibodies of the invention in Epo binding assays (such as those described in the Examples). The ability of a test antibody to inhibit the binding of antibodies of the present invention to an Epo protein demonstrates that the test antibody can compete with that antibody for binding to Epo; such an antibody may, according to non-limiting theory, bind to the same or a related (e.g., a structurally similar or spatially proximal) epitope on the Epo protein as the antibody with which it competes. In a certain embodiment, the antibody that binds to the same epitope on Epo as the antibodies of the present invention is a human monoclonal antibody. Such human monoclonal antibodies can be prepared and isolated as described herein. As used herein, an antibody "competes" for binding when the competing antibody inhibits Epo binding of an antibody or antigen binding fragment of the invention by more than 50%, in the presence of an equimolar concentration of competing antibody.

In other embodiments the antibodies or antigen binding fragments of the invention bind the Helix D domain of Epo (amino acids 138-162 of the Epo protein; SEQ ID NO: 88). In other embodiments the antibodies or antigen binding fragments of the invention bind the Helix A (amino acids 4-26 of the Epo protein; SEQ ID NO: 86) and Loop A-B of Epo (amino acids 27-55 of the Epo protein; SEQ ID NO: 89).

In other embodiments the antibodies, or antigen binding fragments of the invention bind to the D Helix domain of Epo (amino acids 138-162 of Human Epo; SEQ ID NO: 88). In other embodiments, the isolated antibodies, or antigen binding fragments bind the Loop A-B domain (amino acids 27-55 of Human Epo; SEQ ID NO: 89). In other embodiments the isolated antibodies, or antigen binding fragments bind the Loop A-B domain (amino acids 27-55 of Human Epo; SEQ ID NO: 89) and Helix A (amino acids 4-26 of Human Epo; SEQ ID NO: 86). In still other embodiments the isolated antibodies, or antigen binding fragments bind the D Helix domain of Epo (amino acids 138-162 of Human Epo; SEQ ID NO: 88), and the Loop A-B domain (amino acids 27-55 of Human Epo; SEQ ID NO: 89). In other embodiments the isolated antibodies, or antigen binding fragments bind the D Helix domain of Epo (amino acids 138-162 of Human Epo; SEQ ID NO: 88), the Loop A-B domain (amino acids 27-55 of Human Epo; SEQ ID NO: 89) and Helix A (amino acids 4-26 of Human Epo; SEQ ID NO: 86).

In other aspects of the invention the isolated antibodies or antigen binding fragments bind an epitope comprising amino acids at positions, 44-50, 52, 53, 147, 150, 151, 154, 155, 159, and 162 of Human Epo (SEQ ID NO. 81). In other aspects of the invention the isolated antibodies or antigen binding fragments bind an epitope comprising amino acids at positions 9, 13, 44-53, 147, 150, 151, 154, 155, 158, 159, and 162 of Human Epo (SEQ ID NO. 81). In other aspects of the invention the isolated antibodies or antigen binding fragments bind an epitope comprising amino acids at positions 23, 43-50, 52, 53, 131, 143, 147, 150, 151, 154, 155, 159, and 162 of Human Epo (SEQ ID NO. 81). In particular aspects of the invention the isolated antibodies or antigen binding fragments bind an epitope comprising amino acids Thr-Lys-Val-Asn-Phe-Tyr-Ala (at positions 44-50), Lys-Arg (at positions 52-53), Asn (at position 147), Arg-Gly (at positions 150-151), Lys-Leu (at positions 154-155), Glu (at position 159), and Arg (at position 162) of Human Epo (SEQ ID NO. 81). In other particular aspects of the invention the isolated antibodies or antigen binding fragments bind an epitope comprising amino acids Ser (at position 9), Glu (at position 13), Thr-Lys-Val-Asn-Phe-Tyr-Ala (at positions 44-50), Lys-Arg (at positions 52-53), Asn (at position 147), Arg-Gly (at positions 150-151), Lys-Leu (at positions 154-155), Gly (at position 158), Glu (at position 159), and Arg (at position 162) of Human Epo (SEQ ID NO. 81). In still further aspects of the invention the isolated antibodies or antigen binding fragments bind an epitope comprising amino acids Glu (at positions 23), Asp-Thr-Lys-Val-Asn-Phe-Tyr-Ala (at positions 43-50), Lys-Arg (at positions 52-53), Arg (at position 131), Arg (at position 143), Asn (at position 147), Arg-Gly (at positions 150-151), Lys-Leu (at positions 154-155), Glu (at position 159), and Arg (at position 162) of Human Epo (SEQ ID NO. 81).

The invention also includes a conformational epitope on human Epo, the epitope comprising amino acid residues Thr44, Lys45, Val46, Asn47, Phe48, Tyr49, Ala50, Lys52, Arg53, Asn147, Arg150, Gly151, Lys154, Leu155, Glu159, and Arg162, wherein an antibody binding to the epitope will inhibit Epo binding to the Epo receptor. It is also contemplated that an antibody binding to the epitope of the invention will further inhibit Epo-dependent cell proliferation.

The invention further includes a conformational epitope on human Epo, the epitope comprising amino acid residues Ser9, Glu13, Thr44, Lys45, Val46, Asn47, Phe48, Tyr49, Ala50, Lys52, Arg53, Asn147, Arg150, Gly151, Lys154, Leu155, Gly158, Glu159, and Arg162, wherein an antibody binding to the epitope will inhibit Epo binding to the Epo receptor. It is also contemplated that an antibody binding to the epitope of the invention will further inhibit Epo-dependent cell proliferation.

The present invention still further includes a conformational epitope on human Epo, the epitope comprising amino acid residues Glu23, Asp43, Thr44, Lys45, Val46, Asn47, Phe48, Tyr49, Ala50, Lys52, Arg53, Arg131, Arg143, Asn147, Arg150, Gly151, Lys154, Leu155, Glu159, and Arg162, wherein an antibody binding to the epitope will inhibit Epo binding to the Epo receptor. It is also contemplated that an antibody binding to the epitope of the invention will further inhibit Epo-dependent cell proliferation.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated antibody, or an antigen binding fragment thereof, comprising a heavy chain variable region comprising CDR1 sequences having an amino acid sequence selected from the group consisting of SEQ ID NOs: 1, 21, 41, and 61; CDR2 sequences having an amino acid sequence selected from the group consisting of SEQ ID NOs: 2, 22, 42, and 62; CDR3 sequences having an amino acid sequence selected from the group consisting of SEQ ID NOs: 3, 23, 43 and 63, respectively; and a light chain variable region having CDR1 sequences having an amino acid sequence selected from the group consisting of SEQ ID NOs: 4, 24, 44 and 64; CDR2 sequences having an amino acid sequence selected from the group consisting of SEQ ID NOs: 5, 25, 45, and 65; and CDR3 sequences consisting of an amino acid sequence selected from the group consisting of SEQ ID NOs: 6, 26, 46, and 66, respectively. Thus, such antibodies contain the VH and VL CDR sequences of monoclonal antibodies, yet may contain different framework sequences from these antibodies.

Alternatively, another embodiment of the invention pertains to an isolated antibody, or an antigen binding fragment thereof, comprising a heavy chain variable region comprising CDR1 sequences having an amino acid sequence selected from the group consisting of SEQ ID NOs: 7, 27, 47, and 67; CDR2 sequences having an amino acid sequence selected from the group consisting of SEQ ID NOs: 8, 28, 48, and 68; CDR3 sequences having an amino acid sequence selected from the group consisting of SEQ ID NOs: 9, 29, 49, and 69, respectively; and a light chain variable region having CDR1 sequences having an amino acid sequence selected from the group consisting of SEQ ID NOs: 10, 30, 50, and 70; CDR2 sequences having an amino acid sequence selected from the group consisting of SEQ ID NOs: 11, 31, 51, and 71; and CDR3 sequences consisting of an amino acid sequence selected from the group consisting of SEQ ID NOs: 12, 32, 52, and 72, respectively. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al). Frameworks that can be utilized as scaffolds on which to build the antibodies and antigen binding fragments described herein include, but are not limited to VH1A, VH1B, VH3, Vk1, Vl2, and Vk2. Additional frameworks are known in the art and may be found, for example, in the vBase data base on the world wide web at vbase.mrc-cpe.cam.ac.uk/index.php?&MMN_position=1:1.

Accordingly, an embodiment of the invention relates to isolated Epo binding antibodies, or antigen binding fragments thereof, comprising a heavy chain variable region comprising an amino acid sequence selected from the group consisting of SEQ ID NOs: 13, 33, 53, and 73, or an amino acid sequence having one, two, three, four or five amino acid substitutions, deletions or additions in the framework region of such sequences, and further comprising a light chain variable region having an amino acid sequence selected from the group consisting of SEQ ID NOs: 14, 34, 54, and 74, or an amino acid sequence having one, two, three, four or five amino acid substitutions, deletions or additions in the framework region of such sequences.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated Epo-binding antibodies, or antigen binding fragments thereof, consisting of a heavy chain variable region having a VH CDR1 region consisting of an amino acid sequence selected from the group having SEQ ID NOs: 1, 21, 41, and 61 or an amino acid sequence having one, two, three, four or five amino acid substitutions, deletions or additions as compared to SEQ ID NOs: 1, 21, 41, or 61; a VH CDR2 region having an amino acid sequence selected from the group consisting of SEQ ID NOs: 2, 22, 42, and 62 or an amino acid sequence having one, two, three, four or five amino acid substitutions, deletions or additions as compared to SEQ ID NOs: 2, 22, 42, or 62; a VH CDR3 region having an amino acid sequence selected from the group consisting of SEQ ID NOs: 3, 23, 43, and 63, or an amino acid sequence having one, two, three, four or five amino acid substitutions, deletions or additions as compared to SEQ ID NOs: 3, 23, 43, or 63; a VL CDR1 region having an amino acid sequence selected from the group consisting of SEQ ID NOs: 4, 24, 44, and 64, or an amino acid sequence having one, two, three, four or five amino acid substitutions, deletions or additions as compared to SEQ ID NOs: 4, 24, 44, or 64; a VL CDR2 region having an amino acid sequence selected from the group consisting of SEQ ID NOs: 5, 25, 45, and 65, or an amino acid sequence having one, two, three, four or five amino acid substitutions, deletions or additions as compared to SEQ ID NOs: 5, 25, 45, or 65; and a VL CDR3 region having an amino acid sequence selected from the group consisting of SEQ ID NOs: 6, 26, 46, and 66, or an amino acid sequence having one, two, three, four or five amino acid substitutions, deletions or additions as compared to SEQ ID NOs: 6, 26, 46, or 66.

Accordingly, in another embodiment, the invention provides isolated Epo-binding antibodies, or antigen binding fragments thereof, consisting of a heavy chain variable region having a VH CDR1 region consisting of an amino acid sequence selected from the group having SEQ ID NOs: 7, 27, 47, and 67 or an amino acid sequence having one, two, three, four or five amino acid substitutions, deletions or additions as compared to SEQ ID NOs:7, 27, 47, or 67; a VH CDR2 region having an amino acid sequence selected from the group consisting of SEQ ID NOs: 8, 28, 48, and 68 or an amino acid sequence having one, two, three, four or five amino acid substitutions, deletions or additions as compared to SEQ ID NOs: 8, 28, 48, or 68; a VH CDR3 region having an amino acid sequence selected from the group consisting of SEQ ID NOs: 9, 29, 49, and 69, or an amino acid sequence having one, two, three, four or five amino acid substitutions, deletions or additions as compared to SEQ ID NOs: 9, 29, 49, or 69; a VL CDR1 region having an amino acid sequence selected from the group consisting of SEQ ID NOs: 10, 30, 50, and 70, or an amino acid sequence having one, two, three, four or five amino acid substitutions, deletions or additions as compared to SEQ ID NOs: 10, 30 50, or 70; a VL CDR2 region having an amino acid sequence selected from the group consisting of SEQ ID NOs: 11, 31, 51, and 71, or an amino acid sequence having one, two, three, four or five amino acid substitutions, deletions or additions as compared to SEQ ID NOs: 11, 31, 51, or 71; and a VL CDR3 region having an amino acid sequence selected from the group consisting of SEQ ID NOs: 12, 32, 52, and 72, or an amino acid sequence having one, two, three, four or five amino acid substitutions, deletions or additions as compared to SEQ ID NOs: 12, 32, 52, or 72.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to Epo. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target Epo protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (SciI Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris brassicae* has been used to develop anticalins by mutagenizing the set of four loops. One example of a patent application describing anticalins is in PCT Publication No. WO 1999/16873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO 2001/04144 and examples of "ubiquitin-like" proteins are described in WO 2004/106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The present invention provides fully human antibodies that specifically bind to an Epo protein. Compared to the chimeric or humanized antibodies, the human Epo-binding antibodies of the invention have further reduced antigenicity when administered to human subjects.

Camelid Antibodies

Antibody proteins obtained from members of the camel and dromedary (*Camelus bactrianus* and *Camelus dromaderius*) family including new world members such as llama species (*Lama pacos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for Epo. In certain embodiments herein, the camelid antibody or nanobody is naturally produced in the camelid animal, i.e., is produced by the camelid following immunization with Epo or a peptide fragment thereof, using techniques described herein for other antibodies. Alternatively, the Epo-binding camelid nanobody is engineered, i.e., produced by selection for example from a library of phage displaying appropriately mutagenized camelid nanobody proteins using panning procedures with Epo as a target as described in the examples herein. Engineered nanobodies can further be customized by genetic engineering to have a half-life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in WO 1994/004678.

Bispecific Molecules and Multivalent Antibodies

In another aspect, the present invention features bispecific or multispecific molecules comprising an Epo-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for Epo and a second binding specificity for a second target epitope. For example, the second target epitope is another epitope of Epo different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the invention are murine, chimeric and humanized monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-l-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies of the invention binding to Epo. The antigen-binding portions can be linked together via protein fusion or covalent or noncovalent linkage. Alternatively, methods of linkage have been described for the bispecific molecules. Tetravalent compounds can be obtained for example by cross-linking antibodies of the antibodies of the invention with an antibody that binds to the constant regions of the antibodies of the invention, for example the Fc or hinge region.

Trimerizing domain are described for example in Borean patent EP 1 012 280B1. Pentamerizing modules are described for example in WO 1998/018943.

Antibodies with Extended Half Life

The present invention provides for antibodies that specifically bind to Epo protein which have an extended half-life in vivo.

Many factors may affect a protein's half-life in vivo, for example, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half-life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight polyethylene glycol (PEG) can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with PEG, such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the terms "polyethylene glycol" and "PEG" are intended to encompass any of the forms of PEG that have been used to derivative other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum half-life extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum half-life of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin (e.g., human serum albumin; HSA) in order to make the antibody or antibody fragment more stable in vivo or have a longer half-life in vivo. The techniques are well-known in the art, see, e.g., International Publication Nos. WO 93/15199, WO 93/15200, and WO 01/77137; and European Patent No. EP0 413622. In addition, in the context of a bispecific antibody as described above, the specificities of the antibody can be designed such that one binding domain of the antibody binds to Epo while a second binding domain of the antibody binds to serum albumin, preferably HSA.

The strategies for increasing half-life are especially useful in nanobodies, fibronectin-based binders, and other antibodies or proteins for which increased in vivo half-life is desired.

Antibody Conjugates

The present invention provides antibodies or fragments thereof that specifically bind to an Epo protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 0307434 and EP 0367166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an Epo protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide (SEQ ID NO: 92), such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine (SEQ ID NO: 92) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and non-radioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alpha-emitters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies of the Invention
Nucleic Acids Encoding the Antibodies The invention provides substantially purified nucleic acid molecules which encode polypeptides comprising segments or domains of the Epo-binding antibody chains described above. Some of the nucleic acids of the invention comprise the nucleotide sequence encoding the heavy chain variable region shown in SEQ ID NO: 13, 33, 53, or 73, and/or the nucleotide sequence encoding the light chain variable region shown in SEQ ID NO: 14, 34, 54, or 74. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting Epo antigen binding capacity.

Also provided in the invention are polynucleotides which encode at least one CDR region and usually all three CDR regions from the heavy or light chain of the Epo-binding antibody set forth above. Some other polynucleotides encode all or substantially all of the variable region sequence of the heavy chain and/or the light chain of the Epo-binding antibody set forth above. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a mature heavy chain sequence that is substantially identical (e.g., at least 80%, 85% 90%, 95%, 96%, 97%, 98% or 99%) to the mature heavy chain sequence set forth in SEQ ID NO: 15, 35, 55, or 75. Some other nucleic acid sequences comprising nucleotide encoding a mature light chain sequence that is substantially identical (e.g., at least 80%, 85%, 90%, 95%, 96%, 97%, 98% or 99%) to the mature light chain sequence set forth in SEQ ID NO: 16, 36, 56, or 76.

The polynucleotide sequences can be produced by de novo solid-phase DNA synthesis or by PCR mutagenesis of an existing sequence (e.g., sequences as described in the Examples below) encoding an Epo-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the Epo-binding antibodies described above. Various expression vectors can be employed to express the polynucleotides encoding the Epo-binding antibody chains or binding fragments. Both viral-based and non-viral expression vectors can be used to produce the antibodies in a mammalian host cell. Non-viral vectors and systems include plasmids, episomal vectors, typically with an expression cassette for expressing a protein or RNA, and human artificial chromosomes (see, e.g., Harrington et al., Nat Genet 15:345, 1997). For example, non-viral vectors useful for expression of the Epo-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an Epo-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements may also be required or desired for efficient expression of an Epo-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted Epo-binding antibody sequences. More often, the inserted Epo-binding antibody sequences are linked to a signal sequences before inclusion in the vector. Vectors to be used to receive sequences encoding Epo-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the Epo-binding antibody chains can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express Epo-binding polypeptides of the invention. Insect cells in combination with baculovirus vectors can also be used.

In some preferred embodiments, mammalian host cells are used to express and produce the Epo-binding polypeptides of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express Epo-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

Animal systems for preparing hybridomas include the murine, rat and rabbit systems. Hybridoma production in the mouse is a well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the invention are human monoclonal antibodies. Such human monoclonal antibodies directed against Epo can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (µ and γ) and κ light chain immunoglobulin sequences, together with targeted mutations that inactivate the endogenous µ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchromosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise Epo-binding antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise Epo-binding antibodies of the invention. For example, mice carrying both a human heavy chain transchromosome and a human light chain transchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise Epo-binding antibodies of the invention.

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the Epo-binding antibodies having VH and VL sequences or full length heavy and light chain sequences shown herein can be used to create new Epo-binding antibodies by modifying full length heavy chain and/or light chain sequences, VH and/or VL sequences, or the constant region(s) attached thereto. Thus, in another aspect of the invention, the structural features of an Epo-binding antibody of the invention are used to create structurally related Epo-binding antibodies that retain at least one functional property of the antibodies of the invention, such as binding to human Epo and also inhibiting one or more functional properties of Epo (e.g., inhibit Epo binding to the Epo receptor, inhibit Epo-dependent cell proliferation).

For example, one or more CDR regions of the antibodies of the present invention, or mutations thereof, can be combined recombinantly with known framework regions and/or other CDRs to create additional, recombinantly-engineered, Epo-binding antibodies of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing a modified Epo-binding antibody comprising the steps of: a) producing and Epo-binding antibody comprising a heavy chain variable region antibody sequence having a CDR1 sequence selected from the group consisting of SEQ ID NOs: 1, 21, 41, and 61, a CDR2 sequence selected from the group consisting of SEQ ID NOs: 2, 22, 42, and 62, and/or a CDR3 sequence selected from the group consisting of SEQ ID NOs: 3, 23, 43, and 63; and a light chain variable region antibody sequence having a CDR1 sequence selected from the group consisting of SEQ ID NOs: 4, 24, 44, and 64, a CDR2 sequence selected from the group consisting of SEQ ID NOs: 5, 25, 45, and 65, and/or a CDR3 sequence selected from the group consisting of SEQ ID NOs: 6, 26, 46, and 66; b) altering at least one amino acid residue within the heavy chain variable region antibody sequence and/or the light chain variable region antibody sequence to create at least one altered antibody sequence; and c) expressing the altered antibody sequence as a protein.

Accordingly, in another embodiment, the invention provides a method for preparing an Epo-binding antibody consisting of a heavy chain variable region antibody sequence having a CDR1 sequence selected from the group consisting of SEQ ID NOs: 7, 27, 47, and 67, a CDR2 sequence selected from the group consisting of SEQ ID NOs: 8, 28, 48, and 68, and/or a CDR3 sequence selected from the group consisting of SEQ ID NOs: 9, 29, 49, and 69; and a light chain variable region antibody sequence having a CDR1 sequence selected from the group consisting of SEQ ID NOs: 10, 30, 50, and 70, a CDR2 sequence selected from the group consisting of SEQ ID NOs: 11, 31, 51, and 71, and/or a CDR3 sequence selected from the group consisting of SEQ ID NOs: 12, 32, 52, and 72; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing an Epo-binding antibody optimized for expression in a mammalian cell consisting of: a full length heavy chain antibody sequence having a sequence selected from the group of SEQ ID NOs: 15, 35, 55 and 75; and a full length light chain antibody sequence having a sequence selected from the group of SEQ ID NOs: 16, 36, 56, and 76; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the Epo-binding antibodies described herein, which functional properties include, but are not limited to, specifically binding to human, cynomolgus, rat, and/or mouse Epo; and the antibody inhibit Epo-dependent cell proliferation in a F36E and/or Ba/F3-EpoR cell proliferation assay.

In certain embodiments of the methods of engineering antibodies of the invention, mutations can be introduced randomly or selectively along all or part of an Epo-binding antibody coding sequence and the resulting modified Epo-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain embodiments of the invention antibodies have been engineered to remove sites of deamidation. Deamidation is known to cause structural and functional changes in a peptide or protein. Deamidation can result in decreased bioactivity, as well as alterations in pharmacokinetics and antigenicity of the protein pharmaceutical. (*Anal Chem.* 2005 Mar. 1; 77(5):1432-9).

In certain embodiments of the invention the antibodies have been engineered to increase pI and improve their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-Epo antibodies, or Fabs, of the invention improved their solubility, enabling the antibodies to be formulated at higher concentrations (>100 mg/ml). Formulation of the antibodies at high concentrations (e.g. >100 mg/ml) offers the advantage of being able to administer higher doses of the antibodies into eyes of patients via intravitreal injections, which in turn may enable reduced dosing frequency, a significant advantage for treatment of chronic diseases including retinal vascular diseases. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. Preferably, the pI is greater than or equal to 8.2.

The functional properties of the altered antibodies can be assessed using standard assays available in the art and/or described herein, such as those set forth in the Examples (e.g., ELISAs).

Prophylactic and Therapeutic Uses

Antibodies that binds Epo as described herein, can be used at a therapeutically useful concentration for the treatment of a disease or disorder associated with increased Epo levels and/or activity by administering to a subject in need thereof an effective amount of the antibodies or antigen binding fragments of the invention. The present invention provides a method of treating conditions or disorders associated with retinal vascular disease by administering to a subject in need thereof an effective amount of the antibodies of the invention. The present invention provides a method of treating conditions or disorders associated with diabetic retinopathy (DR) by administering to a subject in need thereof an effective amount of the antibodies of the invention. The present invention provides a method of treating conditions or disorders associated with macular edema administering to a subject in need thereof an effective amount of the antibodies of the invention. The invention also provides a method of treating diabetic macular edema (DME) by administering to a subject in need thereof an effective amount of the antibodies of the invention. The present invention further provides a method of treating proliferative diabetic retinopathy (PDR) by administering to a subject in need thereof an effective amount of the antibodies of the invention. Still further, the present invention provides methods for treating age-related macular edema (AMD), retinal vein occlusion (RVO), angioedema, multifocal choroiditis, myopic choroidal neovascularization, and/or retinopathy of prematurity, by administering to a subject in need thereof an effective amount of the antibodies of the invention. The invention also provides methods of treating beta thelassemia and/or cancer.

The invention also relates to a composition comprising an isolated antibody or antigen binding fragment thereof as described herein for use in treating a disease or disorder associated with increased Epo levels and/or activity. The invention further relates to a composition comprising an isolated antibody or antigen binding fragment thereof as described herein for use in treating conditions or disorders associated with retinal vascular disease. The invention further relates to a composition comprising an isolated antibody or antigen binding fragment thereof as described herein for use in treating conditions or disorders associated with diabetic retinopathy (DR). The invention further relates to a composition comprising an isolated antibody or antigen binding fragment thereof as described herein for use in treating conditions or disorders associated with macular edema, diabetic macular edema (DME), and/or proliferative diabetic retinopathy (PDR). The invention still further relates to a composition comprising an isolated antibody or antigen binding fragment thereof as described herein for use age-related macular edema (AMD), retinal vein occlusion (RVO), angioedema, multifocal choroiditis, myopic choroidal neovascularization, and/or retinopathy of prematurity. The invention further relates to a composition comprising an isolated antibody or antigen binding fragment thereof as described herein for use in treating beta thelassemia and/or cancer. More specifically, the isolated antibody or antigen binding fragment thereof as described herein for use in treating a disease or disorder associated with increased Epo levels and/or activity, may be any one of the antibodies or antigen binding fragments described herein, in addition to those described in Table 1. Still further, the isolated antibody or antigen binding fragment thereof as described herein for use in treating conditions or disorders associated with retinal vascular disease, may be any one of the antibodies or antigen binding fragments described herein, in addition to those described in Table 1. The antibodies of the invention can be used, inter alia, to prevent progression of conditions or disorders associated with retinal vascular disease (for example, DR, DME, NPDR, PDR, age-related macular degeneration (AMD), retinal vein occlusion (RVO), angioedema, multifocal choroiditis, myopic choroidal neovascularization, and/or retinopathy of prematurity), to treat or prevent macular edema associated with retinal vascular disease, to reduce the frequency of Lucentis® (RTM) injection, and to improve vision lost due to retinal vascular disease progression. The antibodies of the invention can also be used in combination with anti-VEGF therapies for the treatment of patients with retinal vascular disease.

In one aspect, the invention relates to a method of inhibiting Epo-dependent cell proliferation wherein the method includes the step of contacting Epo (e.g., contacting Epo in a subject) with an effective amount of a composition comprising the isolated antibody or antigen binding fragments thereof described herein; in particular, the composition can comprise the antibody NVS1, NVS2, NVS3, or NVS4. In one aspect, the method comprises contacting a cell (e.g., a cell comprising Epo) with a composition comprising the isolated antibody or antigen binding fragment thereof as described herein. The invention also relates to a composition comprising an isolated antibody or antigen binding fragment thereof as described herein for use to inhibit Epo-dependent cell proliferation in a subject. It is contemplated that the cell is a human cell. The cell could be a B cell. It is further contemplated that the cell is in a subject. It is also contemplated that the cell is in the eye of the subject. It is still further contemplated that the subject is human.

Cell proliferation can be measured by, for example, slit-lamp bio-microscopt, optical coherence tomography, color fundus photography, and fluorescein angiography (Heng et al. Diabet. Med. 2013 June; 30(6):640-50). In addition, the ability of an antibody or antigen binding fragment described herein to inhibit Epo-dependent cell proliferation can be measured using an assay such as the F36E, or Ba/F3-EpoR cell proliferation assay described below.

The invention also relates to a method of inhibiting Epo-dependent cell signalling wherein the method includes the step of contacting Epo with an effective amount of a composition comprising the isolated antibody or antigen binding fragments thereof described herein to prevent Epo from interacting with a receptor on a cell surface. In one aspect, the method comprises contacting a cell comprising Epo with a composition comprising the isolated antibody or antigen binding fragment thereof as described herein. The invention also relates to a composition comprising an isolated antibody or antigen binding fragment thereof as described herein for use to inhibit Epo-dependent cell signalling in a subject. It is contemplated that the cell is a human cell. It is further contemplated that the cell is in a subject. It is also contemplated that the cell is in the eye of the subject. It is still further contemplated that the subject is human.

Binding of Epo to the EpoR induces signaling via JAK2 kinases that lead to activation of downstream signaling pathways that include phosphatidyl-inositol 3-kinase (PI- 3K)/Akt, MAP kinase, STAT5 and protein kinase C (Jelkmann, 2007; Jelkmann, 2004). Epo or the Epo receptor (EpoR) have been reported to be produced endogenously by different cell types such as endothelial cells, smooth muscle cells, and CNS cells (Ogunshola and Bogdanova, 2013). Activation of EpoR upon binding of Epo can trigger downstream signalling pathways leading to different activities such as calcium transport (Korbel et al., 2004), cell survival (Velly et al., 2010), neuroprotection (Grimm et al., 2002), and angiogenesis (Ribatti, 2010; Ribatti et al., 2003). Accordingly, inhibition of Epo-dependent cell signaling can be determined by measuring the activity of one or more of these signaling pathways. For example, inhibition of Epo-dependent cell signaling can be determined by measuring JAK2 kinase, PI-3K/Akt, MAP kinase, STAT5 or protein kinase C. Methods for measuring these signaling pathways are known in the art and kits for measuring such pathway activity are commercially available. In addition, inhibition of Epo-dependent cell signaling can be determined by measuring cell proliferation as described above. Cell proliferation can be in a subject (e.g., angiogenesis), or can be measured using an assay such as the F36E, or Ba/F3-EpoR cell proliferation assay described below. In one aspect, Epo-dependent cell signaling is statistically significantly ($p<0.05$) decreased in the presence of an antibody described herein, relative to control.

The invention also relates to a method of inhibiting Epo-dependent cell proliferation or signalling wherein the method includes the step of contacting Epo with an effective amount of a composition comprising the isolated antibody or antigen binding fragments thereof described herein to prevent Epo from interacting with a receptor on a cell surface. It is contemplated that the cell is a B cell. It is contemplated that the cell is a human cell.

The invention also relates to a method of inhibiting Epo binding to the Epo receptor wherein the method includes the step of contacting Epo (e.g., contacting Epo in a subject) with an effective amount of a composition comprising the isolated antibody or antigen binding fragments thereof described herein; in particular, the composition can comprise the antibody NVS1, NVS2, NVS3, or NVS4. The invention also relates to a composition comprising an isolated antibody or antigen binding fragment thereof as described herein for use to inhibit Epo binding to the Epo receptor on a cell of a subject; in particular, the composition can comprise the antibody NVS1, NVS2, NVS3, or NVS4. It is contemplated that the cell is a human cell. It is further contemplated that the cell is in a subject. It is also contemplated that the cell is in the eye of the subject. It is still further contemplated that the subject is human. Inhibition of Epo binding to the Epo receptor can be measured as described by Khankin et al. PLoS ONE, 2010 5:e9246

Treatment and/or prevention of retinal vascular disease and macular edema associated with retinal vascular disease can be determined by an ophthalmologist or health care professional using clinically relevant measurements of visual function and/or retinal anatomy. Treatment of conditions or disorders associated with retinal vascular disease means any action (e.g., administration of an anti-Epo antibody described herein) that results in, or is contemplated to result in, the improvement or preservation of visual function and/or retinal anatomy. In addition, prevention as it relates to conditions or disorders associated with retinal vascular disease means any action (e.g., administration of an anti-Epo antibody described herein) that prevents or slows a worsening in visual function, retinal anatomy, and/or a retinal vascular disease parameter, as defined herein, in a patient at risk for said worsening.

Visual function may include, for example, visual acuity, visual acuity with low illumination, visual field, central visual field, peripheral vision, contrast sensitivity, dark adaptation, photostress recovery, color discrimination, reading speed, dependence on assistive devices (e.g., large typeface, magnifying devices, telescopes), facial recognition, proficiency at operating a motor vehicle, ability to perform one or more activities of daily living, and/or patient-reported satisfaction related to visual function.

Exemplary measures of visual function include Snellen visual acuity, ETDRS visual acuity, low-luminance visual acuity, Amsler grid, Goldmann visual field, Humphrey visual field, microperimetry, Pelli-Robson charts, SKILL card, Ishihara color plates, Farnsworth D15 or D100 color test, standard electroretinography, multifocal electroretinography, validated tests for reading speed, facial recognition, driving simulations, and patient reported satisfaction. Thus, treatment of vascular disease and/or macular edema can be said to be achieved upon a gain of or failure to lose 2 or more lines (or 10 letters) of vision on an ETDRS scale. In addition, treatment of vascular disease and/or macular edema can be said to occur where a subject exhibits at least a 10% an increase or lack of 10% decrease in reading speed (words per minute). In addition, treatment of vascular disease and/or macular edema can be said to occur where a subject exhibits at least a 20% increase or lack of a 20% decrease in the proportion of correctly identified plates on an Ishihara test or correctly sequenced disks on a Farnsworth test. Further, treatment of retinal vascular disease and/or macular edema, can be said to occur if a subject has, for example, at least 10% decrease or lack of a 10% or more increase in time to a pre-specified degree of dark adaptation. In addition, treatment of retinal vascular disease and/or macular edema can be said to occur where a subject exhibits, for example, at least a 10% reduction or lack of a 10% or more increase in total area of visual scotoma expressed as a visual angle determined by a qualified health care professional (i.e., ophthalmologist).

Undesirable aspects of retinal anatomy that may be treated or prevented include, for example, microaneurysm, macular edema, cotton-wool spot, intraretinal microvascular abnormality (IRMA), capillary dropout, leukocyte adhesion, retinal ischemia, neovascularization of the optic disk, neovascularization of the posterior pole, iris neovascularization, intraretinal hemorrhage, vitreous hemorrhage, macular scar, subretinal fibrosis, and retinal fibrosis, venous dilation, vascular tortuosity, vascular leakage. Thus, treatment of, for example, macular edema can be determined by a 20% or more reduction in thickness of the central retinal sub-field as measured by optical coherence tomography.

Exemplary means of assessing retinal anatomy include funduscopy, fundus photography, fluorescein angiography, indocyanine green angiography, optical coherence tomography (OCT), spectral domain optical coherence tomography, scanning laser ophthalmoscopy, confocal microscopy, adaptive optics, fundus autofluorescence, biopsy, necropsy, and immunohistochemistry. Thus, vascular disease and/or macular edema can be said to be treated in a subject upon a 10% reduction in leakage area as determined by fluorescein angiography.

Subjects to be treated with therapeutic agents of the present invention can also be administered other therapeutic agents with known methods of treating conditions associated with diabetes mellitus, such as all forms of insulin and anti-hypertensive medications.

Treatment and/or prevention of ocular disease such as age-related macular degeneration (AMD), retinal vein occlusion (RVO), angioedema, multifocal choroiditis, myopic choroidal neovascularization, and/or retinopathy of prematurity can be determined by an ophthalmologist or health care professional using clinically relevant measurements of visual function and/or retinal anatomy by any of the measures described above. Although the measures described herein don't apply to each and every ocular disease herein, one of skill in the art would recognize the clinically relevant measurement of visual function and/or retinal anatomy that could be used to treat the given ocular disease.

When the therapeutic agents of the present invention are administered together with another agent, the two can be administered sequentially in either order or simultaneously. In some aspects, an antibody of the present invention is administered to a subject who is also receiving therapy with a second agent (e.g., Lucentis®). In other aspects, the binding molecule is administered in conjunction with surgical treatments.

Suitable agents for combination treatment with Epo binding antibodies include agents known in the art that are able to modulate the activities of VEGF, VEGF receptors, other receptor tyrosine kinase inhibitors, or other entities that modulate HIF-1 mediated pathways. Other agents have been reported to inhibit these pathways include ranibizumab, bevicizumab, pegaptanib, aflibercept, pazopanib, sorafinib, sunitinib, and rapamycin. Combination treatments with anti-inflammatory agents such as corticosteroids, NSAIDS, and TNF-α inhibitors could also be beneficial in the treatment of retinal vascular disease and macular edema, for example, diabetic retinopathy and DME.

A combination therapy regimen may be additive, or it may produce synergistic results (e.g., reductions in retinopathy severity more than expected for the combined use of the two agents). In some embodiments, the present invention provide a combination therapy for preventing and/or treating retinal vascular diseases and macular edema, specifically, diabetic retinopathy, including DME and/or PDR as described above with an Epo binding antibody of the invention and an anti-angiogenic, such as anti-VEGF agent.

Pharmaceutical Compositions

The invention provides pharmaceutical compositions comprising the Epo-binding antibodies (intact or binding fragments) formulated together with a pharmaceutically acceptable carrier. The compositions can additionally contain one or more other therapeutic agents that are suitable for treating or preventing, for example, diabetic retinopathy. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravitreal, intravenous, intramuscular, intraperitoneal, or subcutaneous, or administered proximal to the site of the target. The pharmaceutically acceptable carrier should be suitable for intravitreal, intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the Epo-binding antibody is employed in the pharmaceutical compositions of the invention. The Epo-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of a retinal vascular disease described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.01 to 15 mg/kg, of the host body weight. For intravitreal administration with an antibody, the dosage may range from 0.1 mg/eye to 10 mg/eye. More specifically, the dose may range from 1 mg/eye to 9 mg/eye, 2 mg/eye to 8 mg/eye, 3 mg/eye to 7 mg/eye, 4 mg/eye to 6 mg/eye, or 4.5 mg/eye to 5.5 mg/eye. In certain instances the does may be 0.1 mg/eye, 0.2 mg/eye, 0.3 mg/eye, 0.4 mg/eye, 0.5 mg/eye, 0.6 mg/eye, 0.7 mg/eye, 0.8 mg/eye, 0.9 mg/eye, 1 mg/eye, 2 mg/eye, 3 mg/eye, 4 mg/eye, 5 mg/eye, 6 mg/eye, 7 mg/eye, 8 mg/eye, 9 mg/eye, or 10 mg/eye. An exemplary treatment regime entails systemic administration once per every two weeks or once a month or once every 3 to 6 months. An exemplary treatment regime entails systemic administration once per every two weeks or once a month or once every 3 to 6 months, or as needed (PRN).

Antibody is usually administered on multiple occasions. Intervals between single dosages can be weekly, monthly or yearly. Intervals can also be irregular as indicated by measuring blood levels of Epo-binding antibody in the patient. In addition alternative dosing intervals can be determined by a physician and administered monthly or as necessary to be efficacious. Efficacy is based on lesion growth, rate of Lucentis® rescue, retinal thickness as determined by Optical Coherence Tomography (OCT), and visual acuity. In some methods of systemic administration, dosage is adjusted to achieve a plasma antibody concentration of 1-1000 µg/ml and in some methods 25-500 µg/ml. Alternatively, antibody can be administered as a sustained release formulation, in which case less frequent administration is required. Dosage and frequency vary depending on the half-life of the antibody in the patient. In general, humanized antibodies show longer half-life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the invention but not to limit its scope. Other variants of the invention will be readily apparent to one of ordinary skill in the art and are encompassed by the appended claims.

Example 1: Generation of Affinity Matured Epo Antibodies

A fully human phage display library was used to generate the Epo binding antibodies described herein.

Biotinylated and non-biotinylated human and cynomolgus Epo were used in solution and solid phase pannings. Standard panning were performed as well as RapMAT approaches (Prassler et al., (2009) Immunotherapy 1(4):571-583). Following secondary screening and RapMAT panning, clones were selected for sequence analysis and a set of 8 antibodies were selected for conversion to a FabCys format, germlining, pI optimization and removal of deamidation sites. FabCys generation was accomplished with a proprietary RapCLONE® method. RapCLONE® was performed as a two-step method for convenient and efficient conversion of a large amount of Fab clones into the IgG and FabCys format. In a first cloning step, a eukaryotic expression cassette was introduced into the expression vectors pMORPH®x11 (for HuCAL PLATINUM®) via BsiWI/MfeI (for κ pools) or HpaI/MfeI (for λ pools) digestion and subsequent ligation. This was followed by a second cloning step, in which the Fab pools containing the expression cassette were digested using EcoRV/BlpI (κ and λ pools) and subsequently cloned into the pMorph®4_IgG1f or pMorph®4_h_FabCys acceptor vector for expression in mammalian cells. For this project, RapCLONE® was applied only on unique, sequenced and characterized Fab. Therefore all clones were recovered after RapCLONE®.

Low pIs (<8.2) are generally associated with poor biophysical properties including stability and aggregation. 8 final candidates (HCDR3 unique clones) were selected for germlining, pI optimization and removal of de-amidation sites leading to a total of 12 germlined variants. 12 VL-genes were synthesized (two for 11317, 11324, 11331 and 11345) and one VH (11324). Possibly due to early de-selection of candidates with PTMs, only 11317 (VL), 11332 (VL) and 11380 (VH) contained de-amidation sites that were removed with the germlining. Germlining was in general done to the closest germline. To increase the pI, the lambda germline 3h was chosen for 6 of the candidates instead of or in addition to the closest germline 3r. Additionally lambda 3j variants were constructed for three candidates to minimize risk (11317, 11331 and 11345).

| Initial Antibody | PTM-modifications* | pI modifications** | Final FabCys | Final pI of FabCys |
|---|---|---|---|---|
| 11317 | 3j, S96T | NA | NVS4 | 9.4 |
| 11319 | 3h | Q105R | NVS1 | 8.3 |
| 11331 | 3h | Q1E | NVS2 | 8.8 |
| 11380 | 3h | Q105R, S33T | NVS3 | 8.3 |

NA, Not applicable
*All PTM-modification occured in VL,
**pI modifications occured in VH As mentioned above, the pI of a protein is a key determinant of the overall biophysical properties of a molecule. The anti-Epo Fabs identified from the phage display library had pIs lower than 8.2. To improve the manufacturing properties, the antibodies were specifically engineered to increase their pI and improve their drug-like properties. Increasing the pI of the anti-Epo Fabs improved their solubility, enabling the Fabs to be formulated at higher concentrations (>100 mg/ml). Formulation of the Fabs at high concentrations (e.g. >100 mg/ml) offers the advantage of being able to administer higher doses of the Fabs into eyes of patients via intravitreal injections, which in turn may enable reduced dosing frequency, a significant advantage for treatment of chronic ocular diseases including, but not limited to wet AMD and diabetic retinopathy.

The resulting Fabs are shown in Table 1 (NVS1, NVS2, NVS3, and NVS4).

Example 2: Characterization of Optimized Antibodies

The following example describes methods that may be used to measure antibody affinity. These and other methods of measuring binding affinity are known in the art.

Affinity Determination

Antibody affinity for Epo was measured by surface plasmon resonance (SPR) using a Biacore® T200 (Biacore) and solution equilibrium titration (SET). Explanations of each technology and corresponding mean results for Epo binding are described below. Modelling assumptions take into account concentrations of Epo in the system, kinetics of Epo biosynthesis and half-life, as well as the desired dosing schedule, and suggest that a Fab with an affinity of less than 50 pM for Epo is sufficient to lower levels of free Epo.

Biacore Determination

The kinetics of an interaction, i.e. the rates of complex formation ($k_a$) and dissociation ($k_d$), can be determined from the information in a sensorgram. If binding occurs as sample passes over a prepared sensor surface, the response in the sensorgram increases. If equilibrium is reached a constant signal will be seen. Replacing sample with buffer causes the bound molecules to dissociate and the response decreases. Biacore evaluation software generates the values of $k_a$ and $k_d$ by fitting the data to interaction models.

Three flow cells were utilized for the method run. Flow cell 1 (fc1) served as the reference, where no Epo Fab was captured, to assess for non-specific binding of the Epo to the antibody coated chip surface. Both capture and binding steps were carried out on flow cells 2-4.

Capture step: In order to achieve an Rmax of 20, the capture level of anti-hu Fab on fc2-4 was approximately 50RL. Anti-hu Fab at a concentration of 1 ug/ul, flowed over Fc2-4 at a flow rate of 10 µl/min.

The calculations for the relative Rmax is as follows:

$$\text{Fabs:} R_{max} = R_L * (MW_{analyte}/MW_{ligand}) * \text{stoichiometry}$$
$$20 = RL * (21.4/50) * 1 = 50RL$$

The analyte started at concentrations of 20 nM and included 8 1:2 dilutions with a duplicate at 2.5 nM for the long and short dissociation. The analyte was run at a flow rate of 60 µl/min for 240 seconds. Dissociation times were set at 4000 seconds and 600 seconds. Dissociation time was set at 4000 seconds for 10 nM, 2.5 nM and 0.3125 nM analyte concentrations for NVS2 and NVS4. After the sample injection, there was a wash step with the regeneration buffer.

Regeneration was performed at the end of each cycle on all flow cells. Regeneration condition for this method was 1% Phosphoric acid with 10% sodium Hydroxide at 60 ul/min for 100 seconds.

All other running conditions were carried out at 25° C. in 1×HBS-EP+ buffer (Biacore cat#BR-1006-69). The resulting signals were adjusted by double referencing, thus subtracting the refraction index values from the reference flow cell and the binding step with no analyte. Data was collected at 10 Hz and analyzed using the Biacore® T100 Evaluation Software Version 1.1 (GE Healthcare). This program uses a global fitting analysis method for the determination of rate and affinity constants for each interaction.

The results of the Biacore binding kinetics determination are shown in Table 2. As shown the antibodies described herein exhibited high affinity binding to human Epo, with $K_D$ values typically less than or equal to 40 pM.

TABLE 2

Affinity Binding of Epo Antibodies (Biacore)

| | $K_D$ (pM) | | | |
|---|---|---|---|---|
| Epo | NVS2 | NVS3 | NVS4 | NVS1* |
| Human | 34.2 | 37 | 27.1 | 11 |
| Human-darbapoetin | 23.5 | ND | 18.1 | ND |
| Cyno | 78.7 | 49 | 76.0 | 31 |
| Mouse | 44.9 | 1 | 30.5 | 22 |
| Rat | 56.6 | 38 | 34.4 | 41 |
| Rabbit | 5160 | 674 | ND | 661 |

ND: not determined
*Data shown for NVS1 is single datapoint

SET Determination

In contrast to kinetic assays using sensor surfaces, such as SPR, SET is a method which determines affinities in solution. It is an equilibrium measurement that does not deliver kinetic data.

In SET, a constant amount of antibody is incubated with different concentrations of antigen until equilibrium is reached. The concentration of free antibody in the equilibrated solution is determined by applying the solution on an antigen coated MSD™ plate (Meso Scale Discovery™) followed by incubation with an ECL-labeled secondary antibody and measurement of signal intensity. At low antigen concentrations, a strong signal is achieved (high concentration of free antibody which binds to the antigen on the plate) whereas for high antigen concentration, the antibody is completely antigen-captured, resulting in a low signal. If a sufficient number of antigen concentrations in a matching range are available, the titration curve allows for a reasonable determination of the affinity, using the appropriate fit model. For a complete titration, antigen concentrations of at least 10-fold higher than the anticipated $K_D$ have to be applied. The constant concentration of antibody applied in the assay should be in the range of, or below, the $K_D$ (Table 3).

For $K_D$ determination by SET, monomer fractions of antibody protein were used (at least 90% monomer content, analyzed by analytical SEC; Superdex75 (Amersham Pharmacia) for Fab, or Tosoh G3000SWXL (TOSOH BIOSCIENCE) for IgG, respectively).

Affinity determination in solution was basically performed as described in the literature (Friguet et al. 305-19). In order to improve the sensitivity and accuracy of the SET method, it was transferred from classical ELISA to ECL based technology (Haenel et al., 2005).

Epo antibodies were diluted to a fixed concentration in incubation buffer (PBS with 2% BSA (Sigma cat#A4503) and 1% Tween20 and 1% Triton-X (Sigma cat#234729)), and added to a serial dilution (1:5) of Epo in incubation buffer.

Final Highest Concentration of Epo:
Human, Hu-darbapoetin, cynomolgus, mouse, rat=10 nM
Rabbit=100 nM
Final Concentrations of Fabs:
NVS2: 2 pM, except Rabbit=30 pM
NVS3: 2 pM, except Rabbit=5 pM
NVS4: 2 pM, except Rabbit=10 nM
NVS1: 2 pM
Samples were allowed to reach equilibrium by incubation at RT overnight.

Streptavidin-coated standard MSD plates (Meso-Scale Discovery, 384-well: MSD cat#L11SA) were blocked with 25 µl incubation buffer at RT for 1 hr. Plates were washed 3× in TBST buffer (25 mM TBS with 0.05% Tween20), and 0.1 µg/ml of biotinylated-Epo was added in 25 µl incubation buffer and incubated at RT for 1 hr. Plates were washed 3× in TBST buffer. Samples containing Fabs and Epo titration were added to the plate (25 µl), and incubated at RT for 15 min. Plates were washed 3× in TBST buffer. 25 µl detection antibody was added (Anti-Human (Goat) Sulfo-TAG, 1:1000 in incubation buffer, MSD cat#R32AJ-1), and incubated at RT for 60 min. Plates were washed 3× in wash buffer, and 50 µl of 1×MSD Read buffer T was added (with surfactant, MSD cat#R92TC-1). Plates were read on a MSD Spector Imager 6000.

Three experiments were performed on separate days, each data point in triplicate.

Data was analyzed using GraphPad Prism software v4, with background (an average of wells containing no Fab) subtracted from each value. X-axis values (concentration of Epo in solution) were transformed into log 10×.

KD values (KD) were fitted from the following model:

$$Y=(Top-((Top/(2\times Fab))\times((((10^x)+Fab)+KD)-((((((10^x)+Fab)+KD)\times(((10^x)+Fab)+KD))-((4\times(10^x))\times Fab))^0.5))))$$

Top=signal at antigen concentration=0
x=concentration of Epo in solution
Fab=constraint for Fab concentration was set to 1 pM Affinities of Epo Fabs were determined using the SET assay and resulting $K_D$ values ([pM] concentrations) are summarized in Table 3. NVS2 bound human, human-darbepeotin and cynomolgus Epo with a $K_D$ less than 10 pM. NVS2 also bound mouse Epo with a $K_D$ less than 50 pM and rat Epo with a $K_D$ less than 20 pM. NVS3 bound human, human-darbepeotin, cynomolgus, mouse and rat Epo with a $K_D$ less than 5 pM. NVS4 bound human, human-darbepoetin, cynomolgus, mouse and rat Epo with a $K_D$ less than 10 pM.

TABLE 3

Affinity Binding of Epo Antibodies (SET)

| Epo | $K_D$ (pM) | | | |
|---|---|---|---|---|
| | NVS2 | NVS3 | NVS4 | NVS1* |
| Human | 5.4 | 0.9 | 2.5 | 1.2 |
| Darbepoietin | 3.7 | 0.5 | 1.3 | ND |
| Cyno | 7.3 | 0.8 | 7.3 | 4.4 |
| Mouse | 37.0 | 2.5 | 7.8 | 16.1 |
| Rat | 12.7 | 1.2 | 12.7 | 5.4 |
| Rabbit | 3864.7 | 39.9 | 28670 | ND |

ND: not determined
*Data shown for NVS1 is single datapoint

Example 3: Inhibition of Epo Induced Cell Proliferation

Cells which are dependent on erythropoietin for growth and survival can be utilized to measure the potency of anti-Epo therapeutics by means of Epo-dependent proliferation inhibition (Chiba et al., 1991).

Example 3a: Ba/F3-EpoR Cell Proliferation Assay

This assay demonstrates the ability of Epo antibodies to inhibit Epo induced cell proliferation in mouse Ba/F3 cells expressing the Epo receptor (Ba/F3-EpoR cells). Ba/F3 cells are IL-3 dependent for growth and survival and have been shown to grow in an IL-3 independent manner upon transformation with various oncogenic tyrosine kinases. Upon stable transfection with EpoR, Ba/F3-EpoR cells became IL-3 independent. The mammalian expression plasmid pcDNA3.1 carrying human EpoR was transfected into Ba/F3 cells using the Amaxa nucleofection system (catalogue number VCA-1003, Amaxa GmbH) according to the manufacturers instructions using the Nucleofector device (Amaxa, Nucleofactor™ II).

Materials

| Materials | Description | Source | Catalog # |
|---|---|---|---|
| 384-well plate | Matrix 384-well microplate | ThermoScientific | 50823639 |
| 384-well plate | uClear-Plate Black, 384 well TC w/Lid | Greiner Bio-One | 7881091 |
| RPMI 1640 | | Invitrogen | 11875 |
| FBS | | Hyclone | SH30071.03 |
| Pen/Strep | | Invitrogen | 15140 |
| Hygromycin B | | Invitrogen | 10687010 |
| Epo | | Genway | 10-663-45072 |
| Darbepoietin | | Sandoz | CAS #: 209810-58-2 |
| Ba/F3-EpoR cells | | Described herein | |
| Cell Titer Blue | | Promega | G8081 |

Cell Maintenance
Growth Medium: RPMI1640/10% FBS/1% Pen-Strep/100 µg/ml Hygromycin B/1 U/ml Epo
Assay Medium: RPMI1640/10% FBS/1% Pen-Strep/100 µg/ml Hygromycin B Ba/F3-EpoR cells were maintained in growth medium (RPMI1640/10% FBS/1% Pen-Strep/100 µg/ml Hygromycin B/1 U/ml Epo). Cells were split at ~1e6 cells/ml (every 3-4 days) down to 0.4-0.6e5 cells/ml.

Epo Induced Cell Proliferation Assay
1. A day before the experiment, Ba/F3-EpoR cells were prepared by centrifugation to remove growth medium, following which the cells were resuspended in assay medium (RPMI1640/10% FBS/1% Pen-Strep/100 µg/mL Hygromycin B) which does not contain Epo.
2. On the day of experiment, cells were washed 2-3 times in assay medium (centrifuge 1000 rpm, 5 min) and resuspended in assay medium at 1.25×10⁵ cells/ml.
3. 2500 cells were added to each assay well in a 384-well black plate (clear bottom, TC treated).
4. Epo was serially diluted in a 384-well microplate with assay media such that the final concentration of Epo was two-fold higher than desired final concentration.
5. 20 µl of serially diluted Epo (in triplicate) was added in triplicate to sample wells containing Ba/F3-EpoR cells of 384-well black plate.
6. The plate was spun in a centrifuge at 1000 rpm for 30-60 seconds and incubated for 48 hrs at 37° C., 5% $CO_2$.
7. Four hours prior to endpoint, 8 µl Cell Titer Blue was added to all wells and re-incubated at 37° C., 5% $CO_2$.
8. Four hours later, the plate was read on a Beckman Coulter Paradigm with Paradigm Multimode SW, or comparable scanner.
9. Epo stimulated proliferation of Ba/F3-EpoR cells 4-fold over baseline. Epo stimulated Ba/F3-EpoR with an average $EC_{50}$ of 11.2 pM and range of 10 pM and 26 pM.
10. Anti-Epo antibodies were serially diluted in triplicate in a 384-well microplate containing 4 ng/ml Epo in assay medium and incubated for 30 minutes at room temperature.

11. 20 µl/well of the above Epo/anti-Epo antibody mixture was added to the 384-well black walled plate previously seeded with 2500 BaF3/EpoR cells per well.
12. Post-incubation plates were processed as outlined in steps 7-9 above Results Epo antibodies inhibited Ba/F3-EpoR cells proliferation in the presence of 1 ng/ml Epo after 48 hrs. Antibodies inhibited Ba/F3-EpoR cell proliferation with an $IC_{50}$ less than or equal to 350 pM.

TABLE 4

| Assay | $IC_{50}$ (pM) | | | | |
|---|---|---|---|---|---|
| | NVS2 | NVS3 | NVS4 | NVS1 | Epo26 |
| Ba/F3 Assay | 112.0 | 76.3 | 173.1 | 338 | 590 |

Example 3b: F36E Cell Proliferation Assay

F36E cells are highly dependent on Epo for proliferation. Stimulation with Epo using the methods described above typically results in a greater then 6-fold signal over baseline. The EC50 of this curve is 7 pM.

Protocol for Neutralization of Epo Induced F36E Cell Proliferation Assay

A proliferation assay using the F36E cell line, an Epo-dependent lymphocyte-like immortalized cell line derived from a parental bone marrow cell line, was used for screening anti-Epo therapeutic antibodies and to select candidates for development.

Materials

| Materials/reagents | Source | Catalog # |
|---|---|---|
| 384 well polystyrene cell culture microplates, black | Greiner Bio One | 781091 |
| 384 well polypropylene microplate without lid | Greiner Bio One | 781280 |
| RPMI 1640 | Invitrogen | 11875 |
| FBS | Hyclon | SH30071.03 |
| Pen/Strep | Invitrogen | 15140 |
| Darbepoietin | Sandoz | CAS #: 209810-58-2 |
| F36E cells | Riken Cell Bank | RCD0776 |
| Cell Titer Blue | Promega | G8081 |
| Epo26 anti-human Epo monoclonal antibody | Stem Cell Tech | 01350 |

Cell Maintenance

Darbepoietin, a recombinant hyperglycosylated human Epo, was used for cell maintenance and proliferation assays described herein. Darbepoietin stimulates proliferation in F36E cells with a comparable EC50 to recombinant human Epo (63.2 pg/ml darbepoietin and 81.25 pg/ml erythropoietin; see LU-15432, pg. 44). F36E cells were maintained in growth media (RPMI1640/5% FBS/1% Pen-Strep/5.2 U/ml dEpo) at minimum density 0.25e6 cells per ml to maximum density 1.0e6 cells per ml up to 10 passages.

Epo Induced Proliferation Assay Protocol
1. Epo was diluted in assay media (RPMI1640/5% FBS/1% Pen-Strep) to 4 ng/ml, 4x-fold desired final concentration.
2. Anti-Epo antibody was diluted in assay media to 200 nM, 4x final concentration, and this concentration was serially diluted in assay media for six points. Dilution was repeated for a positive reference antibody (e.g.: Epo26) and a negative reference antibody (e.g.: anti-chicken lysozyme monoclonal antibody).
3. 7.5 ul diluted dEpo and 7.5 ul anti-Epo antibody serial dilutions were mixed in 384-well polypropylene microplate, in triplicate, and incubated at room temperature for 30 minutes.
4. F36E cells (2e6 per 384-well plate) were pelleted, growth media was aspirated and cells were washed once in assay media (centrifuge 1200 rpm, 5 min), then resuspended in assay media to 3.33e5 cells/ml.
5. 15 µl/well cells (5,000 cells/well) were added to all wells in 384-well polystyrene cell culture plate.
6. 15 ul antibody-Epo mixture was added to cells.
7. Incubated 68 hrs at 37° C., 5% CO2.
8. 8 µl Cell Titer Blue was added per well and incubated at 37° C., 5% CO2 for 4 hours.
9. Fluorescence was measured at 560(20)Ex/590(10)Em on a Fluoroskan Ascent Microplate Fluorometer or comparable scanner.
10. The average RFU+/−standard deviation vs. nM antibody was plotted and IC50 determined by non-linear regression curve fit in Graph Pad Prizm software.

Results

Anti-Epo antibodies inhibited F36E cell proliferation with an $IC_{50}$ less than or equal to 200 pM.

TABLE 5

| Assay | $IC_{50}$ (pM) | | | | |
|---|---|---|---|---|---|
| | NVS2 | NVS3 | NVS4 | NVS1 | Epo26 |
| F36E Assay | 144.1 | 88.7 | 182.7 | 175 | 590 |

Example 4: Epitope Binding

Synthetic Peptide & Peptide Trunctation Studies

Synthetic peptides corresponding to structural domains of human Epo (hEpo), domain truncations of hEpo, or chimeric molecules containing portions of hEpo and human thrombopoietin (TPO) were synthesized or expressed recombinantly. Positive binding to the synthetic peptides indicated that residues contained in that domain of Epo were involved in binding to the anti-Epo antibody. For the truncated proteins, loss of binding indicated the involvement of the truncated portion in binding to the anti-Epo antibody. However, the loss of binding did not preclude the possibility that the truncation altered the structure of the remaining protein significantly so as to affect binding to the anti-Epo antibodies. The human Epo-human TPO chimeras enabled maintenance of structure while still allowing epitope mapping. Loss of binding to a variant that contained a portion of hTPO indicated that the homologous region in hEpo was important for binding to the anti-Epo antibody.

Peptide Epitope Mapping of Anti-Erythropoietin Antibodies

The following six peptides (Table 6), corresponding to the helices of erythropoietin were synthesized.

TABLE 6

| Peptide | Sequence | EPO domain |
|---|---|---|
| 1 | SEQ ID NO: 93 RLICDSRVLERYLLE AKEAENITTG | Helix A |

TABLE 6-continued

| Peptide | Sequence | EPO domain |
|---|---|---|
| 2 | SEQ ID NO: 94 ITVPDTKVNFYAWKRM | Loop A-B |
| 3 | SEQ ID NO: 95 EVGQQAVEVWQGLALL SEAVLRGQALLVNS | Helix B |
| 4 | SEQ ID NO: 90 EPLQLHVDKAVSGLRSLT TLLRALGAQKEAISPPD | Helix C |
| 5 | SEQ ID NO: 91 DKAVSGLRSLTTLLRAL | Helix C |
| 6 | SEQ ID NO: 96 TFRKLFRVYSNFLRGKL KLYTGEACR | Helix D |

Assay Set Up
1. 25 ul of peptide in PBS (5 ug/ml) was coated on 384 well MSD standard plate (Mesoscale Discovery, Cat. No. L21XA-4) overnight.
2. The plate was blocked with 90 ul of PBS+5% BSA/0.1% Tween-20/0.1% TritonX-100 for 4 hours.
3. 500 nM Morphosys Epo Fab in diluents of PBS+2% BSA/0.1% Tween-20/0.1% TritonX-100 was added to plate and incubated for 1 hour.
4. The plate was washed and incubated with Sulfo-tag anti-human IgG (Meso Scale Discovery, Cat. No. R32AJ-1) for Epo Fabs or species appropriate for reference proteins/antibodies (1 hr)
5. Plate was washed and MSD Read Solution (Meso Scale Discovery, Cat. R92TC-1) was added.
6. Read plate Epitope Mapping of Anti-Erythropoietin Antibodies with Truncated Variants of Erythropoietin
Epo Variant 1: Helix A
Epo Variant 2: Helix A, Loop A-B
Epo Variant 3: Helix A, Loop A-B, Helix B
Epo Variant 4: Helix A, Loop A-B, Helix B, Loop B-C, Helix C
Epo Variant 5: Full length erythropoietin Assay Set Up
1. Plate was coated with biotinylated HEK293 expressed Epo variants on standard streptavidin 384 well plate plate (Mesoscale Discovery, Cat. No. L21SA-1) overnight at 4° C.
2. The plate was blocked with 90 ul of PBS+5% BSA/0.1% Tween-20/0.1% TritonX-100 for 4 hours.
3. The place was washed and 500 nM Morphosys Epo Fab was added to the plate and incubated for 1 hour
4. The plate was washed and incubated with Sulfo-tag anti-human IgG (Meso Scale Discovery, Cat. No. R32AJ-1) for Epo Fabs or species appropriate for reference proteins/antibodies (1 hr)
5. The plate was washed and MSD Read Solution (Meso Scale Discovery, Cat. R92TC-1) was added.
6. Read plate Epitope Mapping of Anti-Erythropoietin Antibodies with Epo/Thrombopoietin (Tpo) and Rabbit/Human Epo Chimerics
Epo/Tpo Chimerics
Epo/Tpo Variant 1: Human Epo with Tpo Helix A
Epo/Tpo Variant 2: Human Epo with Tpo Loop A-B
Epo/Tpo Variant 3: Human Epo with Tpo Helix B
Epo/Tpo Variant 4: Human Epo with Tpo Helix C
Epo/Tpo Variant 5: Human Epo with Tpo Helix D
Rabbit/Human Epo Chimerics
Rb/Hu Epo Variant 1: Rabbit Epo with Human Helix A
Rb/Hu Epo Variant 2: Rabbit Epo with Human Loop A-B
Rb/Hu Epo Variant 3: Rabbit Epo with Human Helix B
Rb/Hu Epo Variant 4: Rabbit Epo with Human Loop B-C and Helix C
Rb/Hu Epo Variant 5: Rabbit Epo with Human Loop C-D
Rb/Hu Epo Variant 6: Rabbit Epo with Human Helix D Assay Set Up
1. 25 ul of Epo chimerics in PBS (2 ug/ml) were coated on a 384 well MSD standard plate (Mesoscale Discovery, Cat. No. L21XA-4) overnight at 4° C.
2. The plate was blocked with 90 ul of PBS+5% BSA/0.1% Tween-20/0.1% TritonX-100 for 4 hours.
3. 500 nM Morphosys Epo Fab in diluents of PBS+2% BSA/0.1% Tween-20/0.1% TritonX-100 was added to plate and incubated for 1 hour.
4. The plate was washed and incubated with Sulfo-tag anti-human IgG (Meso Scale Discovery, Cat. No. R32AJ-1) for Epo Fabs or species appropriate for reference proteins/antibodies (1 hr)
5. The plate was washed and MSD Read Solution (Meso Scale Discovery, Cat. R92TC-1) was added.
6. Read plate General Protocol
Standard capture 384-well MSD plates (Meso Scale Discovery) were coated with peptide (5 ug/ml in PBS, New England Peptide LLC) or Epo chimerics (2 ug/ml in PBS) and incubated overnight at 4° C. Biotinylated truncated Epo variants (2 ug/ml in PBS) were coated on standard streptavidin capture 384-well MSD plates overnight. After washing the plates 1× with TBST (Thermo Scientific, Cat. No. Cat. No. 28360), the plates were blocked in diluent (PBS, 5% BSA, 0.1% Tween-20, 0.1% TritonX-100) for 4 hours at room temperature. Plates were washed 3× in TBST. Five hundred nanomolar of anti-erythropoietin fabs were added to the peptide/Epo variants precoated MSD plates for 1 hour. Plates were washed 3× in TBST and anti-Human IgG-Sulfotag (1 ug/ml, Meso Scale Discovery, Cat. No. R32AJ-1) was added and incubated for 60 minutes. Plates were washed 3× in TBST and 1× Read Buffer T (Meso Scale Discovery, Cat. No. R92TC-1) was added. The plates were read on a MSD Spector Imager 6000 and data was analyzed using GraphPad Prism software v4.

Results:
Results indicated that the antibodies minimally bound to the following domains (Table 7). No antibodies bound to Helix C.

TABLE 7

| | Helix A | Loop A-B | Helix D |
|---|---|---|---|
| NVS1 | ++ | | + |
| NVS2 | | ++ | + |
| NVS3 | + | + | ++ |
| NVS4 | | | ++ |

(++) Dominant epitope;
(+) observed binding

Crystal Structure of Antibodies in Complex with Epo
Glycosylated, recombinant human Erythropoeitin (Epo) was received from LEK Pharmaceuticals, Inc.
Epo was de-glycosylated using Protein De-glycosylation Mix (New England Biolabs, cat #P6039S). 30 mg of hEpo was combined with 1 ml of Protein Deglycosylation Mix and incubated at 37° C. for 1 hour at which point deglycosylation was incomplete as determined by SDS-PAGE. An additional 0.5 ml of Protein De-glycosylation Mix was then added to Epo and incubated for a further 1 hour at 37° C. Gel analysis showed near complete deglycosylation of Epo. This protein was then further purified using a 120 ml Superdex75 column (GE Healthcare, cat #28-9893-33) equilibrated in 25 mM HEPES pH 7.5, 150 mM NaCl. Elution fractions containing the highest level of de-glycosylation of hEpo were pooled. Protein complexes were formed by combining 5 mg of de-glycosylated Epo with 7 mg of NVS3, followed by incubation on ice for 1 hour. The protein complex mix was then concentrated and applied to a 120 ml Superdex 75, equilibrated in 25 mM HEPES pH 7.5, 150 mM NaCl. Fractions containing SDS-gel evaluated stoichiometric ratios of Epo:NVS3 were pooled and concentrated to 19 mg/ml (concentration estimated by LCUV) (PRONOVA #27SN). Crystallization screens were set up using this concentrated Epo:NVS3 complex. Crystals were grown by the technique of sitting-drop vapor diffusion, with the drops containing equal volumes of protein and reservoir solution. Crystals formed at 4° C. with the following reservoir condition: 0.1M Hepes pH7.0, 12% PEG3350, 50 mM zinc acetate dehydrate. Crystals were frozen using the following cryoprotection solution: 0.1M Hepes pH7.0, 15% PEG3350, 50 mM zinc acetate dehydrate, 22% glycerol.

Epo:NVS3 complex crystal diffraction data were collected at beamline 17-ID at the Advanced Photon Source (Argonne National Laboratory, USA). Data were processed and scaled at 2.6 Å using autoPROC (Global Phasing, LTD) in space group C2 with cell dimensions a=125.57 Å, b=150.15 Å, c=163.84 Å, alpha=90°, beta=110.81°, gamma=90°. The Epo:NVS3 structure was solved by molecular replacement using Phaser (McCoy et al., (2007) J. Appl. Cryst. 40:658-674). The Fab from 3H0T structure in the PDB database (Berman 2000) was split into variable and constant domains, and the human erythropoietin structure Syed et. al., Nature. 1998 Oct. 1; 395(6701):511-6, PDB code 1EER, were used as search models.

The final model, which contains 3 molecule of the Epo: NVS3 complex per asymmetric unit, was built in COOT (Emsley & Cowtan (2004) Acta Cryst. 60:2126-2132) and refined to R and $R_{free}$ values of 23.0% and 26.7%, respectively, with an rmsd of 0.010 Å and 1.34° for bond lengths and bond angles, respectively, using PHENIX (Adams et al., Acta Cryst. D66, 213-221 (2010)).

The crystal structure of Epo:NVS3 was solved and refined to 2.6 Å. It revealed an asymmetric unit composed of three Epo:NVS2 protein complexes, each composed of one Fab bound to one Epo protein. Two of these complexes form a zinc mediated dimer and the third exhibits higher b-factors and weaker density. Interactions from the Fab to Epo were mediated by the complementarity determining region (CDR) loops from both the heavy and light chains of NVS3. Conformational changes of Epo when compared to 1EER were limited to loops distal from the Fab binding epitope, with an RMSD of 0.5 Å for all 144 aligned amino acids. The heavy and light chains of Fab NVS3 show typical immunoglobulin-like folds for the domains.

The crystals structure of Epo:NVS3 was used to identify the Epo epitope of the fragment antigen binding of NVS3. The interaction surface on Epo was formed primarily by residues comprising residue $Ser^9$, $Glu^{13}$, residues $Thr^{44}$ through $Arg^{53}$ and residues $Asn^{147}$ through $Arg^{162}$. These correspond to the secondary structure elements of Epo denoted as α-helix A, loop βA-αB and α-helix D. These residues formed the three-dimensional surface that is recognized by NVS3. Interactions included backbone interactions, solvent mediated interactions, and direct side-chain interactions.

TABLE 8

Epo interacting residues to NVS3 (Residues 44-53 disclosed as SEQ ID NO: 97)

| Amino Acid | Residue number | Contact Area (A2) | Exposed Area (A2) | Percentage buried (%) |
|---|---|---|---|---|
| Ser | 9 | 11.79 | 93.23 | 13 |
| Glu | 13 | 14.89 | 103.00 | 14 |
| Thr | 44 | 22.47 | 61.60 | 36 |
| Lys | 45 | 39.98 | 172.59 | 23 |
| Val | 46 | 34.38 | 55.22 | 62 |
| Asn | 47 | 48.17 | 81.92 | 59 |
| Phe | 48 | 83.76 | 129.76 | 65 |
| Tyr | 49 | 96.12 | 137.70 | 70 |
| Ala | 50 | 12.68 | 57.03 | 22 |
| Trp | 51 | 0.63 | 43.74 | 1 |
| Lys | 52 | 23.97 | 135.25 | 18 |
| Arg | 53 | 49.96 | 181.86 | 27 |
| Asn | 147 | 34.39 | 48.65 | 71 |
| Arg | 150 | 73.32 | 140.37 | 52 |
| Gly | 151 | 18.97 | 24.63 | 77 |
| Lys | 154 | 73.59 | 127.20 | 58 |
| Leu | 155 | 34.85 | 75.06 | 46 |
| Gly | 158 | 18.59 | 43.31 | 43 |
| Glu | 159 | 32.95 | 122.17 | 27 |
| Arg | 162 | 36.72 | 185.91 | 20 |

Epo residues that contain atoms in contact with NVS3 are listed in Table 9. Contact is defined to be within 5 Å of NVS3 to account for potential water mediated interactions.

TABLE 9

| Protein | Amino acid | Sequence position* | Epo Domain |
|---|---|---|---|
| Epo | S | 9 | Helix A |
| Epo | E | 13 | Helix A |
| Epo | T | 44 | Loop A-B |
| Epo | K | 45 | Loop A-B |
| Epo | V | 46 | Loop A-B |
| Epo | N | 47 | Loop A-B |
| Epo | F | 48 | Loop A-B |
| Epo | Y | 49 | Loop A-B |
| Epo | A | 50 | Loop A-B |
| Epo | W | 51 | Loop A-B |
| Epo | K | 52 | Loop A-B |
| Epo | R | 53 | Loop A-B |
| Epo | N | 147 | Helix D |
| Epo | R | 150 | Helix D |
| Epo | G | 151 | Helix D |
| Epo | K | 154 | Helix D |
| Epo | L | 155 | Helix D |
| Epo | G | 158 | Helix D |
| Epo | E | 159 | Helix D |
| Epo | R | 162 | Helix D |

*Sequence Position relative to SEQ ID NO: 81

Epo residues that contain atoms in contact with NVS2 are listed. Contact is defined to be within 5 Å of protein partner to account for potential water mediated interactions.

TABLE 10

| Protein | Amino acid | Sequence position* | Epo Domain |
|---|---|---|---|
| Epo | E | 23 | Helix A |
| Epo | D | 43 | Loop A-B |
| Epo | T | 44 | Loop A-B |
| Epo | K | 45 | Loop A-B |
| Epo | V | 46 | Loop A-B |
| Epo | N | 47 | Loop A-B |

TABLE 10-continued

| Protein | Amino acid | Sequence position* | Epo Domain |
|---|---|---|---|
| Epo | F | 48 | Loop A-B |
| Epo | Y | 49 | Loop A-B |
| Epo | A | 50 | Loop A-B |
| Epo | K | 52 | Loop A-B |
| Epo | R | 53 | Loop A-B |
| Epo | R | 131 | Helix D |
| Epo | R | 143 | Helix D |
| Epo | N | 147 | Helix D |
| Epo | R | 150 | Helix D |
| Epo | G | 151 | Helix D |
| Epo | K | 154 | Helix D |
| Epo | L | 155 | Helix D |
| Epo | E | 159 | Helix D |
| Epo | R | 162 | Helix D |

*Sequence Position relative to SEQ ID NO: 81

Example 5: In Vivo Model

Example 5a: Mouse Model of Ocular Edema

C57/Bl6 mice (Taconic) were sub-retinally injected with ssAAV2-EPO-eGFP (DR005) and ssAAV2-EGFP (TM003) (control). Mice were sacrificed three weeks (21 days) post-injection. The retinas were flat-mounted and the vessel caliber was measured.

Methods:

Subretinal Injection of ssAAV2-EPO-eGFP and ssAAV2-eGFP 8-week old C57/Bl6 mice were divided into two groups (10 mice each, 20 eyes/group) and sub-retinally injected with 1 µl ssAAV2 at $2\times10^9$ DRP/µl. The first group (control) received sub-retinal ssAAV2-EPO (TM003), and the second (experimental) ssAAV2-eGFP (DR005). The effect of mouse Epo on the retinal vascular changes was examined in retinal flat-mounts at 21 days post injection.

The AAV (adeno-associated virus) tested were: ssAAV2-EPO-eGFP [(AAV2-CMV-mEPO-IRES-eGFP) from Gene Therapy Center Virus Vector Core Facility, The University of North Carolina at Chapel Hill, Lot#AV3782] and ssAAV2-GFP [(AAV2-eGFP) from Gene Therapy Center Virus Vector Core Facility, The University of North Carolina at Chapel Hill: Lot#AV3725].

Procedure:

AAV vectors were delivered via sub-retinal injection on both eyes of the mice tested. All procedures described were performed under aseptic conditions, using sterile reagents, syringes and appropriate PPE.

1. The mice were immobilized, and their pupils dilated with a drop of cyclopentolate (1%), followed by a drop of 2.5% phenylephrine.
2. Next, the animal was anesthetized with Avertin (250 mg/kg) i.p. The cornea was topically anesthetized with a drop of 0.5% proparacaine.
3. After placing the animal under a surgical microscope, a micro-scalpel was used to make a 0.5 mm nasal incision, posterior to the limbus.
4. A blunt needle attached to a 10 µl Hamilton syringe was tangentially inserted through the scleral incision toward the temporal retina. The needle was advanced until resistance was felt.
5. 1 µl of ssAAV2 vector (either ssAAV2-EPO-eGFP or ssAAV2-GFP, both containing fluorescein diluted 1:50 to visualize delivery) was slowly injected into the sub-retinal space.
6. The eye was examined under the surgical microscope. A successful sub-retinal injection was confirmed by visualizing a fluorescein containing retinal detachment.
7. The injection was scored depending on the degree of retinal damage (visualized by hemorrhage size) and damage to the lens.
8. The animal was turned to the other side and the procedure was repeated.
9. Antibiotic ointment was applied to both eyes after injection.

Retinal Dissection, Imaging and Quantification on Retinal Flatmount:

1. 0.1 ml Concavelin-A (Con-A) was injected (i.v., tail vein) 1 to 5 minutes before euthanasia ($CO_2$)
2. The eyes were enucleated and fixed in paraformaldehyde (4% in PBS) for two hours. They were subsequently maintained at 4° C. in PBS buffer for 1-3 days until dissection
3. The cornea and lens were removed, and the retina was dissected from the posterior eye cup (retinal pigmented epithelium/choroid)
4. Four radial incisions were made to the retina and flat-mounted in Vectashield mounting media with the photoreceptor layer face down.
5. Once mounted, the flat-mounts were centered on the central retina (using the optic nerve head as a reference) and the Con-A labeled retinal vessels were captured at 20× using the Zeiss Imaging System (AxioVision)
6. The AxioVision software was used to measure the diameter of central retinal vessels that are 200 µm away from optical nerve head.
7. Data obtained was analyzed with GraphPad Prism.

Results and Conclusion:

Quantification of vessel diameter revealed that ssAAV2-EPO induced significant (*$p<0.001$) vessel dilation in the central retina compared to ssAAV2-GFP and naïve eyes (6 eyes) (FIG. 1). No significant difference was found comparing ssAAV2-GFP vs. naïve group. Samples were analyzed using a one-way ANOVA with Dunnet's post-test (C) Representative flat-mounts for each group. Long-term delivery of Epo by AAV2-Epo-eGFP resulted in a statistically significant increase in venous caliber (FIG. 1), a key hallmark of diabetic macular edema in humans. Accordingly, in one aspect, the invention relates to a method of decreasing venous caliber in the eye by administering an anti-EPO antibody described herein to a subject in a therapeutically effective amount.

Example 5b: In Vivo Efficacy of Anti-Epo Antibodies

The in vivo activity, and therapeutic efficacy, of the anti-Epo antibodies described herein can be assessed in the mouse model of ocular edema described above.

In Vivo Challenge in the Mouse Model

C57B6 mice aged 8 weeks old are injected subretinally with one of the following. Groups:

Group 1: AAV2-eGFP @ titer $2\times10^9$ DRP @ titer, 1 ul/eye, n=20 eyes of 10 mice Group 2: AAV2-Epo-eGFP @ titer $2\times10^9$ DRP, 1 ul/eye, n=20 eyes of 10 mice Group 3: AAV2-Epo-eGFP @ titer $2\times10^9$, 1 ul/eye, +anti-Epo Fab, 100 ug/eye, 1 weekly, n=20 eyes of 10 mice The effect of anti-Epo antibodies dosed appropriately are examined in the mouse model by measuring vessel diameter 2 weeks post injection.

AAV-GFP (AAV2-eGFP) and AAV2-Epo-eGFP (AAV2-CMV-mEpo-IRES-eGFP) from Gene Therapy Center Virus Vector Core Facility, The University of North Carolina at Chapel Hill.

Intraocular injection of the anti-Epo antibodies will inhibit retinal vessel dilation anti-Epo antibodies to ameliorate the effects of Epo on decrease blood flow and hypoxic conditions in the retina. Thus, the anti-Epo antibodies are expected to reduce the retinal pathology that is also seen in patients with vascular retinal diseases such as wet AMD and diabetic retinopathy.

Example 6: In Vivo Neutralization of Free EPO

Example 6a: In Vivo Neutralization of Free EPO Using an Anti-Epo Fab

The in vivo activity and therapeutic efficacy of anti-EPO antibodies were assessed in rabbit eyes as follows. Rabbits were dosed intravitreally with an anti-EPO Fab, NVS2 (1 mg/eye) and challenged with an intravitreal dose of EPO (3 ug/eye) four days later. Animals were sacrificed and ocular tissues including vitreous was extracted. The amount of free EPO and total EPO in the vitreous was determined as described below.

| Group | [Anti-EPO Fab] mg/eye | EPO ug/eye |
|---|---|---|
| 1 | 1 | — |
| 2 | 1 | 3 |

Total/Free EPO Levels:

Assays were performed using standard binding MSD plates (Meso-Scale Discovery, 384-well: MSD cat#L21XA), using coating buffer (PBS) and incubation buffer (PBS with 2% BSA (Sigma cat#A4503) and 0.1% Tween20 and 0.1% Triton-X).

Capture antibodies were coated at 1 µg/ml in PBS (25 µl), and incubated overnight at 4° C. Plates were washed 3× in wash buffer (PBS with 0.05% Tween20), and blocked with 25 µl incubation buffer at RT for 2 hrs. Plates were washed 3× in wash buffer. Vitreous dilutions in incubation buffer were added to the plate (25 µl), and incubated for 60 min at RT. Human recombinant Darbepoietin was used as a standard (A000123, starting at 2 µg/ml). Plates were washed 3× in wash buffer. 25 µl primary antibody was added (1 µg/ml in incubation buffer), and incubated at RT for 60 min. Plates were washed 3× in wash buffer. 25 µl of anti-species secondary Sulfo-TAG antibodies were added (1:1000 in incubation buffer), and incubated at RT for 60 min. Plates were washed 3× in wash buffer, and 25 µl of 1×MSD Read buffer T was added (with surfactant, MSD cat#R92TC-1). Plates were read on a MSD Spector Imager 6000.

| | | |
|---|---|---|
| Total EPO | Coat Antibody | Epo-26 Clone 26G9C10 |
| | Primary Antibody | Anti-EPO Fab |
| | Secondary Antibody | anti-human R32AJ-1 |
| | Vitreous Dilution | 1:20-1:25 |
| | Sensitivity | 0.03 ng/ml |
| Free EPO | Coat Antibody | Anti-EPO Fab |
| | Primary Antibody | Epo-26 Clone 26G9C10 |
| | Secondary Antibody | anti-mouse R32AC-1 |
| | Vitreous Dilution | 1:75-1:500 |
| | Sensitivity | 1.6 ng/ml |

Figure 2:
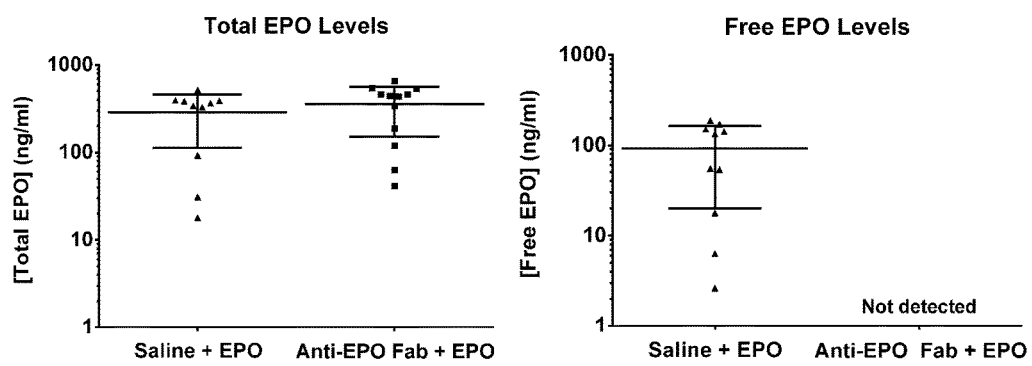
FIG. 2. Shows that an anti-EPO Fab neutralizes EPO in rabbit eyes.

Results and Conclusion:

The total EPO levels measured in the vitreous of animals injected with anti-EPO or vehicle was similar as expected (FIG. 2). In contrast, no free EPO was measured in the vitreous of rabbits injected with anti-EPO Fab, but average ~100 ng/ml free EPO was measured in the vitreous of rabbits injected with vehicle. Anti-EPO Fab administered intravitreally completely neutralized free EPO levels as expected.

Example 6b: In Vivo Neutralization of Free EPO Using a Anti-Epo Fab

The in vivo activity and therapeutic efficacy of anti-EPO antibodies were assessed in rabbit eyes as follows. Rabbits were dosed intravitreally with a pre-mixed solution of an anti-EPO Fab, NVS2 (1 mg/eye) and EPO (3 ug/eye). Animals were sacrificed and ocular tissues including vitreous was extracted. The amount of free EPO and total EPO in the vitreous was determined as described below. Note: Some eyes received a pre-mix solution of an anti-EPO Fab, EPO, and VEGF.

| Group | [Anti-EPO Fab] mg/eye | EPO ug/eye | VEGF ng/eye |
|---|---|---|---|
| 1 | — | — | 200 |
| 2 | — | 3 | 200 |
| 3 | 1 | 3 | 200 |
| 4 | 1 | 3 | — |

Total/Free EPO Levels:

Assays were performed using standard binding MSD plates (Meso-Scale Discovery, 384-well: MSD cat#L21XA), using coating buffer (PBS) and incubation buffer (PBS with 2% BSA (Sigma cat#A4503) and 0.1% Tween20 and 0.1% Triton-X).

Capture antibodies were coated at 1 µg/ml in PBS (25 µl), and incubated overnight at 4° C. Plates were washed 3× in wash buffer (PBS with 0.05% Tween20), and blocked with 25 µl incubation buffer at RT for 2 hrs. Plates were washed 3× in wash buffer. Vitreous dilutions in incubation buffer were added to the plate (25 µl), and incubated for 60 min at RT. Human recombinant Darbepoietin was used as a standard (A000123, starting at 2 µg/ml). Plates were washed 3× in wash buffer. 25 µl primary antibody was added (1 µg/ml in incubation buffer), and incubated at RT for 60 min. Plates were washed 3× in wash buffer. 25 µl of anti-species secondary Sulfo-TAG antibodies were added (1:1000 in incubation buffer), and incubated at RT for 60 min. Plates were washed 3× in wash buffer, and 25 µl of 1×MSD Read buffer T was added (with surfactant, MSD cat#R92TC-1). Plates were read on a MSD Spector Imager 6000.

| | | |
|---|---|---|
| Total EPO | Coat Antibody | Epo-26 Clone 26G9C10 |
| | Primary Antibody | Anti-EPO Fab |
| | Secondary Antibody | anti-human R32AJ-1 |
| | Vitreous Dilution | 1:20-1:25 |
| | Sensitivity | 0.03 ng/ml |
| Free EPO | Coat Antibody | Anti-EPO Fab |
| | Primary Antibody | Epo-26 Clone 26G9C10 |
| | Secondary Antibody | anti-mouse R32AC-1 |
| | Vitreous Dilution | 1:75-1:500 |
| | Sensitivity | 1.6 ng/ml |

RESULTS AND CONCLUSION

Figure 3:
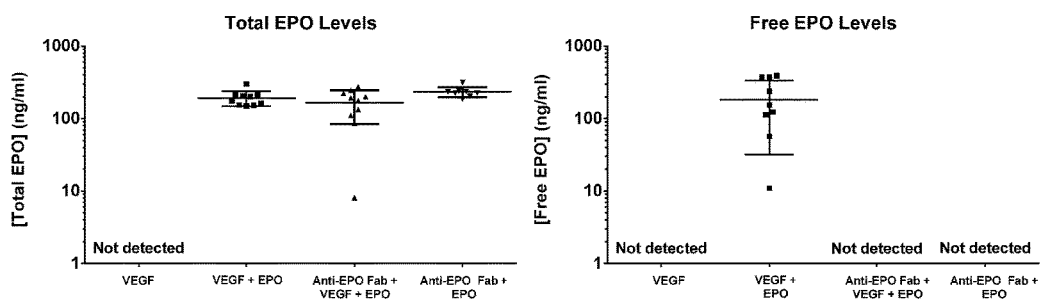
FIG. 3. Shows that an anti-EPO Fab neutralizes EPO in rabbit eyes.

The total EPO levels measured in the vitreous of animals injected with anti-EPO or vehicle were similar as expected (FIG. 3). In contrast, no free EPO was measured in the vitreous of rabbits injected with an anti-EPO Fab, while on an average ~200 ng/ml free EPO was measured in the vitreous of rabbits injected with vehicle (FIG. 3). Presence of VEGF did not appear to have any effect on either free or total EPO levels measured. Anti-EPO Fab administered intravitreally completely neutralized free EPO levels as expected.

The invention claimed is:

1. A method of treating macular edema in a subject comprising administering to said subject, an effective amount of a composition comprising an antibody, or antigen binding fragment thereof, that binds EPO and comprises
   a) heavy chain variable region HCDR1, HCDR2, and HCDR3 as set forth in SEQ ID NOs: 1, 2, and 3, respectively, and light chain variable region LCDR1, LCDR2, and LCDR3 as set forth in SEQ ID NOs: 4, 5, and 6, respectively;
   b) heavy chain variable region HCDR1, HCDR2, and HCDR3 as set forth in SEQ ID NOs: 21, 22, and 23, respectively, and light chain variable region LCDR1, LCDR2, and LCDR3 as set forth in SEQ ID NOs: 24, 25, and 26, respectively;
   c) heavy chain variable region HCDR1, HCDR2, and HCDR3 as set forth in SEQ ID NOs: 41, 42, and 43, respectively, and light chain variable region LCDR1, LCDR2, and LCDR3 as set forth in SEQ ID NOs: 44, 45, and 46, respectively; or
   d) heavy chain variable region HCDR1, HCDR2, and HCDR3 as set forth in SEQ ID NOs: 61, 62, and 63, respectively, and light chain variable region LCDR1, LCDR2, and LCDR3 as set forth in SEQ ID NOs: 64, 65, and 66, respectively.

2. The method of claim 1, wherein said antibody, or antigen binding fragment thereof, comprises heavy and light chain variable regions having amino acid sequences at least 90% identical to SEQ ID NOs: 13 and 14; SEQ ID NOs: 33 and 34; SEQ ID NOs: 53 and 54; or SEQ ID NOs: 73 and 74, respectively.

3. The method of claim 1, wherein said antibody, or antigen binding fragment thereof, comprises a heavy chain and a light chain with amino acid sequences having at least 90% sequence identity to SEQ ID NOs: 15 and 16; SEQ ID NOs: 35 and 36; SEQ ID NOs: 55 and 56; or SEQ ID NOs: 75 and 76, respectively.

4. The method of claim 1, wherein said antibody, or antigen binding fragment thereof, is a human antibody, a chimeric antibody, a monoclonal antibody, a single chain antibody, Fab, Fab', F(ab')2, Fv or scFv.

5. The method of claim 1, wherein said antibody, or antigen binding fragment thereof, is an IgG isotype.

6. The method of claim 1, wherein administration of said composition decreases retinal vein dilation, decreases vascular leakage, and/or increases blood flow in the eye.

7. The method of claim 1, wherein said method further comprises administering an anti-VEGF antibody or an anti-VEGF receptor antibody.

8. The method of claim 1, wherein said method further comprises administering a second composition, wherein said second composition comprises a compound selected from the group consisting of ranibizumab, bevacizumab, pegaptanib, aflibercept, pazopanib, sorafenib, sunitinib, and rapamycin.

9. The method of claim 8, wherein said second composition comprises ranibizumab.

10. The method of claim 1, wherein the antibody, or antigen binding fragment thereof, comprises heavy chain variable region HCDR1, HCDR2, and HCDR3 as set forth in SEQ ID NOs: 21, 22, and 23, respectively, and light chain variable region LCDR1, LCDR2, and LCDR3 as set forth in SEQ ID NOs: 24, 25, and 26, respectively.

11. The method of claim 1, wherein the antibody, or antigen binding fragment thereof, comprises heavy and light chain variable regions having amino acid sequences at least 90% identical to SEQ ID NOs: 33 and 34, respectively.

12. The method of claim 1, wherein the antibody, or antigen binding fragment thereof, comprises heavy and light chain variable regions having amino acid sequences as set forth in SEQ ID NOs: 33 and 34, respectively.

13. The method of claim 1, wherein the antibody, or antigen binding fragment thereof, comprises a heavy chain and a light chain having amino acid sequences with at least 90% sequence identity to SEQ ID NOs: 35 and 36, respectively.

14. The method of claim 1, wherein the antibody, or antigen binding fragment thereof, comprises a heavy chain and a light chain having amino acid sequences as set forth in SEQ ID NOs: 35 and 36, respectively.

* * * * *

SEQUENCE LISTING

```
<160> NUMBER OF SEQ ID NOS: 97

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Ala Ile Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ile Asp Pro Ile Ser Gly Phe Ala Asp Tyr Ala Gln Lys Phe Gln
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Leu Tyr Tyr Pro Gly Thr Trp Met Ala Val Met Ala Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Gly Asp Asn Ile Pro Glu Tyr Tyr Val His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

```
Arg Asp Asn Glu Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Val Phe Asp Glu Ser Ser Trp His Trp Val
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Thr Phe Arg Ser Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Pro Ile Ser Gly Phe
1               5

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Leu Tyr Tyr Pro Gly Thr Trp Met Ala Val Met Ala Tyr
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Asn Ile Pro Glu Tyr Tyr
1               5

<210> SEQ ID NO 11
<211> LENGTH: 3
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 11

Arg Asp Asn
1

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Asp Glu Ser Ser Trp His Trp
1               5

<210> SEQ ID NO 13
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Tyr
            20                  25                  30

Ala Ile Ser Trp Val Arg Gln Ala Pro Gly Gln Gly Leu Glu Trp Met
        35                  40                  45

Gly Gly Ile Asp Pro Ile Ser Gly Phe Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Leu Tyr Tyr Pro Gly Thr Trp Met Ala Val Met Ala Tyr
            100                 105                 110

Trp Gly Arg Gly Thr Leu Val Thr Val Ser Ser
        115                 120

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Tyr Val Leu Thr Gln Pro Pro Ser Val Ser Val Ala Pro Gly Lys
1               5                   10                  15

Thr Ala Arg Ile Thr Cys Ser Gly Asp Asn Ile Pro Gly Tyr Tyr Val
            20                  25                  30

His Trp Tyr Gln Gln Lys Pro Gly Gln Ala Pro Val Leu Val Ile Tyr
        35                  40                  45

Arg Asp Asn Glu Arg Pro Ser Gly Ile Pro Glu Arg Phe Ser Gly Ser
    50                  55                  60
```

```
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Phe Asp Glu Ser Ser Trp His
                 85                  90                  95

Trp Val Phe Gly Gly Gly Thr Lys Leu Thr Val Leu
            100                 105
```

<210> SEQ ID NO 15
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Val Gln Leu Val Gln Ser Gly Ala Glu Val Lys Lys Pro Gly Ser
 1               5                  10                  15

Ser Val Lys Val Ser Cys Lys Ala Ser Gly Thr Phe Arg Ser Tyr
                 20                  25                  30

Ala Ile Ser Trp Val Arg Gln Ala Pro Gly Gln Gly Leu Glu Trp Met
             35                  40                  45

Gly Gly Ile Asp Pro Ile Ser Gly Phe Ala Asp Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Leu Tyr Tyr Pro Gly Thr Trp Met Ala Val Met Ala Tyr
             100                 105                 110

Trp Gly Arg Gly Thr Leu Val Thr Val Ser Ser Ala Ser Thr Lys Gly
         115                 120                 125

Pro Ser Val Phe Pro Leu Ala Pro Ser Ser Lys Ser Thr Ser Gly Gly
         130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys
225
```

<210> SEQ ID NO 16
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Ser Tyr Val Leu Thr Gln Pro Pro Ser Val Ser Val Ala Pro Gly Lys
 1               5                  10                  15
```

Thr Ala Arg Ile Thr Cys Ser Gly Asp Asn Ile Pro Glu Tyr Tyr Val
            20                  25                  30

His Trp Tyr Gln Gln Lys Pro Gly Gln Ala Pro Val Leu Val Ile Tyr
        35                  40                  45

Arg Asp Asn Glu Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Phe Asp Ser Ser Trp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 17
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
caggtgcagc tggtgcagtc aggcgccgaa gtgaagaaac ccggctctag cgtgaaggtg      60
tcctgtaaag ctagtggcgg caccttaga tcctacgcta ttagctgggt gcgacaggct     120
ccaggccagg gcctcgaatg gatgggcggc atcgacccta ttagcggctt cgccgactac     180
gctcagaaat tcagggcag agtgactatc accgccgacg agtctactag caccgcctac     240
atggaactgt ctagcctgag atcagaggac accgccgtgt actactgcgc tagagagctg     300
tactaccccg gcacctggat ggccgtgatg gcctattggg gcagaggcac cctggtgaca     360
gtgtcttct                                                             369

<210> SEQ ID NO 18
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
agctacgtgc tgacccagcc ccctagcgtg tcagtggccc ctggcaagac cgctagaatc      60
acctgtagcg gcgataacat ccccgagtac tacgtgcact ggtatcagca gaagcccggc     120

```
caggcccccg tgctggtgat ctatagagat aacgagcggc ctagcggcat ccccgagcgg    180
ttttccggct ctaatagcgg caacaccgct accctgacta tttcaagagt ggaagccggc    240
gacgaggccg actactactg tcaggtgttc gacgagtctt catggcactg ggtgttcggc    300
ggaggcacca agctgaccgt gctg                                           324
```

<210> SEQ ID NO 19
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
caggtgcagc tggtgcagtc aggcgccgaa gtgaagaaac ccggctctag cgtgaaggtg     60
tcctgtaaag ctagtggcgg cacctttaga tcctacgcta ttagctgggt gcgacaggct    120
ccaggccagg gcctcgaatg gatgggcggc atcgacccta ttagcggctt cgccgactac    180
gctcagaaat tcagggcag agtgactatc accgccgacg agtctactag caccgcctac    240
atggaactgt ctagcctgag atcagaggac accgccgtgt actactgcgc tagagagctg    300 tactacccccg gcacctggat ggccgtgatg gcctattggg gcagaggcac cctggtgaca    360
gtgtcttctg ctagcactaa gggcccctcc gtgttccctc tggccccttc agcaagtct    420 acctctggcg gcaccgctgc tctgggctgc ctggtgaagg actacttccc tgagcctgtg    480
acagtgtcct ggaactctgg cgccctgacc tccggcgtgc acaccttccc tgccgtgctg    540
cagtcctccg gcctgtactc cctgtcctcc gtggtgacag tgccttcctc cagcctgggc    600
acccagacct atatctgcaa cgtgaaccac aagccttcca acaccaaggt ggacaagcgg    660
gtggagccta agtcatgc                                                  678
```

<210> SEQ ID NO 20
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
agctacgtgc tgacccagcc ccctagcgtg tcagtggccc ctggcaagac cgctagaatc     60
acctgtagcg gcgataacat ccccgagtac tacgtgcact ggtatcagca gaagcccggc    120
caggcccccg tgctggtgat ctatagagat aacgagcggc ctagcggcat ccccgagcgg    180
ttttccggct ctaatagcgg caacaccgct accctgacta tttcaagagt ggaagccggc    240
gacgaggccg actactactg tcaggtgttc gacgagtctt catggcactg ggtgttcggc    300
ggaggcacca agctgaccgt gctgggccag cctaaggctg cccccagcgt gaccctgttc    360
ccccccagca gcgaggagct gcaggccaac aaggccaccc tggtgtgcct gatcagcgac    420
ttctacccag cgccgtgac cgtggcctgg aaggccgaca gcagccccgt gaaggccggc    480
gtggagacca ccacccccag caagcagagc aacaacaagt acgccgccag cagctacctg    540
agcctgaccc ccgagcagtg gaagagccac aggtcctaca gctgccaggt gacccacgag    600
ggcagcaccg tggaaaagac cgtggcccca accgagtgca gc                      642
```

<210> SEQ ID NO 21

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Tyr Trp Ile Gly
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Ile Asp Pro Tyr Arg Ser Glu Ile Arg Tyr Ser Pro Ser Phe Gln
1               5                   10                  15

Gly

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Ser Ser Glu Pro Phe Asp Ser
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Gly Asp Lys Leu Gly Asp His Tyr Ala Tyr
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Asp Ser Lys Arg Pro Ser
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 26

Ala Thr Trp Thr Phe Glu Gly Asp Tyr Val
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Tyr Ser Phe Thr Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Pro Tyr Arg Ser Glu
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Ser Ser Glu Pro Phe Asp Ser
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Lys Leu Gly Asp His Tyr
1               5

<210> SEQ ID NO 31
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Asp Ser
1

<210> SEQ ID NO 32
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 32

Trp Thr Phe Glu Gly Asp Tyr
1               5

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Trp Ile Asp Pro Tyr Arg Ser Glu Ile Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Ser Glu Pro Phe Asp Ser Trp Gly Gln Gly Thr Leu
            100                 105                 110

Val Thr Val Ser Ser
        115

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ser Tyr Val Leu Thr Gln Pro Pro Ser Val Ser Val Ala Pro Gly Lys
1               5                   10                  15

Thr Ala Arg Ile Thr Cys Ser Gly Asp Lys Leu Gly Asp His Tyr Ala
            20                  25                  30

Tyr Trp Tyr Gln Gln Lys Pro Gly Gln Ala Pro Val Leu Val Ile Tyr
        35                  40                  45

Asp Asp Ser Lys Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Ala Thr Trp Thr Phe Glu Gly Asp Tyr
                85                  90                  95

Val Phe Gly Gly Gly Thr Lys Leu Thr Val Leu
            100                 105

<210> SEQ ID NO 35

<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Trp Ile Asp Pro Tyr Arg Ser Glu Ile Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Ser Glu Pro Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys
    210                 215                 220

<210> SEQ ID NO 36
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Tyr Val Leu Thr Gln Pro Pro Ser Val Ser Val Ala Pro Gly Lys
1               5                   10                  15

Thr Ala Arg Ile Thr Cys Ser Gly Asp Lys Leu Gly Asp His Tyr Ala
            20                  25                  30

Tyr Trp Tyr Gln Gln Lys Pro Gly Gln Ala Pro Val Leu Val Ile Tyr
        35                  40                  45

Asp Asp Ser Lys Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Ala Thr Trp Thr Phe Glu Gly Asp Tyr
                85                  90                  95

```
Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
            195                 200                 205

Pro Thr Glu Cys Ser
    210

<210> SEQ ID NO 37
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gaggtgcagc tggtgcagtc aggcgccgaa gtgaagaagc ccggcgagtc actgaagatt      60
agctgtaaag gctcaggcta tagcttcact agctactgga tcggctgggt gcgacagatg     120
cccggcaagg gcctggaatg gatgggctgg atcgacccct atagatcaga gattaggtat     180
agccctagct ttcagggcca ggtgacaatt agcgccgata agtctattag caccgcctac     240
ctgcagtggt ctagcctgaa ggctagtgac accgctatgt actactgcgc tagagtgtct     300
agcgagccct cgatagctg gggccagggc accctggtga cagtgtcttc a                351

<210> SEQ ID NO 38
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
agctacgtgc tgacccagcc ccctagcgtg tcagtggccc ctggcaagac cgctagaatc      60
acctgtagcg gcgataagct gggcgatcac tacgcctact ggtatcagca gaagcccggc     120
caggcccccg tgctggtgat ctacgacgac tctaagcggc ctagcggcat ccccgagcgg     180
tttagcggct ctaatagcgg caacaccgct accctgacta tttcaagagt ggaagccggc     240
gacgaggccg actactactg cgctacctgg accttcgagg gcgactacgt gttcggcgga     300
ggcactaagc tgaccgtgct g                                                321

<210> SEQ ID NO 39
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 39

```
gaggtgcagc tggtgcagtc aggcgccgaa gtgaagaagc ccggcgagtc actgaagatt      60
agctgtaaag gctcaggcta tagcttcact agctactgga tcggctgggt gcgacagatg     120
cccggcaagg gcctggaatg gatgggctgg atcgacccct atagatcaga gattaggtat     180
agccctagct ttcagggcca ggtgacaatt agcgccgata agtctattag caccgcctac     240
ctgcagtggt ctagcctgaa ggctagtgac accgctatgt actactgcgc tagagtgtct     300
agcgagccct cgatagctg gggccagggc accctggtga cagtgtcttc agctagcact     360
aagggcccct ccgtgttccc tctggcccct ccagcaagt ctacctctgg cggcaccgct     420
gctctgggct gcctggtgaa ggactacttc cctgagcctg tgacagtgtc ctggaactct     480
ggcgccctga cctccggcgt gcacaccttc cctgccgtgc tgcagtcctc cggcctgtac     540
tccctgtcct ccgtggtgac agtgccttcc tccagcctgg cacccagac ctatatctgc      600
aacgtgaacc acaagccttc caacaccaag gtggacaagc gggtggagcc taagtcatgc     660
```

<210> SEQ ID NO 40
<211> LENGTH: 639
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
agctacgtgc tgacccagcc ccctagcgtg tcagtggccc ctggcaagac cgctagaatc      60
acctgtagcg gcgataagct gggcgatcac tacgcctact ggtatcagca gaagcccggc     120
caggcccccg tgctggtgat ctacgacgac tctaagcggc ctagcggcat ccccgagcgg     180
tttagcggct ctaatagcgg caacaccgct accctgacta tttcaagagt ggaagccggc     240
gacgaggccg actactactg cgctacctgg accttcgagg gcgactacgt gttcggcgga     300
ggcactaagc tgaccgtgct gggccagcct aaggctgccc ccagcgtgac cctgttcccc     360
cccagcagcg aggagctgca ggccaacaag gccaccctgg tgtgcctgat cagcgacttc     420
tacccaggcg ccgtgaccgt ggcctggaag gccgacagca gccccgtgaa ggccggcgtg     480
gagaccacca cccccagcaa gcagagcaac aacaagtacg ccgccagcag ctacctgagc     540
ctgacccccg agcagtggaa gagccacagg tcctacagct gccaggtgac ccacgagggc     600
agcaccgtgg aaaagaccgt ggccccaacc gagtgcagc                            639
```

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Ser Asn Thr Ala Ala Trp Asn
1               5

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic

```
                          peptide

<400> SEQUENCE: 42

Val Ile Tyr Tyr Arg Ser Lys Trp Tyr Asn Asp Tyr Ala Val Ser Val
1               5                   10                  15

Lys Ser

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Val Pro Gly Gly Asp Pro Gly Leu Glu His Ala Phe Ala Tyr
1               5                   10                  15

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Gly Asp Asn Leu Gly Thr Tyr Tyr Val Glu
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Asp Ser Asp Arg Pro Ser
1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ser Phe Ala Ser Trp Ser Asp Ser Val
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Asp Ser Val Ser Ser Asn Thr Ala
1               5
```

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Tyr Arg Ser Lys Trp Tyr
1               5

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Val Pro Gly Gly Asp Pro Gly Leu Glu His Ala Phe Ala Tyr
1               5                   10                  15

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Asn Leu Gly Thr Tyr Tyr
1               5

<210> SEQ ID NO 51
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Asp Ser
1

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Ala Ser Trp Ser Asp Ser
1               5

<210> SEQ ID NO 53
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Gln Val Gln Leu Gln Gln Ser Gly Pro Gly Leu Val Lys Pro Ser Gln
1               5                   10                  15
Thr Leu Ser Leu Thr Cys Ala Ile Ser Gly Asp Ser Val Ser Ser Asn
            20                  25                  30
Thr Ala Ala Trp Asn Trp Ile Arg Gln Ser Pro Ser Arg Gly Leu Glu
        35                  40                  45
Trp Leu Gly Val Ile Tyr Tyr Arg Ser Lys Trp Tyr Asn Asp Tyr Ala
    50                  55                  60
Val Ser Val Lys Ser Arg Ile Thr Ile Asn Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Arg Ser Val Pro Gly Gly Asp Pro Gly Leu Glu His
            100                 105                 110
Ala Phe Ala Tyr Trp Gly Arg Gly Thr Leu Val Thr Val Ser Ser
        115                 120                 125
```

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Ser Tyr Val Leu Thr Gln Pro Pro Ser Val Ser Val Ala Pro Gly Lys
1               5                   10                  15
Thr Ala Arg Ile Thr Cys Ser Gly Asp Asn Leu Gly Thr Tyr Tyr Val
            20                  25                  30
Glu Trp Tyr Gln Gln Lys Pro Gly Gln Ala Pro Val Leu Val Ile Tyr
        35                  40                  45
Asp Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Ala Ser Phe Ala Ser Trp Ser Asp Ser
                85                  90                  95
Val Phe Gly Gly Gly Thr Lys Leu Thr Val Leu
            100                 105
```

<210> SEQ ID NO 55
<211> LENGTH: 230
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Gln Val Gln Leu Gln Gln Ser Gly Pro Gly Leu Val Lys Pro Ser Gln
1               5                   10                  15
Thr Leu Ser Leu Thr Cys Ala Ile Ser Gly Asp Ser Val Ser Ser Asn
            20                  25                  30
Thr Ala Ala Trp Asn Trp Ile Arg Gln Ser Pro Ser Arg Gly Leu Glu
        35                  40                  45
Trp Leu Gly Val Ile Tyr Tyr Arg Ser Lys Trp Tyr Asn Asp Tyr Ala
```

```
                    50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                     85                  90                  95

Tyr Tyr Cys Ala Arg Ser Val Pro Gly Asp Pro Gly Leu Glu His
                100                 105                 110

Ala Phe Ala Tyr Trp Gly Arg Gly Thr Leu Val Thr Val Ser Ser Ala
                115                 120                 125

Ser Thr Lys Gly Pro Ser Val Phe Pro Leu Ala Pro Ser Ser Lys Ser
                130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Leu Gly Thr Gln Thr Tyr
                195                 200                 205

Ile Cys Asn Val Asn His Lys Pro Ser Asn Thr Lys Val Asp Lys Arg
 210                 215                 220

Val Glu Pro Lys Ser Cys
225                 230

<210> SEQ ID NO 56
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ser Tyr Val Leu Thr Gln Pro Pro Ser Val Ser Val Ala Pro Gly Lys
  1               5                  10                  15

Thr Ala Arg Ile Thr Cys Ser Gly Asp Asn Leu Gly Thr Tyr Tyr Val
                 20                  25                  30

Glu Trp Tyr Gln Gln Lys Pro Gly Gln Ala Pro Val Leu Val Ile Tyr
             35                  40                  45

Asp Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Ala Ser Phe Ala Ser Trp Ser Asp Ser
                 85                  90                  95

Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
            115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175
```

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 57
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggtgcagc tgcagcagtc aggccctggc ctggtgaaac ctagtcagac cctgagcctg      60
acctgcgcta ttagcggcga tagcgtgtca tctaacaccg ccgcctggaa ctggattaga     120
cagtcaccta gtagaggcct ggaatggctg ggcgtgatct actataggtc taagtggtac     180
aacgactacg ccgtgtcagt gaagtctagg atcactatta accccgacac ctctaagaat     240
cagttcagcc tgcagctgaa tagcgtgacc cccgaggaca ccgccgtgta ctactgcgct     300
agatcagtgc tggcggcga ccccggcctg aacacgcct ttgcctactg gggcagaggc      360
accctggtga cagtgtcttc t                                              381

<210> SEQ ID NO 58
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
agctacgtgc tgacccagcc ccctagcgtg tcagtggccc ctggcaagac cgctagaatc      60
acctgtagcg gcgataacct gggcacctac tacgtggaat ggtatcagca gaagcccggc     120
caggcccccg tgctggtgat ctacgacgat agcgatagac tagcggcat ccccgagcgg      180 tttagcggct ctaatagcgg caacaccgct accctgacta ttagtagagt ggaagccggc     240
gacgaggccg actactactg cgctagtttc gctagttgga gcgattcagt gttcggcgga     300
ggcactaagc tgaccgtgct g                                              321

<210> SEQ ID NO 59
<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
caggtgcagc tgcagcagtc aggccctggc ctggtgaaac ctagtcagac cctgagcctg      60
acctgcgcta ttagcggcga tagcgtgtca tctaacaccg ccgcctggaa ctggattaga     120
cagtcaccta gtagaggcct ggaatggctg ggcgtgatct actataggtc taagtggtac     180
aacgactacg ccgtgtcagt gaagtctagg atcactatta accccgacac ctctaagaat     240
cagttcagcc tgcagctgaa tagcgtgacc cccgaggaca ccgccgtgta ctactgcgct     300
agatcagtgc tggcggcga ccccggcctg aacacgcct ttgcctactg gggcagaggc      360

```
acccggtga cagtgtcttc tgctagcact aagggcccct ccgtgttccc tctggcccct    420
tccagcaagt ctacctctgg cggcaccgct gctctgggct gcctggtgaa ggactacttc    480
cctgagcctg tgacagtgtc ctggaactct ggcgccctga cctccggcgt gcacaccttc    540
cctgccgtgc tgcagtcctc cggcctgtac tccctgtcct ccgtggtgac agtgccttcc    600
tccagcctgg gcacccagac ctatatctgc aacgtgaacc acaagccttc caacaccaag    660
gtggacaagc gggtggagcc taagtcatgc                                    690
```

<210> SEQ ID NO 60
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
agctacgtgc tgacccagcc ccctagcgtg tcagtggccc ctggcaagac cgctagaatc     60
acctgtagcg gcgataacct gggcacctac tacgtggaat ggtatcagca gaagcccggc    120 caggccccg tgctggtgat ctacgacgat agcgatagac ctagcggcat ccccgagcgg    180
tttagcggct ctaatagcgg caacaccgct accctgacta ttagtagagt ggaagccggc    240
gacgaggcca actactactg cgctagtttc gctagttgga gcgattcagt gttcggcgga    300
ggcactaagc tgaccgtgct gggccagcct aaggctgccc ccagcgtgac cctgttcccc    360
cccagcagca ggagctgca ggccaacaag gccaccctgg tgtgcctgat cagcgacttc    420
tacccaggcg ccgtgaccgt ggcctggaag gccgacagca gccccgtgaa ggccggcgtg    480
gagaccacca cccccagcaa gcagagcaac aacaagtacg ccgccagcag ctacctgagc    540
ctgacccccg agcagtggaa gagccacagg tcctacagct gccaggtgac ccacgagggc    600
agcaccgtgg aaaagaccgt ggccccaacc gagtgcagc                          639
```

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Tyr Tyr Met Ser
1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Ile Asn Pro Leu Lys Gly Asn Thr Asn Tyr Ala Gln Lys Phe Gln
1               5                   10                  15

Gly

<210> SEQ ID NO 63
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Gly Met Tyr Phe Asp Ile
1               5

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Gly Asp Ser Ile Gly Asp Lys Tyr Val Tyr
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asp Thr Asn Lys Arg Pro Ser
1               5

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ser Trp Asp Leu Asp Phe Asn Thr Tyr Val
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Tyr Thr Phe Thr Ser Tyr
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asn Pro Leu Lys Gly Asn
```

```
<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Gly Met Tyr Phe Asp Ile
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Ser Ile Gly Asp Lys Tyr
1               5

<210> SEQ ID NO 71
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Thr Asn
1

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Asp Leu Asp Phe Asn Thr Tyr
1               5

<210> SEQ ID NO 73
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Ser Trp Val Arg Gln Ala Pro Gly Gln Gly Leu Glu Trp Met
            35                  40                  45

Gly Trp Ile Asn Pro Leu Lys Gly Asn Thr Asn Tyr Ala Gln Lys Phe
```

```
                    50                  55                  60
Gln Gly Arg Val Thr Met Thr Arg Asp Thr Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Glu Gly Met Tyr Phe Asp Ile Trp Gly Gln Gly Thr Leu Val
                100                 105                 110

Thr Val Ser Ser
            115

<210> SEQ ID NO 74
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ser Tyr Glu Leu Thr Gln Pro Leu Ser Val Ser Val Ala Leu Gly Gln
 1               5                  10                  15

Thr Ala Arg Ile Thr Cys Ser Gly Asp Ser Ile Gly Asp Lys Tyr Val
                20                  25                  30

Tyr Trp Tyr Gln Gln Lys Pro Gly Gln Ala Pro Val Leu Val Ile Tyr
            35                  40                  45

Asp Thr Asn Lys Arg Pro Ser Gly Ile Pro Glu Arg Phe Ser Gly Ser
 50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Gln Ser Trp Asp Leu Asp Phe Asn Thr
                 85                  90                  95

Tyr Val Phe Gly Gly Gly Thr Lys Leu Thr Val Leu
                100                 105

<210> SEQ ID NO 75
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Tyr Met Ser Trp Val Arg Gln Ala Pro Gly Gln Gly Leu Glu Trp Met
            35                  40                  45

Gly Trp Ile Asn Pro Leu Lys Gly Asn Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Glu Asp Thr Ala Val Tyr Tyr Cys
                 85                  90                  95

Ala Arg Glu Gly Met Tyr Phe Asp Ile Trp Gly Gln Gly Thr Leu Val
                100                 105                 110

Thr Val Ser Ser Ala Ser Thr Lys Gly Pro Ser Val Phe Pro Leu Ala
```

115                 120                 125
Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys
210                 215

<210> SEQ ID NO 76
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ser Tyr Glu Leu Thr Gln Pro Leu Ser Val Ser Val Ala Leu Gly Gln
1               5                   10                  15

Thr Ala Arg Ile Thr Cys Ser Gly Asp Ser Ile Gly Asp Lys Tyr Val
            20                  25                  30

Tyr Trp Tyr Gln Gln Lys Pro Gly Gln Ala Pro Val Leu Val Ile Tyr
        35                  40                  45

Asp Thr Asn Lys Arg Pro Ser Gly Ile Pro Glu Arg Phe Ser Gly Ser
50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Trp Asp Leu Asp Phe Asn Thr
                85                  90                  95

Tyr Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
210

<210> SEQ ID NO 77
<211> LENGTH: 348
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 77
caggtgcagc tggtgcagtc aggcgccgaa gtgaagaaac ccggcgctag tgtgaaggtg    60
tcctgtaaag ctagtggcta caccttcact agctactaca tgagctgggt gcgacaggcc   120
cctggacagg gcctggaatg gatgggctgg attaccccc tgaagggcaa cactaactac    180
gcccagaaat tccagggccg agtgactatg actagggaca ctagcattag caccgcctac   240
atggaactgt ctaggctgag atcagaggac accgccgtgt actactgcgc tagagaaggc   300
atgtacttcg acatctgggg ccagggcacc ctggtgacag tgtcttct               348

<210> SEQ ID NO 78
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
agctacgagc tgactcagcc cctgagcgtg tcagtggccc tgggacagac cgctagaatc    60
acctgtagcg gcgactctat cggcgacaaa tacgtgtact ggtatcagca gaagcccggc   120
caggcccccg tgctggtgat ctacgacact aacaagcggc ctagcggcat ccccgagcgg   180
tttagcggct ctaatagcgg caacaccgct accctgacta ttagtagggc tcaggccggc   240
gacgaggccg actactactg tcagtcatgg gacctggact caacaccta cgtgttcggc    300 ggaggcacta agctgaccgt gctg                                         324

<210> SEQ ID NO 79
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
caggtgcagc tggtgcagtc aggcgccgaa gtgaagaaac ccggcgctag tgtgaaggtg    60
tcctgtaaag ctagtggcta caccttcact agctactaca tgagctgggt gcgacaggcc   120
cctggacagg gcctggaatg gatgggctgg attaccccc tgaagggcaa cactaactac    180
gcccagaaat tccagggccg agtgactatg actagggaca ctagcattag caccgcctac   240
atggaactgt ctaggctgag atcagaggac accgccgtgt actactgcgc tagagaaggc   300
atgtacttcg acatctgggg ccagggcacc ctggtgacag tgtcttctgc tagcactaag   360
gccccctccg tgttccctct ggccccttcc agcaagtcta cctctggcgg caccgctgct   420
ctgggctgcc tggtgaagga ctacttccct gagcctgtga cagtgtcctg gaactctggc   480
gccctgacct ccggcgtgca caccttccct gccgtgctgc agtcctccgg cctgtactcc   540
ctgtcctccg tggtgacagt gccttcctcc agcctgggca cccagaccta tatctgcaac   600
gtgaaccaca agccttccaa caccaaggtg gacaagcggg tggagcctaa gtcatgc     657

<210> SEQ ID NO 80
<211> LENGTH: 642
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 80
agctacgagc tgactcagcc cctgagcgtg tcagtggccc tgggacagac cgctagaatc    60
acctgtagcg gcgactctat cggcgacaaa tacgtgtact ggtatcagca gaagcccggc   120
caggcccccg tgctggtgat ctacgacact aacaagcggc ctagcggcat ccccgagcgg   180
tttagcggct ctaatagcgg caacaccgct accctgacta ttagtagggc tcaggccggc   240
gacgaggccg actactactg tcagtcatgg gacctggact caacaccta cgtgttcggc    300 ggaggcacta agctgaccgt gctgggccag cctaaggctg cccccagcgt gaccctgttc   360 cccccagca gcgaggagct gcaggccaac aaggccaccc tggtgtgcct gatcagcgac    420
ttctacccag cgccgtgac cgtggcctgg aaggccgaca gcagcccgt gaaggccggc     480 gtggagacca ccaccccag caagcagagc aacaacaagt acgccgccag cagctacctg    540
agcctgaccc ccgagcagtg gaagagccac aggtcctaca gctgccaggt gacccacgag   600
ggcagcaccg tggaaaagac cgtggcccca accgagtgca gc                      642

<210> SEQ ID NO 81
<211> LENGTH: 166
<212> TYPE: PRT
<213> ORGANISM: Homo sapiens

<400> SEQUENCE: 81

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 82
<211> LENGTH: 165
<212> TYPE: PRT
<213> ORGANISM: Macaca fascicularis

<400> SEQUENCE: 82

Ala Pro Pro Arg Leu Ile Cys Asp Ser Arg Val Leu Glu Arg Tyr Leu
1               5                   10                  15

```
Leu Glu Ala Lys Glu Ala Glu Asn Val Thr Met Gly Cys Ser Glu Ser
              20                  25                  30

Cys Ser Leu Asn Glu Asn Ile Thr Val Pro Asp Thr Lys Val Asn Phe
             35                  40                  45

Tyr Ala Trp Lys Arg Met Glu Val Gly Gln Gln Ala Val Glu Val Trp
 50                      55                  60

Gln Gly Leu Ala Leu Leu Ser Glu Ala Val Leu Arg Gly Gln Ala Val
 65                  70                  75                  80

Leu Ala Asn Ser Ser Gln Pro Phe Glu Pro Leu Gln Leu His Met Asp
                 85                  90                  95

Lys Ala Ile Ser Gly Leu Arg Ser Ile Thr Thr Leu Leu Arg Ala Leu
                100                 105                 110

Gly Ala Gln Glu Ala Ile Ser Leu Pro Asp Ala Ala Ser Ala Ala Pro
            115                 120                 125

Leu Arg Thr Ile Thr Ala Asp Thr Phe Cys Lys Leu Phe Arg Val Tyr
        130                 135                 140

Ser Asn Phe Leu Arg Gly Lys Leu Lys Leu Tyr Thr Gly Glu Ala Cys
145                 150                 155                 160

Arg Arg Gly Asp Arg
            165

<210> SEQ ID NO 83
<211> LENGTH: 166
<212> TYPE: PRT
<213> ORGANISM: Mus musculus

<400> SEQUENCE: 83

Ala Pro Pro Arg Leu Ile Cys Asp Ser Arg Val Leu Glu Arg Tyr Ile
 1               5                  10                  15

Leu Glu Ala Lys Glu Ala Glu Asn Val Thr Met Gly Cys Ala Glu Gly
              20                  25                  30

Pro Arg Leu Ser Glu Asn Ile Thr Val Pro Asp Thr Lys Val Asn Phe
             35                  40                  45

Tyr Ala Trp Lys Arg Met Glu Val Glu Glu Gln Ala Ile Glu Val Trp
 50                      55                  60

Gln Gly Leu Ser Leu Leu Ser Glu Ala Ile Leu Gln Ala Gln Ala Leu
 65                  70                  75                  80

Leu Ala Asn Ser Ser Gln Pro Pro Glu Thr Leu Gln Leu His Ile Asp
                 85                  90                  95

Lys Ala Ile Ser Gly Leu Arg Ser Leu Thr Ser Leu Leu Arg Val Leu
                100                 105                 110

Gly Ala Gln Lys Glu Leu Met Ser Pro Pro Asp Thr Thr Pro Pro Ala
            115                 120                 125

Pro Leu Arg Thr Leu Thr Val Asp Thr Phe Cys Lys Leu Phe Arg Val
        130                 135                 140

Tyr Ala Asn Phe Leu Arg Gly Lys Leu Lys Leu Tyr Thr Gly Glu Val
145                 150                 155                 160

Cys Arg Arg Gly Asp Arg
            165

<210> SEQ ID NO 84
<211> LENGTH: 166
<212> TYPE: PRT
<213> ORGANISM: Rattus norvegicus

<400> SEQUENCE: 84
```

```
Ala Pro Pro Arg Leu Ile Cys Asp Ser Arg Val Leu Glu Arg Tyr Ile
1               5                   10                  15

Leu Glu Ala Lys Glu Ala Glu Asn Val Thr Met Gly Cys Ala Glu Gly
            20                  25                  30

Pro Arg Leu Ser Glu Asn Ile Thr Val Pro Asp Thr Lys Val Asn Phe
                35                  40                  45

Tyr Ala Trp Lys Arg Met Lys Val Glu Glu Gln Ala Val Glu Val Trp
    50                  55                  60

Gln Gly Leu Ser Leu Leu Ser Glu Ala Ile Leu Gln Ala Gln Ala Leu
65                  70                  75                  80

Gln Ala Asn Ser Ser Gln Pro Pro Glu Ser Leu Gln Leu His Ile Asp
                85                  90                  95

Lys Ala Ile Ser Gly Leu Arg Ser Leu Thr Ser Leu Leu Arg Val Leu
                100                 105                 110

Gly Ala Gln Lys Glu Leu Met Ser Pro Pro Asp Ala Thr Gln Ala Ala
                115                 120                 125

Pro Leu Arg Thr Leu Thr Ala Asp Thr Phe Cys Lys Leu Phe Arg Val
                130                 135                 140

Tyr Ser Asn Phe Leu Arg Gly Lys Leu Lys Leu Tyr Thr Gly Glu Ala
145                 150                 155                 160

Cys Arg Arg Gly Asp Arg
                165

<210> SEQ ID NO 85
<211> LENGTH: 199
<212> TYPE: PRT
<213> ORGANISM: Oryctolagus cuniculus

<400> SEQUENCE: 85

Lys Leu Ala Thr Met Gly Val Arg Gly Arg Leu Ala Leu Leu Pro Leu
1               5                   10                  15

Ala Leu Leu Cys Leu Leu Val Leu Ala Leu Gly Leu Pro Val Leu Gly
                20                  25                  30

Ala Pro Ala Arg Leu Ile Cys Asp Ser Arg Val Leu Glu Arg Tyr Ile
                35                  40                  45

Leu Glu Ala Lys Glu Ala Glu Asn Val Thr Met Gly Cys Ala Glu Gly
    50                  55                  60

Cys Ser Leu Gly Glu Asn Ile Thr Val Pro Asp Thr Lys Val Asn Phe
65                  70                  75                  80

His His Trp Lys Lys Ser Glu Ala Gly Arg His Ala Val Glu Val Trp
                85                  90                  95

Gln Gly Leu Ala Leu Leu Ser Glu Ala Met Leu Arg Ser Gln Ala Leu
                100                 105                 110

Leu Ala Asn Ser Ser Gln Leu Pro Glu Thr Leu Gln Val His Val Asp
                115                 120                 125

Lys Ala Val Ser Gly Leu Arg Ser Leu Thr Ser Leu Leu Arg Ala Leu
                130                 135                 140

Gly Val Gln Lys Glu Ala Val Ser Pro Pro Glu Ala Ala Ser Ser Ala
145                 150                 155                 160

Ala Pro Leu Arg Thr Val Ala Ala Asp Thr Leu Cys Lys Leu Phe Arg
                165                 170                 175

Ile Tyr Ser Asn Phe Leu Arg Gly Lys Leu Lys Leu Tyr Thr Gly Glu
                180                 185                 190

Ala Cys Arg Arg Gly Asp Arg
                195
```

<210> SEQ ID NO 86
<211> LENGTH: 23
<212> TYPE: PRT
<213> ORGANISM: Homo sapiens

<400> SEQUENCE: 86

Arg Leu Ile Cys Asp Ser Arg Val Leu Glu Arg Tyr Leu Leu Glu Ala
1               5                   10                  15

Lys Glu Ala Glu Asn Ile Thr
            20

<210> SEQ ID NO 87
<211> LENGTH: 28
<212> TYPE: PRT
<213> ORGANISM: Homo sapiens

<400> SEQUENCE: 87

Val Gly Gln Gln Ala Val Glu Val Trp Gln Gly Leu Ala Leu Leu Ser
1               5                   10                  15

Glu Ala Val Leu Arg Gly Gln Ala Leu Leu Val Asn
            20                  25

<210> SEQ ID NO 88
<211> LENGTH: 25
<212> TYPE: PRT
<213> ORGANISM: Homo sapiens

<400> SEQUENCE: 88

Phe Arg Lys Leu Phe Arg Val Tyr Ser Asn Phe Leu Arg Gly Lys Leu
1               5                   10                  15

Lys Leu Tyr Thr Gly Glu Ala Cys Arg
            20                  25

<210> SEQ ID NO 89
<211> LENGTH: 29
<212> TYPE: PRT
<213> ORGANISM: Homo sapiens

<400> SEQUENCE: 89

Thr Gly Cys Ala Glu His Cys Ser Leu Asn Glu Asn Ile Thr Val Pro
1               5                   10                  15

Asp Thr Lys Val Asn Phe Tyr Ala Trp Lys Arg Met Glu
            20                  25

<210> SEQ ID NO 90
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Pro Leu Gln Leu His Val Asp Lys Ala Val Ser Gly Leu Arg Ser
1               5                   10                  15

Leu Thr Thr Leu Leu Arg Ala Leu Gly Ala Gln Lys Glu Ala Ile Ser
            20                  25                  30

Pro Pro Asp
        35

<210> SEQ ID NO 91

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Lys Ala Val Ser Gly Leu Arg Ser Leu Thr Thr Leu Leu Arg Ala
1               5                   10                  15

Leu

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 92

His His His His His His
1               5

<210> SEQ ID NO 93
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Leu Ile Cys Asp Ser Arg Val Leu Glu Arg Tyr Leu Leu Glu Ala
1               5                   10                  15

Lys Glu Ala Glu Asn Ile Thr Thr Gly
            20                  25

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Thr Val Pro Asp Thr Lys Val Asn Phe Tyr Ala Trp Lys Arg Met
1               5                   10                  15

<210> SEQ ID NO 95
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gly Gln Gln Ala Val Glu Val Trp Gln Gly Leu Ala Leu Leu
1               5                   10                  15

Ser Glu Ala Val Leu Arg Gly Gln Ala Leu Leu Val Asn Ser
            20                  25                  30

<210> SEQ ID NO 96
<211> LENGTH: 26
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Phe Arg Lys Leu Phe Arg Val Tyr Ser Asn Phe Leu Arg Gly Lys
1               5                   10                  15

Leu Lys Leu Tyr Thr Gly Glu Ala Cys Arg
            20                  25

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Lys Val Asn Phe Tyr Ala Trp Lys Arg
1               5                   10
```